US008507721B2

(12) United States Patent
Herzog et al.

(10) Patent No.: US 8,507,721 B2
(45) Date of Patent: Aug. 13, 2013

(54) PROCESS FOR PREPARING ACRYLIC ACID FROM ETHANOL AND FORMALDEHYDE

(75) Inventors: Stefanie Herzog, Berlin (DE); Stefan Altwasser, Wachenheim (DE); Markus Ottenbacher, Wilhelmsfeld (DE); Frank Huetten, Mannheim (DE); Annebart Engbert Wentink, Mannheim (DE); Alexander Schaefer, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/232,380

(22) Filed: Sep. 14, 2011

(65) Prior Publication Data

US 2012/0071687 A1    Mar. 22, 2012

Related U.S. Application Data

(60) Provisional application No. 61/383,358, filed on Sep. 16, 2010.

(30) Foreign Application Priority Data

Sep. 16, 2010  (DE) .......................... 10 2010 040 923

(51) Int. Cl.
*C07B 35/00*    (2006.01)

(52) U.S. Cl.
USPC ........................................................ 562/599

(58) Field of Classification Search
None
See application file for complete search history.

(56) References Cited

U.S. PATENT DOCUMENTS

| | | | |
|---|---|---|---|
| 3,152,997 A | 10/1964 | Natta et al. | |
| 3,198,753 A | 8/1965 | Traina | |
| 3,408,309 A | 10/1968 | Gessner | |
| 3,464,930 A | 9/1969 | Friedrichsen et al. | |
| 3,716,497 A | 2/1973 | Courty | |
| 3,775,474 A | 11/1973 | Ohara et al. | |
| 3,846,341 A | 11/1974 | Courty | |
| 3,893,951 A | 7/1975 | Grasselli et al. | |
| 3,954,855 A | 5/1976 | Wada et al. | |
| 3,954,857 A | 5/1976 | Brockhaus | |
| 3,975,302 A | 8/1976 | Courty et al. | |
| 3,978,136 A | 8/1976 | Friedrich et al. | |
| 3,983,073 A | 9/1976 | Trifiro et al. | |
| 3,987,107 A | 10/1976 | McClellan et al. | |
| 3,994,977 A | 11/1976 | Aicher et al. | |
| 4,048,112 A | 9/1977 | Matsushita et al. | |
| 4,080,383 A | 3/1978 | Diem et al. | |
| 4,228,038 A | 10/1980 | König | |
| 4,339,355 A | 7/1982 | Decker et al. | |
| 4,343,954 A | 8/1982 | Hoene | |
| 4,448,897 A | 5/1984 | Gastinger | |
| 4,584,412 A | 4/1986 | Aicher et al. | |
| 4,795,818 A | 1/1989 | Becker et al. | |
| 4,829,042 A | 5/1989 | Cavalli et al. | |
| 4,933,312 A | 6/1990 | Haddad et al. | |
| 5,095,125 A | 3/1992 | Haddad et al. | |
| 5,137,860 A | 8/1992 | Ebner et al. | |
| 5,158,923 A | 10/1992 | Barone | |
| 5,275,996 A | 1/1994 | Andrews et al. | |
| 5,296,436 A | 3/1994 | Bortinger | |
| 5,641,722 A | 6/1997 | Mitchell et al. | |
| 5,840,971 A * | 11/1998 | Gubelmann-Bonneau | ... 562/538 |
| 7,030,269 B2 * | 4/2006 | Yunoki et al. | .................. 562/535 |
| 2011/0105791 A1 | 5/2011 | Kuppinger et al. | |

FOREIGN PATENT DOCUMENTS

| | | |
|---|---|---|
| BE | 683130 | 12/1966 |
| DE | 1 231 229 | 12/1966 |
| DE | 1 294 360 | 5/1969 |
| DE | 1 903 197 | 8/1970 |
| DE | 1 618 413 | 10/1970 |
| DE | 1 642 938 | 5/1971 |
| DE | 2 145 851 | 3/1973 |
| DE | 23 34 981 | 1/1975 |
| DE | 24 42 311 | 3/1975 |
| DE | 25 33 209 | 2/1976 |
| DE | 26 26 887 | 12/1977 |
| DE | 28 30 765 | 1/1980 |
| DE | 29 09 671 | 10/1980 |
| DE | 31 51 805 A1 | 7/1983 |
| DE | 35 20 053 A1 | 12/1985 |
| DE | 43 02 991 A1 | 8/1994 |
| DE | 196 49 426 A1 | 6/1998 |

(Continued)

OTHER PUBLICATIONS

Ai et al., Journal of Catalysis 107, 201-208 (1987).*
International Search Report issued Jan. 30, 2012, in PCT/EP2011/065863 with English translation of category of cited documents.
Mamoru AI, "Vapor-Phase Aldol Condensation of Formaldehyde with Acetic Acid on $V_2O_5$-$P_2O_5$ Catalysts", Journal of Catalysis, vol. 107, XP-002667283, 1987, pp. 201-208.
Ana Paula Vieira Soares, et al., "Methanol Selective Oxidation to Formaldehyde over Iron-Molybdate Catalysts", Catalysis Reviews, vol. 47, 2004, pp. 125-174.
"Fibers, 5. Synthetic Inorganic, to Formaldehyde", Ullmann's Encyclopedia of Industrial Chemistry, Fifth, Completely Revised Edition, vol. A 11, 1988, pp. 624-627.
Arno Behr, et al., "Alternative Synthesewege zum Ethylen", Chemie Ingenieur Technik, vol. 82, No. 3, Feb. 9, 2010, pp. 201-213.
A. Behr, et al., "Alternative Synthesewege zum Ethylen", Chemie Ingenieur Technik, vol. 82, No. 3, 2010, pp. 176-179.
U.S. Appl. No. 13/233,560, filed Sep. 15, 2011, Herzog, et al.

*Primary Examiner* — Karl J Puttlitz

(74) *Attorney, Agent, or Firm* — Oblon, Spivak, McClelland, Maier & Neustadt, L.L.P.

(57) ABSTRACT

A process for preparing acrylic acid from ethanol and formaldehyde, in which, in a reaction zone A, the ethanol is partially oxidized to acetic acid in a heterogeneously catalyzed gas phase reaction, the product gas mixture A obtained and a formaldehyde source are used to obtain a reaction gas input mixture B which comprises acetic acid and formaldehyde and has the acetic acid in excess over the formaldehyde, and the formaldehyde present in reaction gas input mixture B is aldol-condensed with acetic acid present in reaction gas input mixture B to acrylic acid under heterogeneous catalysis in a reaction zone B, and unconverted acetic acid still present along-side the acrylic acid target product in the product gas mixture B obtained is removed therefrom, and the acetic acid removed is recycled into the production of reaction gas input mixture B.

19 Claims, No Drawings

(56) References Cited

FOREIGN PATENT DOCUMENTS

| | | |
|---|---|---|
| DE | 197 36 105 A1 | 2/1999 |
| DE | 198 54 575 A1 | 5/2000 |
| DE | 199 24 532 A1 | 11/2000 |
| DE | 199 27 624 A1 | 12/2000 |
| DE | 697 02 728 T2 | 2/2001 |
| DE | 199 48 241 A1 | 4/2001 |
| DE | 199 48 523 A1 | 4/2001 |
| DE | 102 35 847 A1 | 8/2003 |
| DE | 103 13 209 A1 | 3/2004 |
| DE | 103 36 386 A1 | 3/2004 |
| DE | 102 43 625 A1 | 4/2004 |
| DE | 103 60 057 A1 | 7/2004 |
| DE | 103 13 208 A1 | 10/2004 |
| DE | 103 13 210 A1 | 10/2004 |
| DE | 103 25 487 A1 | 12/2004 |
| DE | 103 25 488 A1 | 12/2004 |
| DE | 103 61 456 A1 | 7/2005 |
| DE | 10 2004 004 496 A1 | 8/2005 |
| DE | 10 2004 017 150 A1 | 10/2005 |
| DE | 10 2004 057 868 A1 | 6/2006 |
| DE | 10 2004 057 874 A1 | 6/2006 |
| DE | 10 2005 035 978 A1 | 2/2007 |
| DE | 10 2005 062 929 A1 | 7/2007 |
| DE | 10 2006 024 901 A1 | 11/2007 |
| DE | 10 2007 005 606 A1 | 4/2008 |
| DE | 10 2007 004 960 A1 | 7/2008 |
| DE | 10 2008 040 093 A1 | 12/2008 |
| DE | 10 2008 040 094 A1 | 1/2009 |
| DE | 10 2007 055 086 A1 | 5/2009 |
| DE | 10 2009 027 401 A1 | 2/2010 |
| DE | 10 2008 059 701 A1 | 6/2010 |
| DE | 10 2008 060 310 A1 | 6/2010 |
| DE | 10 2010 028 328 A1 | 11/2011 |
| DE | 10 2010 023 312 A1 | 12/2011 |
| EP | 0 164 614 | 12/1985 |
| EP | 0 199 359 A2 | 10/1986 |
| EP | 0 294 846 A2 | 12/1988 |
| EP | 0 427 508 A1 | 5/1991 |
| EP | 0 551 111 A1 | 7/1993 |
| EP | 0 614 872 A1 | 9/1994 |
| EP | 0 700 714 A1 | 3/1996 |
| EP | 0 700 893 A1 | 3/1996 |
| EP | 0 714 700 A2 | 6/1996 |
| EP | 0 778 255 A1 | 6/1997 |
| EP | 1 041 062 A2 | 10/2000 |
| EP | 1 651 344 | 5/2006 |
| EP | 2 213 370 A2 | 8/2010 |
| EP | 2 220 004 | 8/2010 |
| WO | WO 95/11081 | 4/1995 |
| WO | WO 95/26817 | 10/1995 |
| WO | WO 97/12674 | 4/1997 |
| WO | WO 01/68245 A1 | 9/2001 |
| WO | WO 01/77056 A1 | 10/2001 |
| WO | WO 03/053556 A2 | 7/2003 |
| WO | WO 03/055835 A1 | 7/2003 |
| WO | WO 03/057653 A1 | 7/2003 |
| WO | WO 03/078310 A2 | 9/2003 |
| WO | WO 2004/007405 A1 | 1/2004 |
| WO | WO 2005/042459 A1 | 5/2005 |
| WO | WO 2005/063375 A1 | 7/2005 |
| WO | WO 2005/093010 A2 | 10/2005 |
| WO | WO 2006/094766 A1 | 9/2006 |
| WO | WO 2007/012620 A1 | 2/2007 |
| WO | WO 2007/059974 A1 | 5/2007 |
| WO | WO 2007/082827 A1 | 7/2007 |
| WO | WO 2008/023039 A1 | 2/2008 |
| WO | WO 2008/023040 A2 | 2/2008 |
| WO | WO 2008/087116 A1 | 7/2008 |
| WO | 2008010468 * | 9/2008 |
| WO | WO 2008/110468 A1 | 9/2008 |
| WO | WO 2008/116840 A1 | 10/2008 |
| WO | WO 2008/152079 A1 | 12/2008 |
| WO | WO 2009/149809 A1 | 12/2009 |
| WO | WO 2010/000720 A2 | 1/2010 |
| WO | WO 2010/000764 A2 | 1/2010 |
| WO | WO 2010/022923 A1 | 3/2010 |
| WO | WO 2010/034480 A2 | 4/2010 |
| WO | WO 2010/060236 A1 | 6/2010 |
| WO | WO 2010/060279 A1 | 6/2010 |
| WO | WO 2010/062936 A1 | 6/2010 |
| WO | WO 2010/067945 A1 | 6/2010 |
| WO | WO 2010/072424 A1 | 7/2010 |
| WO | WO 2010/072721 A2 | 7/2010 |
| WO | WO 2010/072723 A2 | 7/2010 |
| WO | WO 2010/092819 A1 | 8/2010 |
| WO | WO 2011/067363 A2 | 6/2011 |

* cited by examiner

PROCESS FOR PREPARING ACRYLIC ACID FROM ETHANOL AND FORMALDEHYDE

The present invention relates to a process for preparing acrylic acid from ethanol and formaldehyde. The present invention also relates to the preparation of conversion products from acrylic acid thus obtained.

At present, acrylic acid is prepared on the industrial scale essentially exclusively by heterogeneously catalyzed two-stage partial oxidation of propylene (see, for example, DE-A 103 36 386).

One advantage of this procedure is that it has a comparatively high target product selectivity based on propylene converted, which, in the case of recycling of propylene unconverted in single pass, enables high acrylic acid yields from the propylene used. Furthermore, propylene has extremely economically viable backward integration to the base fossil raw material, mineral oil (i.e. propylene can be produced from mineral oil with comparatively low production costs), which enables inexpensive acrylic acid preparation overall.

In view of the foreseeable shortage in the fossil resource of mineral oil, there will, however, be a need in the future for processes for preparing acrylic acid from raw materials, which can be performed in a comparatively economically viable manner even without backward integration thereof to the base fossil raw material, mineral oil, and which at the same time have backward integration of the raw materials thereof to base raw materials whose lifetimes extend beyond that of mineral oil.

WO 2005/093010 considers propylene itself to be such a raw material. It proposes continuing, in the future, with the two-stage heterogeneously catalyzed partial gas phase oxidation of propylene to acrylic acid, but obtaining the propylene required from methanol. The advantage of such a procedure is that methanol is obtainable both proceeding from base fossil raw materials such as coal, for example brown coal and hard coal; cf., for example, WO 2010/072424) and natural gas (cf., for example, WO 2010/067945), both of which have a much longer lifetime than mineral oil, and proceeding from the renewable base raw material of biomass, and also directly from the carbon dioxide present in the earth's atmosphere (in each case optionally with additional use of steam or molecular hydrogen) (cf., for example, G. A. Olah et al., Beyond Oil and Gas; The Methanol Economy, Wiley-VCH, 2009).

However, a disadvantage of the procedure proposed in WO 2005/093010 is that the selectivity of obtaining propylene proceeding from methanol with the preparation processes currently known, based on methanol converted, is less than 70 mol %, which is unsatisfactory (in addition to propylene, for example, ethylene and butylene are also formed).

In this document, base fossil raw materials shall be understood to mean base raw materials which, like brown coal, hard coal, natural gas and mineral oil, for example, originate from degradation products of dead plants and dead animals in geological prehistory.

In contrast, in this document, renewable raw materials shall be understood to mean those raw materials which are obtained from fresh biomass, i.e. from (new) vegetable and animal material which is being newly grown (in the present) and will be grown in the future.

There have also already been proposals (for example in WO 2008/023040) to prepare acrylic acid and the conversion products thereof proceeding from the renewable raw material glycerol. However, a disadvantage of such a procedure is that glycerol is obtainable economically as a renewable raw material essentially only as a coproduct of biodiesel production. This is disadvantageous in that the current energy balance of biodiesel production is unsatisfactory.

Furthermore, the prior art has proposed the preparation of acrylic acid from propane (for example in DE-A 102006024901), which constitutes a raw constituent of natural gas. However, a disadvantage of such a method of preparation of acrylic acid is firstly the comparatively high unreactiveness of propane, and the fact that propane also constitutes a sought-after energy carrier with good manageability.

It was therefore an object of the present invention to provide an alternative process for preparing acrylic acid, which does not have the described disadvantages of the prior art processes, and especially has a satisfactory selectivity of target product formation proceeding from the raw materials used for preparation thereof.

Accordingly, a process for preparing acrylic acid from ethanol and formaldehyde is provided.

The appeal of such a procedure is firstly that ethanol is the most sustainable renewable raw material (ethanol is formed by a natural route in the fermentation of glucose-comprising biomass; however, it is also possible to proceed from starch- and cellulose-comprising biomass, by using an upstream enzymatic or acidic conversion process which converts the starch and cellulose types to glucose; cf., for example, WO 2010/092819).

In principle, ethanol, however, is also obtainable on the industrial scale by reacting water with ethylene with addition of catalysts such as sulfuric acid, or phosphoric acid applied to starch, at temperatures of about 300° C. and pressures of around 70 bar, with the advantage that ethylene has close backward integration to fossil resources such as natural gas and coal, which have a longer lifetime than mineral oil (e.g. Chemie Ingenieur Technik—CIT, Volume 82, pages 201-213, Issue 3, Published Online on Feb. 9, 2010, Wiley—VCH Verlag Weinheim, "Alternative Synthesewege zum Ethylen" ["Alternative synthesis routes to ethylene"], A. Behr, A. Kleyentreiber and H. Hertge).

A further advantage of the inventive procedure is based on the fact that formaldehyde is obtainable by partial oxidation of methanol (e.g. Catalysis Review 47, pages 125 to 174, 2004; EP-A 2213370; WO 2010/022923; DE-A 2334981; DE-A 1618413; WO 2009/149809; DE-A 2145851; WO 2005/063375; WO 03/053556; WO 2010/034480; WO 2007/059974; DE-A 102008059701 and Ullmann's Encyclopedia of Industrial Chemistry, Fifth, Completely Revised Edition, Volume A 11, 1988 pages 624 to 627), and methanol can be obtained via synthesis gas (gas mixtures of carbon monoxide and molecular hydrogen) in principle from all carbonaceous base fossil fuels and all carbonaceous renewable raw materials (as in the case of methane, the molecular hydrogen required (a process for obtaining methane from biogas or biomass is described, for example, by DE-A 102008060310 or EP-A 2220004) may already be present in the carbon carrier; an alternative hydrogen source available is water, from which molecular hydrogen can be obtained, for example, by means of electrolysis; the oxygen source is generally air; cf., for example, WO 10-060236 and WO 10-060279). A suitable renewable carbonaceous raw material is, for example, lignocellulose for synthesis gas production (cf., for example, WO 10-062936). It is also possible to obtain synthesis gas by coupling the pyrolysis of biomass directly with steam reforming.

The present invention thus provides a process for preparing acrylic acid from ethanol and formaldehyde, which comprises the following measures:

a stream of a reaction gas input mixture A comprising the ethanol and molecular oxygen reactants and at least one inert diluent gas other than steam is conducted through a first reaction zone A charged with at least one oxidation catalyst A and, in the course of passage through reaction zone A, ethanol present in the reaction gas input mixture A is oxidized under heterogeneous catalysis to acetic acid and steam so as to form a product gas mixture A comprising acetic acid, steam, molecular oxygen and at least one inert diluent gas other than steam, and a stream of product gas mixture A leaves reaction zone A, it optionally being possible to supply further molecular oxygen and/or further inert diluent gas to the reaction gas mixture A flowing through reaction zone A on its way through reaction zone A, a stream of a reaction gas input mixture B which comprises acetic acid, steam, molecular oxygen, at least one inert diluent gas other than steam and formaldehyde and in which the molar amount $n_{HAc}$ of acetic acid present is greater than the molar amount $n_{Fd}$ of formaldehyde present therein is obtained from the stream of product gas mixture A leaving reaction zone A (without having to carry out a separation process thereon beforehand) and at least one further stream comprising at least one formaldehyde source, the stream of reaction gas input mixture B is passed through a second reaction zone B charged with at least one aldol condensation catalyst B and formaldehyde present in reaction gas input mixture B, as it flows through reaction zone B, is condensed with acetic acid present in reaction gas input mixture B under heterogeneous catalysis to give acrylic acid and $H_2O$, so as to form a product gas mixture B comprising acrylic acid, acetic acid, steam, molecular oxygen and at least one inert diluent gas other than steam, and a stream of product gas mixture B leaves reaction zone B, it optionally being possible to supply further molecular oxygen and/or further inert diluent gas to the reaction gas mixture B flowing through reaction zone B on its way through reaction zone B, the stream of product gas mixture B leaving reaction zone B is fed to a separation zone T and separated in separation zone T into at least three streams X, Y and Z, the acrylic acid flow present in stream X being greater than the acrylic acid flow present in streams Y and Z together, the acetic acid flow present in stream Y being greater than the acetic acid flow present in streams X and Z together, the flow of inert diluent gas other than steam present in stream Z being greater than the flow of inert diluent gas other than steam present in streams X and Y together, and stream Y is recycled into reaction zone B and used to obtain reaction gas input mixture B.

Preferably in accordance with the invention, reaction zone A is charged with at least one oxidation catalyst A comprising at least one vanadium oxide.

More preferably, reaction zone A is charged with at least one oxidation catalyst A which comprises at least one vanadium oxide and, as well as the at least one vanadium oxide, additionally comprises at least one oxide from the group of the oxides of titanium, of aluminum, of zirconium and of tin.

Most preferably, reaction zone A is charged with at least one oxidation catalyst A which comprises at least one vanadium oxide and, as well as the at least one vanadium oxide, additionally comprises at least one oxide of titanium.

Advantageously in accordance with the invention, the oxidation catalysts A comprise the vanadium in the +5 oxidation state. In other words, the oxidation catalysts A comprising at least one vanadium oxide comprise, appropriately in accordance with the invention, the (vanadium oxide) unit of $V_2O_5$ (vanadium pentoxide).

In contrast, the aforementioned oxidation catalysts A, in the case of the elements Ti, Zr and Sn, comprise them advantageously in the +4 oxidation state. In other words, the oxidation catalysts comprising, as well as a vanadium oxide, additionally at least one oxide from the group of titanium oxide, zirconium oxide and tin oxide, appropriately in accordance with the invention, comprise at least one unit (the element dioxide) from the group of $TiO_2$, $ZrO_2$ and $SnO_2$, the $TiO_2$ unit being very particularly advantageous within this group for the inventive purposes, especially when it is present in the anatase polymorph.

Quite generally, oxidation catalysts A preferred in accordance with the invention are mixed oxide catalysts A comprising at least one vanadium oxide, the term "mixed oxide" expressing the fact that the catalytically active oxide comprises at least two different metal elements.

Suitable oxidation catalysts A comprising at least one vanadium oxide are, in accordance with the invention, for example, all oxidation catalysts disclosed in EP-A 294846. These are especially those oxidation catalysts of EP-A 294846 which, neglecting the oxygen present, have the stoichiometry $Mo_xV_yZ_z$ in which Z may be absent or may be at least one particular metal element.

Further oxidation catalysts A which comprise at least one vanadium oxide and are suitable in accordance with the invention are the mixed oxide catalysts which are disclosed in U.S. Pat. No. 5,840,971 and whose active material consists of the elements vanadium, titanium and oxygen.

The supported catalysts which comprise vanadium pentoxide and titanium dioxide and are prepared for use for the partial oxidation of o-xylene to phthalic anhydride in DE-A 1642938 are also suitable in accordance with the invention as oxidation catalysts A.

Very particular preference is given to using, for the process according to the invention, as oxidation catalysts A comprising at least one vanadium oxide, those which are recommended in this regard in the priority-establishing EP application number 09178015.5.

Mixed oxide catalysts A which comprise at least one vanadium oxide and are suitable in accordance with the invention are obtainable, for example, by the preparation process described in U.S. Pat. No. 4,048,112. This proceeds from a porous oxide of at least one of the elements Ti, Al, Zr and Sn. The latter is impregnated with a solution of a vanadium compound. Subsequently, the solvent used to prepare the solution is advantageously substantially removed (generally by the action of heat and/or reduced pressure), and the resulting catalyst precursor is subsequently calcined.

This involves decomposing the vanadium compound, generally in an atmosphere comprising molecular oxygen, to vanadium oxide. The porous oxide to be impregnated may have any desired geometric three-dimensional form. Appropriate three-dimensional forms in application terms for the process according to the invention include spheres, rings (hollow cylinders), extrudates, tableted pellets and monolithic forms. Advantageously, the longest dimension of the aforementioned geometric shaped bodies is 1 or 2 to 10 mm (the longest dimension of a shaped body in this document is generally understood to mean the longest direct line connecting two points on the surface of the shaped body). For the solution which comprises at least one dissolved vanadium compound and is to be used for the impregnation, suitable vanadium compounds are, for example, vanadium pentoxide, vanadyl chloride, vanadyl sulfate and ammonium metavanadate. The solvent used is preferably water, to which complexing agents, for example oxalic acid, are advantageously added as dissolution promoters. The removing of the solvent which is to be undertaken after the impregnation and the calcination which is to be performed may be operations which merge seamlessly into one another or else overlap. Advantageously, however, the solvent is first removed at a temperature of 100 to 200° C. This is then followed by calcination at a temperature of 400 to 800° C., or of 500 to 700° C. The calcination can be effected in an atmosphere comprising molecular oxygen, for example under air, or under inert gas. The calcination atmosphere may be stationary above the precursor material to be calcined or flow over and through the precursor material. The calcination time generally varies within the range from 0.5 h to 10 h. Higher calcination temperatures are normally associated with shorter calcination times. When comparatively low calcination temperatures are employed, the calcination generally extends over a longer period.

Optionally, the procedure of impregnation-drying-calcination can also be repeated several times in order to achieve the desired loading with vanadium oxide.

In the case of inventive mixed oxide catalysts A comprising vanadium oxide, advantageously in accordance with the invention, quite generally 0.1 to 6% by weight, preferably 1 to 50% by weight or 3 to 40% by weight, particularly advantageously 5 to 30% by weight, based in each case on the total weight of the active material, is accounted for the by the $V_2O_5$ unit.

Furthermore, in the case of inventive mixed oxide catalysts A comprising vanadium oxide and titanium oxide, advantageously 40 to 99.9% by weight, preferably 50 to 99% by weight or 60 to 97% by weight, particularly advantageously 70 to 95% by weight, based in each case on the total weight of the active material, is accounted for by the $TiO_2$ unit.

An alternative process for preparing mixed oxide catalysts A comprising vanadium oxide and titanium dioxide is described by U.S. Pat. No. 3,464,930. This involves treating finely divided titanium dioxide together with a vanadium compound. The resulting composition can then be shaped to the corresponding catalyst geometry even before or after the calcinations thereof. In principle, the calcined composition can, however, also be used in powder form as the catalyst for the relevant partial oxidation. The shaping can, for example, be effected by compacting (for example by tableting or extruding) the pulverulent active material or the uncalcined precursor material thereof to the desired catalyst geometry to produce unsupported catalysts or unsupported catalyst precursors, and the shaping may be preceded by optional addition of assistants, for example graphite or stearic acid as lubricants and/or shaping assistants and reinforcing assistants such as microfibers of glass, asbestos, silicon carbide or potassium titanate. Unsupported catalyst geometries suitable in accordance with the invention are (and quite generally in the case of oxidation catalysts A (especially in the case of corresponding unsupported catalysts A (they consist only of active material))), for example, solid cylinders and hollow cylinders having an external diameter and a length of 1 or 2 to 10 mm. In this case of the hollow cylinder, a wall thickness of 1 to 3 mm is appropriate in application terms. Otherwise, the tableting can advantageously be undertaken as described in documents WO 2008/152079, WO 2008/087116, DE-A 102008040094, DE-A 102008040093 and WO 2010/000720.

All geometries detailed in the aforementioned documents are also suitable for inventive oxidation catalysts A.

The finely divided titanium dioxide can be treated with a vanadium compound, for example with a sparingly soluble vanadium compound such as $V_2O_5$, under hydrothermal conditions. In general, it is, however, undertaken by means of a solution comprising a dissolved vanadium compound (for example in water or in an organic solvent (for example formamide or mono- and polyhydric alcohols)). The vanadium compounds used may be vanadium pentoxide, vanadyl chloride, vanadyl sulfate and ammonium metavanadate. The dissolution promoters added to the solution may be complexing agents, for example oxalic acid.

Alternatively to the unsupported catalyst, the shaping can, however, also be undertaken in the form of an eggshell catalyst. This involves using the pulverulent active material obtained or the pulverulent, as yet uncalcined precursor material, to coat the surface of an inert shaped support body using a liquid binder (when coating with uncalcined precursor material, the calcination follows the coating and generally the drying). Inert shaped support bodies differ from the catalytic active material (in this document, "catalytically active material" is quite generally also used as a synonym thereof) normally in that it has a much lower specific surface area. In general, the specific surface area thereof is less than 3 $m^2/g$ of shaped support body. At this point, it should be emphasized that all figures in this document for specific surface areas relate to determinations according to DIN 66131 (determinations of the specific surface area of solids by means of gas adsorption ($N_2$) according to Brunauer-Emmett-Teller (BET)).

Suitable materials for aforementioned inert shaped support bodies are, for example, quartz, silica glass, sintered silica, sintered or fused alumina, porcelain, sintered or fused silicates such as aluminum silicate, magnesium silicate, zinc silicate, zirconium silicate, and especially steatite (e.g. C 220 steatite from CeramTec). The geometry of the inert shaped support bodies may in principle have an irregular shape, preference being given in accordance with the invention to regularly shaped support bodies, for example spheres or hollow cylinders. Appropriately in application terms, the longest dimension of the aforementioned inert shaped support bodies for the inventive purposes is 1 to 10 mm.

The coating of the inert shaped support bodies with the particular finely divided powder is generally executed in a suitable rotatable vessel, for example in a coating drum. Appropriately in application terms, the liquid binder is sprayed onto the inert shaped support bodies and the binder-moistened surface of the shaped support bodies being moved within the coating drum is dusted with the particular powder (cf., for example, EP-A 714 700). Subsequently, the adhering liquid is generally removed at least partly from the coated shaped support body (for example by passing hot gas through the coated shaped support bodies, as described in WO 2006/094766). In principle, however, it is also possible to employ all other application processes acknowledged as prior art in EP-A 714700 to produce the relevant eggshell catalysts. Useful liquid binders include, for example, water and aqueous solutions (for example of glycerol in water). For example, the coating of the shaped support bodies can also be undertaken by spraying a suspension of the pulverulent material to be applied in liquid binder (for example water) onto this surface of the inert shaped support bodies (generally under the action of heat and a drying entraining gas). In principle, the coating can also be undertaken in a fluidized bed system or powder coating system.

The layer thickness of the active material applied to the surface of the inert shaped support body is, appropriately in application terms, selected within the range from 10 to 2000 µm, or 10 to 500 µm, or 100 to 500 µm, or 200 to 300 µm. Eggshell catalysts of the type described which are suitable in accordance with the invention for charging the reaction zone A include those whose inert shaped support body is a hollow cylinder with a length in the range from 3 to 6 mm, an external diameter in the range from 4 to 8 mm and a wall thickness in the range from 1 to 2 mm. Additionally suitable for the inventive purposes in the reaction zone A are all ring geometries disclosed in DE-A 102010028328 and in DE-A 102010023312 and all of those disclosed in EP-A 714700 for possible inert shaped support bodies for annular eggshell oxidation catalysts A.

Further processes for producing mixed oxide catalysts A which comprise vanadium oxide and titanium dioxide and are suitable in accordance with the invention are disclosed by U.S. Pat. No. 4,228,038 and U.S. Pat. No. 3,954,857. The basis of the procedure of U.S. Pat. No. 4,228,038 is a treatment of titanium dioxide with water and vanadium oxychloride until the desired vanadium content has been attained. The basis of the procedure of U.S. Pat. No. 3,954,857 is the neutralization of a solution of vanadium pentoxide and titanium tetrachloride in hydrochloric acid, which leads to a precipitation reaction. The oxidic active materials which result from the two procedures, or from the precursor materials thereof, can be used as described above to produce unsupported and eggshell catalysts suitable for reaction zone A.

A further procedure suitable in accordance with the invention for preparation of mixed oxide active materials comprising vanadium oxide and titanium dioxide for oxidation catalysts A is disclosed by U.S. Pat. No. 4,448,897. The basis of this preparation method is the mixing of a vanadyl alkoxide with a titanium alkoxide in an aqueous solution and subsequent drying and calcining of the precipitate which forms. The shaping to give unsupported or eggshell catalysts can proceed from the corresponding active material powder or the precursor material powder thereof in the manner already described (above). Finally, it should be emphasized that the catalysts which comprise vanadium oxide and are disclosed in WO 2008/110468 and in DE-A 19649426 are also suitable as oxidation catalysts A for reaction zone A of the process according to the invention. In addition, inert shaped support bodies for the eggshell oxidation catalysts A (in contrast to supported catalysts A) are preferably nonporous or low in pores. In the case of supported catalysts A, the active material is introduced into the pore structure of the shaped support body.

In addition to the oxides already mentioned, the active materials of oxidation catalysts A suitable in accordance with the invention may additionally (in addition to the element oxides already mentioned) comprise one or more oxides of the metals from the group of boron, silicon, hafnium, niobium, tungsten, lanthanum, cerium, molybdenum, chromium, antimony, alkali metal and alkaline earth metal, and also the elements of main groups 5 and 6 of the Periodic Table and other transition metals. In many cases, the total content of the aforementioned oxides, based on the total weight of the active material, is 1 to 15% by weight. An essential feature of the invention is that the term "element oxide" also comprises metalates. These are negatively charged anions formed only from the metal and oxygen.

The ethanol content in reaction gas input mixture A in the process according to the invention will generally be 0.3 to 20% by volume, preferably in application terms 0.5 to 15% by volume, more preferably 0.75 to 10% by volume and most preferably 1 to 5% by volume.

The molar amount $n_O$ of molecular oxygen present in reaction gas input mixture A will, in the process according to the invention, appropriately in application terms, be such that it is greater than the molar amount $n_{Et}$ of ethanol present in reaction gas input mixture A. In general, the $n_O:n_{Et}$ ratio in the process according to the invention will be at least 1.3, better at least 1.5, preferably at least 1.75 and more preferably at least 2. Normally, the $n_O:n_{Et}$ ratio will, however, not be more than 10, and usually not more than 5.

The above conditions are essential for the process according to the invention especially when they relate to $n_O^*:n_{Et}^*$, where $n_O^*$ is the total molar amount of molecular oxygen supplied to reaction zone A within a period t, and $n_{Et}^*$ is the total molar amount of ethanol supplied as a constituent of reaction gas input mixture A to reaction zone A within the same period t.

An excess of molecular oxygen over ethanol reactant viewed over reaction zone A is found to be advantageous for the process according to the invention, both for the service life of the catalyst charge of reaction zone A and for the service life of the catalyst charge of reaction zone B, since this excess molecular oxygen is introduced into reaction gas input mixture B in the process according to the invention.

In this document, an inert diluent gas shall be understood to mean a reaction gas input mixture constituent which behaves inertly under the conditions in the particular reaction zone A or B and—viewing each inert reaction gas constituent alone—remains chemically unchanged in the particular reaction zone to an extent of more than 95 mol %, preferably to an extent of more than 97 mol %, or to an extent or more than 98 mol %, or to an extent of more than 99 mol %. The above definition also applies correspondingly to inert diluent gases in reaction gas input mixture C and with reference to reaction zone C, which will be introduced later in this document.

Examples of inert diluent gases both for reaction zone A and reaction zones B and C are $H_2O$, $CO_2$, $N_2$ and noble gases such as Ar, and mixtures of the aforementioned gases. One task assumed by the inert diluent gases is that of absorbing heat of reaction released in the reaction zone A, thus limiting what is called the hotspot temperature in reaction zone A and having a favorable effect on the ignition behavior of reaction gas mixture A. The hotspot temperature is understood to mean the highest temperature of reaction gas mixture A on its way through reaction zone A.

Steam as an inert diluent gas in the two reaction zones A and B assumes a special role compared to other possible inert diluent gases. This is attributable to the fact that presence of steam in reaction gas input mixture A in reaction zone A facilitates the desorption of the desired partial oxidation product from the catalyst surface, which has a positive effect on the selectivity of acetic acid formation. In addition, steam has an increased molar heat capacity compared, for example, to $N_2$ and noble gases.

Advantageously in accordance with the invention, reaction gas input mixture A may therefore comprise 1 to 40% by volume of $H_2O$, Since presence of steam in reaction zone B, however, generally reduces the desired aldol condensation to a certain extent and also increases the energy expenditure required to remove a stream X comprising enriched acrylic acid from product gas mixture B in separation zone T (acrylic acid has an elevated affinity for $H_2O$), steam contents of 1 to 20% by volume in reaction gas input mixture A are preferred in accordance with the invention. This also takes account of the fact that $H_2O$ is formed as a by-product both in reaction zone A and in reaction zone B. Particularly advantageously in accordance with the invention, the steam content in reaction gas input mixture A will be 5 to 15% by volume or 7.5 to 12.5% by volume.

The inert diluent gas other than steam used in the process according to the invention, both in reaction zone A and in reaction zone B, is preferably molecular nitrogen. This is favorable not least in that molecular nitrogen occurs in air as a natural companion of molecular oxygen, which makes air a preferred source of the molecular oxygen required in reaction zone A. It will be appreciated, however, that it is also possible in accordance with the invention to use pure molecular oxygen, or air enriched with molecular oxygen, or another gas mixture of molecular oxygen and inert diluent gas, as the oxygen source.

Advantageously in accordance with the invention, at least 80% by volume, preferably at least 90% by volume, frequently at least 95% by volume and sometimes 100% by volume of the inert diluent gas other than steam present in reaction gas input mixture A is accounted for by molecular nitrogen. The same also applies to the inert gas ratios in reaction gas input mixture B. In general, reaction gas input mixture A comprises, as well as an inert diluent gas other than steam, additionally steam as an inert diluent gas. Normally, the content of inert diluent gases other than steam in reaction gas input mixture A will be at least 5% by volume, but generally not more than 95% by volume. Typical contents of inert diluent gas other than steam in reaction gas input mixture A are 10 to 90% by volume, preferably 30 to 90% by volume, more preferably 50 to 90% by volume and even more preferably 60 to 90% by volume, or 70 to 90% by volume, in particular 75 to 85% by volume.

Thus, the molecular nitrogen content in reaction gas input mixture A may be at least 5% by volume, preferably at least 10% by volume, more preferably at least 20 or at least 30% by volume or at least 40% by volume, but generally not more than 95% by volume. Typical molecular nitrogen contents in reaction gas input mixture A may be 10 to 90% by volume, preferably 30 to 90% by volume, more preferably 50 to 90% by volume and even more preferably 60 to 90% by volume, or 70 to 90% by volume, in particular 75 to 85% by volume.

The boiling point of the inert diluent gases other than steam (based on a pressure of $10^5$ Pa=1 bar) is normally distinctly below that of steam (based on the same pressure), and stream Z in the process according to the invention therefore comprises the inert diluent gases other than steam (e.g. $N_2$ and $CO_2$) generally in enriched form.

As a source for inert diluent gas other than steam, it is therefore appropriate in application terms also to recycle a substream of stream Z into reaction zone A for configuration of reaction gas input mixture A (cycle gas mode). Advantageously in application terms, the separation of product gas mixture B in separation zone T will be performed such that stream Z also has an appropriate content of steam and therefore, in the case of use of the above-described cycle gas mode, can also function as a source for steam which is advantageously used in addition in reaction gas input mixture A (or C). It will be appreciated that substreams of stream Z can be recycled not only into reaction zone A but also into reaction zone B (and C).

The temperature of reaction gas mixture A (the term "reaction gas mixture A" in the present application comprises all gas mixtures which occur in reaction zone A and are between reaction gas input mixture A and product gas mixture A; in an entirely corresponding manner, the term "reaction gas mixture B" comprises all gas mixtures which occur in reaction zone B and are between reaction gas input mixture B and product gas mixture B) in the process according to the invention within reaction zone A will normally be within the range from 100° C. to 450° C., preferably within the range from 150° C. to 400° C. and more preferably within the range from 150° C. to 350° C. or 150° C. to 300° C. The aforementioned temperature range may of course also be 200° C. to 300° C. The term "temperature of reaction gas mixture A" (also referred to in this document as the reaction temperature in reaction zone A) means primarily that temperature that reaction gas mixture A has on attainment of a conversion of the ethanol present in reaction gas input mixture A of at least 5 mol % until attainment of the corresponding final conversion of the ethanol within reaction zone A.

Advantageously in accordance with the invention, the temperature of reaction gas mixture A over the entire reaction zone A is within the aforementioned temperature ranges. Advantageously, reaction gas input mixture A is also supplied to reaction zone A already with a temperature within the range from 100° C. to 350° C. Frequently, however, at the inlet into reaction zone A, upstream of the actual catalytically active catalyst charge of reaction zone A in flow direction, there is a charge of reaction zone A with solid inert material, or of catalytically active catalyst charge highly diluted with such inert material. In the course of flow through such an upstream charge of reaction zone A, the temperature of reaction gas input mixture A supplied to reaction zone A can be adjusted in a comparatively simple manner to the value with which reaction gas mixture A should enter the actual catalytically active catalyst charge of reaction zone A. In principle, the charge of reaction zone A with at least one oxidation catalyst A can be configured as a fluidized bed. Advantageously in application terms, the charge of reaction zone A with oxidation catalyst A is, however, configured as a fixed bed.

In principle, reaction gas mixture A can be either forced through or sucked through reaction zone A. Accordingly, the working pressure (=absolute pressure) within reaction zone A may be either $\geq 10^5$ Pa or $<10^5$ Pa. Appropriately in application terms, the working pressure in reaction zone A will be $\geq 10^5$ Pa. In general, the working pressure in reaction zone A will be in the range from $1.2 \cdot 10^5$ Pa to $50 \cdot 10^5$ Pa, preferably in the range from $1.5 \cdot 10^5$ to $20 \cdot 10^5$ Pa and more preferably in the range from $2 \cdot 10^5$ to $10^6$ Pa or in the range from $2 \cdot 10^5$ to $6 \cdot 10^5$ Pa.

The configuration of reaction zone A can, appropriately in application terms, be undertaken in the form of what is called a "heat exchanger reactor". The latter has at least one primary space and at least one secondary space, which are separated from one another by a dividing wall. The catalyst charge positioned in the at least one primary space comprises at least one oxidation catalyst A, and reaction gas mixture A flows through it. At the same time, a fluid heat carrier flows through the secondary space and heat exchange takes place between the two spaces through the dividing wall, which pursues the purpose of monitoring and controlling the temperature of reaction gas mixture A on its way through the catalyst bed (of controlling the temperature of reaction zone A).

Examples of heat exchanger reactors suitable in accordance with the invention for the implementation of reaction zone A are the tube bundle reactor (as disclosed, for example, in EP-A 700714 and the prior art cited in that document) and the thermoplate reactor (as disclosed, for example, in documents EP-A 1651344, DE-A 10361456, DE-A 102004017150 and the prior art acknowledged in these documents). In the case of the tube bundle reactor, the catalyst bed through which reaction gas mixture A flows is preferably within the tubes thereof (the primary spaces), and at least one heat carrier is conducted through the space surrounding the reaction tubes (the secondary space). Useful heat carriers for the heat exchanger reactors are, for example, salt melts, heat carrier oils, ionic liquids and steam. In general, tube bundle reactors used on the industrial scale comprise at least 3000 up to several tens of thousands of reaction tubes connected in parallel (reactor tubes). It will be appreciated that the configuration of reaction zone A can also be implemented in a fluidized bed reactor or a microreactor.

Conventional reactors and microreactors differ by their characteristic dimensions and especially by the characteristic dimensions of the reaction space which accommodates the catalyst bed through which the reaction gas mixture flows.

The inventive partial oxidation of ethanol to acetic acid proceeds in two successive steps. In the first step the ethanol is partially oxidized to acetaldehyde, and in the second step (which follows the first) the acetaldehyde is partially oxidized to acetic acid.

It has now been found that, surprisingly, it is advantageous for the target product formation in reaction zone A to use, for the second reaction step, oxidation catalysts A whose active materials, as well as a vanadium oxide, also comprise a molybdenum oxide. In other words, for the second step of the partial oxidation of ethanol to acetic acid, it is advantageous in accordance with the invention to use multimetal oxide catalysts A whose active materials, as well as oxygen, also comprise at least the elements Mo and V.

Oxidation catalysts of this type are known from the literature as catalysts for the heterogeneously catalyzed partial gas phase oxidation of acrolein to acrylic acid. It has now been found that, surprisingly, all multimetal oxide catalysts of the aforementioned type which are known from the prior art as catalysts for the heterogeneously catalyzed partial gas phase oxidation of acrolein to acrylic acid are also advantageously suitable as oxidation catalysts for the second step of the partial oxidation of ethanol to acetic acid, the partial oxidation of acetaldehyde to acetic acid, in reaction zone A.

Such multimetal oxide active materials comprising Mo and V, including the catalysts comprising them, can be found, for example, in documents U.S. Pat. No. 3,775,474, U.S. Pat. No. 3,954,855, U.S. Pat. No. 3,893,951, U.S. Pat. No. 4,339,355, EP-A 614872, EP-A 1041062, WO 03/055835 and WO 03/057653.

Especially suitable for the second step in reaction zone A of the present invention are, however, also the multimetal oxide active materials comprising Mo and V, including the catalysts comprising them, as disclosed in documents DE-A 10325487, DE-A 10325488, EP-A 427508, DE-A 2909671, DE-C 3151805, DE-B 2626887, DE-A 4302991, EP-A 700893, EP-A 714700, DE-A 19736105, DE-A 19927624, DE-A 102010028328 and DE-A 10360057. This is especially true of the exemplary embodiments of EP-A 714700, of DE-A 19736105, of DE-A 19927624, of DE-A 10360057 and of DE-A 102010028328.

Particularly suitable for the relevant second reaction step in reaction zone A are those oxidation catalysts A whose active material is at least one multimetal oxide which, as well as V and Mo, additionally comprises at least one of the elements W, Nb, Ta, Cr and Ce, and at least one of the elements Cu, Ni, Co, Fe, Mn and Zn.

Suitable among these for catalysis of the second step of the partial oxidation of ethanol to acetic acid are in particular multimetal oxide active materials of the general formula I

$$Mo_{12}V_aX^1_bX^2_cX^3_dX^4_eX^5_fX^6_gO_n \qquad (I),$$

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=1 to 6,
b=0.2 to 4,
c=0.5 to 1.8,
d=0 to 40,
e=0 to 2,
f=0 to 4,
g=0 to 40, and
n=the stoichiometric coefficient of the element oxygen, which is determined by the stoichiometric coefficients of the non-oxygen elements and the charge numbers thereof in I.

In embodiments very particularly preferred in accordance with the invention, the variables of the general formula I are each defined as follows:
$X^1$=W, Nb and/or Cr,
$X^2$=Cu, Ni, Co, Fe, Mn and/or Fe,
$X^3$=Sb,
$X^4$=Na and/or K,
$X^5$=Ca, Sr and/or Ba,
$X^6$=Si, Al and/or Ti,
a=1.5 to 5,
b=0.5 to 2,
c=0.5 to 3,
d=0 to 2,
e=0 to 0.2,
f=0 to 1,
g=0 to 1, and
n=the stoichiometric coefficient of the element oxygen, which is determined by the stoichiometric coefficients of the non-oxygen elements and the charge numbers thereof in I.

The multimetal oxide active materials comprising V and Mo, especially those of the general formula I, can be used either in powder form or shaped to particular catalyst geometries as unsupported catalysts for catalysis of the partial oxidation of acetaldehyde to acetic acid. With regard to the catalyst geometries suitable in accordance with the invention, the statements already made in this document with regard to the possible geometries of unsupported oxidation catalysts A apply correspondingly.

Preferably in accordance with the invention, the described multimetal oxide active materials comprising V and Mo are, however, employed in the form of eggshell catalysts (i.e. applied to the outer surface of preshaped inert catalyst supports (shaped support bodies)) in the catalysis of the relevant second reaction step. With regard to the geometries of the shaped support bodies suitable in accordance with the invention, the statements already made in this document in connection with eggshell oxidation catalysts A apply correspondingly. Preferred geometries of the shaped support bodies here too are spheres and rings, the longest dimension of which may be 1 to 10 mm, frequently 2 to 8 mm or 3 to 6 mm. The ring geometries favorable in accordance with the invention are hollow cylindrical shaped support bodies having a length of 2 to 10 mm, an external diameter of 4 to 10 mm and a wall thickness of 1 to 4 mm. The hollow cylindrical shaped support bodies preferably have a length of 3 to 6 mm, an external diameter of 4 to 8 mm and a wall thickness of 1 to 2 mm. An illustrative geometry is the 7 mm×3 mm×4 mm ring geometry (external diameter×length×internal diameter). The thickness of the eggshell of catalytically active oxide material applied to the shaped support bodies in the aforementioned eggshell catalysts is, appropriately in application terms, generally 10 to 1000 μm. This eggshell thickness is preferably 10 to 500

μm, more preferably 100 to 500 μm and most preferably 200 to 300 μm. Advantageously, the eggshell thickness is very substantially homogeneous viewed over a single eggshell catalyst. In the case of production of a relatively large production batch of the eggshell catalysts, the eggshell thickness is likewise very substantially homogeneous viewed over several shaped eggshell catalyst bodies. Useful materials for the inert shaped support bodies include the inert materials already mentioned in this document. Such possible insert materials once again include aluminum oxide, silicon dioxide, silicates such as clay, kaolin, steatite, pumice, aluminum silicate and magnesium silicate, silicon carbide, zirconium dioxide and thorium dioxide (an inert material particularly preferred in accordance with the invention for shaped support bodies is steatite of the C 220 type from CeramTec). Shaped support bodies with distinct surface roughness (for example hollow cylinders with a grit layer as described in Research Disclosure Database Number 532036 (published August 2008)) are preferred for production of the shaped eggshell catalyst bodies. Otherwise, the shaped support bodies are preferably very substantially nonporous.

To produce the shaped eggshell catalyst bodies, the catalytically active oxide material of the general formula I can first be prepared as such. This is typically done by obtaining, from sources of the elemental constituents of the catalytically active oxide material, a very intimate, preferably finely divided, dry mixture with a composition corresponding to the stoichiometry thereof (a precursor material), and calcining (thermally treating) it at temperatures of 350 to 600° C. The calcinations can be effected either under inert gas or under an oxidizing atmosphere, for example air (or another mixture of inert gas and oxygen), or else under reducing atmosphere (for example mixtures of inert gas and reducing gases such as $H_2$, $NH_3$, CO, methane and/or acrolein, or any of the reducing gases mentioned alone). The calcination time may be a few minutes to a few hours and typically decreases with the level of the calcination temperature. A calcination process of good suitability in accordance with the invention is described, for example, by WO 95/11081.

Useful sources for the elemental constituents of the catalytically active oxide material of the general formula I include (as is generally the case for oxidation catalysts A), especially those compounds which are already oxides and/or those compounds which can be converted to oxides by heating, at least in the presence of oxygen. The starting compounds (sources) can be intimately mixed in dry or wet form. When it is done in dry form, the starting compounds are appropriately used in the form of fine powders and, after mixing and optional compaction, subjected to calcination. However, preference is given to effecting the intimate mixing in wet form. Typically, this involves mixing the starting compounds with one another in the form of an aqueous solution and/or suspension.

Particularly intimate dry mixtures are obtained in the mixing process described when the starting materials are exclusively sources of the elemental constituents present in dissolved form.

The solvent used is preferably water. Subsequently, the liquid (e.g. aqueous) material obtained is dried, the drying operation preferably being effected by spray-drying the liquid (e.g. aqueous) mixture with exit temperatures of 100 to 150° C. Appropriately in application terms, the drying gas stream is air or molecular nitrogen.

The catalytically active oxide material obtained after calcining is subsequently converted to a fine powder, for example by grinding, which can then normally be applied to the outer surface of the shaped support body with the aid of a liquid binder. The fineness of the catalytically active oxide material to be applied to the surface of the shaped support body is of course adjusted to the desired eggshell thickness as described in the prior art (cf., for example, EP-A 714700).

For example, the shaped support bodies are moistened with the liquid binder in a controlled manner, for example by spraying, and the thus moistened shaped support bodies are dusted with the finely divided catalytically active oxide material (cf., for example, EP-A 714 700 and DE-A102010023312). Subsequently, the adhering liquid is at least partly removed from the moistened shaped support body coated with active oxide material (for example passage of hot gas; cf. WO 2006/094766). However, it is also possible to use all other application processes acknowledged as prior art in EP-A 714700 for production of eggshell catalysts suitable in accordance with the invention with multimetal oxide I active materials. Examples of useful liquid binders include water and aqueous solutions.

in principle, however, the procedure for production of inventive eggshell catalysts may also be first to apply finely divided precursor material to the surface of the support body and to perform the calcination of the precursor material to the catalytically active oxide material of the general formula I only subsequently, i.e. already on the surface of the shaped support body.

Useful element sources for the preparation of catalytically active oxide materials of the general formula I include, as well as the element oxides, quite generally in particular halides, nitrates, formates, oxalates, acetates, carbonates and hydroxides. Appropriately in application terms, the molybdenum source used is ammonium heptamolybdate tetrahydrate. The preferred vanadium source is ammonium metavanadate and, in the case of additional use of the element W, ammonium paratungstate hydrate is the preferred element source. Useful sources for the elemental constituent Cu include, for the preparation of catalytically active oxide materials of the general formula I, especially copper(II) sulfate pentahydrate, copper(II) nitrate hydrate (Cu content=21.6% by weight) and copper(II) acetate monohydrate, among which the latter is preferred. The process for thermal treatment of the precursor material of a catalytically active oxide material of the general formula I will, advantageously in accordance with the invention, be performed according to the procedure described and executed by way of example in DE-A 10360057. In the case of annular shaped support bodies, the preferred process for applying catalytically active oxide material of the general formula I to the surface thereof is the process described in EP-A 714700. An aqueous solution of 75% by weight of water and 25% by weight of glycerol is then the preferred binder. Otherwise, the procedure may be as described in working examples 1 and 2 of DE-A 10360057. In the case of spherical shaped support bodies, water is the preferred binder.

When at least one oxidation catalyst A whose active material is a multimetal oxide (e.g. one of the general formula I) which, as well as oxygen, also comprises at least the elements Mo and V is used in the process according to the invention in reaction zone A for the second step of the heterogeneously catalyzed partial oxidation of ethanol to acetic acid, it is advantageous in accordance with the invention to use, for the first step of the partial oxidation of ethanol to acetic acid, at least one oxidation catalyst A whose active material is a mixed oxide which, as well as oxygen and V, also comprises at least one of the elements Ti (preferable), Zr and Al (and generally no Mo) (i.e. at least one oxidation catalyst A which comprises, in addition to a vanadium oxide (preferably $V_2O_5$), also at least one oxide of Ti (preferable: preferably $TiO_2$), Zr and Al).

Such a charge of reaction zone A with oxidation catalyst A is advantageous in accordance with the invention in that it ensures particularly high target product selectivities for acetic acid at high conversions of ethanol based on a single pass of reaction gas mixture A through reaction zone A.

In other words, advantageously in accordance with the invention, the charge of reaction zone A with at least one oxidation catalyst A comprises two sections 1 and 2 which are spatially successive (in the numerical sequence mentioned) in flow direction of reaction gas mixture A (between the two there may optionally be a section charged only with inert shaped bodies, which, however, is less preferred in accordance with the invention).

The active material of the at least one oxidation catalyst A of section 1 (in section 1), which is also referred to here as catalytically active material 1, is at least one mixed oxide which, as well as oxygen and V, also comprises at least one of the elements Ti (preferable), Zr and Al (and generally no Mo), while the active material of the at least one oxidation catalyst A of section 2 (in section 2), which is also referred to here as catalytically active material 2 (and is different than catalytically active material 1), is at least one mixed oxide comprising the elements V and Mo (preferably one of the general formula I). In other words, the at least one oxidation catalyst A of section 1 (the first section in flow direction of reaction gas mixture A) comprises, as well as a vanadium oxide (preferably $V_2O_5$), also at least one oxide of Ti (preferable: preferably $TiO_2$), Zr and Al (and generally no oxide of Mo), whereas the at least one oxidation catalyst A of section 2, as well as a vanadium oxide, also comprises at least one molybdenum oxide.

More preferably, the active material of the at least one oxidation catalyst A of section 1 comprises or consists of 1 to 50% by weight of $V_2O_5$ and 50 to 99% by weight of $TiO_2$, advantageously 3 to 40% by weight of $V_2O_5$ and 60 to 97% by weight of $TiO_2$, and very particularly advantageously 5 to 30% by weight of $V_2O_5$ and 70 to 95% by weight of $TiO_2$. The $TiO_2$ in the aforementioned cases is preferably in the anatase polymorph.

Advantageously in accordance with the invention, the temperature of section 1 is controlled independently of the temperature of section 2. Advantageously in application terms, the temperatures of sections 1 and 2 are controlled such that the temperature of reaction gas mixture A averaged arithmetically over the length of the (catalytically active) section 1 (this is the temperature $T^1$, which is also referred to in this document as the reaction temperature in section 1 averaged arithmetically over the length of section 1) is 150 to 250° C. and preferably 170 to 220° C., whereas the temperature of reaction gas mixture A averaged arithmetically over the length of the (catalytically active) section 2 (this is the temperature $T^2$ which is also referred to in this document as the reaction temperature of section 2 averaged over the length of section 2) is, appropriately in application terms, 180 to 260° C., preferably 200 to 240° C. and particularly advantageously 210 to 230° C.

Advantageously, $T^2$ is at least 5° C., preferably at least 10° C., more preferably at least 15° C. or at least 20° C. and most preferably at least 25° C. or at least 30° C. greater than $T^1$. In general, $T^2$ is, however, not more than 80° C. and frequently not more than 60° C. greater than $T^1$.

The length of the two charge sections 1 and 2 is, in accordance with the invention, normally such that the conversion of ethanol achieved in a single pass of reaction gas mixture A through section 1 is at least 90 mol %, regularly even at least 95 mol %, and the conversion of acetaldehyde achieved in section 2 is likewise at least 90 mol % and regularly even at least 95 mol %. The conversion of ethanol achieved in a single pass of reaction gas mixture A through sections 1 and 2 is regularly ≧97 mol %, in many cases ≧98 mol % and frequently ≧99 mol %. The selectivity of the associated acetic acid formation is normally ≧85 mol %, frequently ≧86 mol % or ≧87 mol % and in many cases even ≧88 mol % or ≧90 mol %.

The implementation of the two sections 1 and 2 of reaction zone A is possible in a simple manner, for example in two heat exchanger reactors connected in series (for example two tube bundle reactors), through whose particular secondary spaces an independent fluid heat carrier flows in each case. The at least one primary space of the first of the two reactors in flow direction accommodates section 1, while the at least one primary space of the second of the two reactors in flow direction accommodates section 2.

The two sections 1 and 2 of reaction zone A can, for example, also be implemented in what is called a two-zone reactor, as disclosed by way of example in DE-A 2830765. In this case, the two sections 1 and 2 are accommodated in spatial succession in the same primary space, and the secondary space adjoining the primary space is divided into two subspaces, one of which extends over section 1 and the other over section 2, through both of which separately flow heat carriers having different inlet temperatures. Two-zone reactors are also covered by documents DE-A 10313210, DE-A 10313209, DE-A 19948523, DE-A 19948523, DE-A 19948241, DE-A 10313208 and WO 2007/082827. Preferably in accordance with the invention, two-zone tube bundle reactors are employed.

When the two sections 1 and 2 are implemented in a two-zone reactor, reaction gas input mixture A must already have (comprise) all constituents required for the partial oxidation of ethanol to acetic acid to the extent required for the reaction. When they are implemented in two heat exchanger reactors connected in series, it is also possible, for example, to meter molecular oxygen and/or inert gas to reaction gas mixture A between the two reactors.

Advantageously in accordance with the invention, oxidation catalysts A whose active material comprises at least one vanadium oxide (including those of the general formula I), in the case of use for the heterogeneously catalyzed partial oxidation of ethanol to acetic acid, have a completely satisfactory service life even when reaction gas input mixture A is produced using bioethanol, i.e. ethanol which is obtained from the renewable base raw material biomass. As a result of production, bioethanol generally comprises at least one chemical compound comprising the element sulfur in chemically bound form as an impurity. Based on the weight of the ethanol present in bioethanol and expressed via the weight of the sulfur present in such sulfur compounds, the content in bioethanol of such sulfur compounds is generally ≧1 ppm by weight, frequently ≧2 ppm or ≧3 ppm by weight. In general, the aforementioned sulfur content in bioethanol is ≦200 ppm by weight, or ≦150 ppm by weight or in some cases ≦100 ppm by weight.

Examples of sulfur-comprising impurities of this kind include dimethyl sulfate and dimethyl sulfoxide. The content of sulfur compounds can be determined by gas chromatography. Remarkably, oxidation catalysts A whose active material comprises at least one vanadium oxide are apparently substantially resistant to such sulfur compounds as a constituent of reaction gas input mixture A, and so corresponding contents of sulfur compounds based on the ethanol content of reaction gas input mixture A can be tolerated in reaction gas input mixture A in the process according to the invention. It will be appreciated, however, that bioethanol with a corresponding content of sulfur compounds which has been lowered to values of <1 ppm by weight is also suitable as the ethanol source for the process according to the invention.

For example, for the process according to the invention, it is possible to use bioethanol which satisfies the following specification:

| | | |
|---|---|---|
| Ethanol | >99.8% by volume | DIN 12803 |
| Water | <1500 ppm | DIN EN ISO 12937 |
| Methanol | <100 ppm | GC |
| Sum of $C_3$- to $C_5$-alcohols | <1500 ppm | GC |
| Esters, calculated as ethyl acetate | <250 ppm | GC |
| Aldehydes, calculated as acetaldehyde | <250 ppm | GC |
| Acetone | <10 ppm | GC |
| Neutralization number | <0.028 mg KOH/g | ASTM D 1613-03 |
| Acid number, calculated as acetic acid | <50 ppm | ASTM D 1613 |
| Chlorine-comprising compounds as Cl | <0.5 ppm | ASTM 4929 B |
| Sulfur-comprising compounds as S | <1 ppm | DIN EN ISO 11885 (E22) |
| Iron-comprising constituents as Fe | <0.1 ppm | DIN EN ISO 11885 (E22) |
| Nitrogen-comprising compounds as N | 0 ppm | ASTM D 1614-03 |

It is essential to the invention that sulfur present in chemically bound form in corresponding impurities present in reaction gas input mixture A is introduced into reaction zone B as a constituent of reaction gas input mixture B in the process according to the invention. It is surprising that the aldol condensation catalysts for use in accordance with the invention in reaction zone B, especially those preferred in accordance with the invention, have a completely satisfactory tolerance to compounds comprising sulfur in chemically bound form.

To obtain reaction gas input mixture A, bioethanol used as a raw material is converted as such to the vapor phase and introduced into reaction gas input mixture A. It will be appreciated that it is also possible in this way to use aqueous bioethanol solutions in the process according to the invention. In principle, the ethanol source used for the process according to the invention may also be aqueous slurry which comprises bioethanol in dissolved form and is obtained in bioethanol production. This is subjected to filtration and solids present therein are filtered off. The filtrate is converted to the vapor phase and sent to the production of reaction gas input mixture A.

Otherwise, the space velocity on the fixed catalyst bed which is present in reaction zone A and comprises at least one oxidation catalyst A of ethanol present in reaction gas input mixture A in the process according to the invention may, for example, be 20 to 500, preferably 30 to 100 and more preferably 50 to 100 l (STP)/l·h. The term "space velocity" is used as defined in DE-A 19927624.

Useful sources for the formaldehyde required in reaction gas input mixture B for the process according to the invention include various raw materials. One possible source is aqueous solutions of formaldehyde (cf., for example, DE-A 102008059701) which can be purchased commercially as formalin, for example with a formaldehyde content of 35 to 50% by weight (e.g. 49-2015 formaldehyde from BASF SE). Typically, formalin also comprises small amounts of methanol as a stabilizer. These may, based on the weight of the formalin, be 0.5 to 20% by weight, advantageously 0.5 to 5% by weight and preferably 0.5 to 2% by weight. Converted to the vapor phase, the formalin can be used directly to produce reaction gas input mixture B. However, a disadvantage of formalin as the formaldehyde source is that it also comprises water as well as formaldehyde, which has an unfavorable effect on the position of the reaction equilibrium in reaction zone B.

A useful alternative formaldehyde source is trioxane. Trioxane is a heterocyclic compound from the group of the acetals, which forms as a result of trimerization of formaldehyde. It is solid at standard pressure ($10^5$ Pa) at 25° C., melts at 62° C. and boils at 115° C. When heated to 150 to 200° C., it depolymerizes again to form monomeric formaldehyde. Since the reaction temperature in reaction zone B is normally above 250° C., trioxane is thus a formaldehyde source favorable in accordance with the invention for production of reaction gas input mixture B. Since trioxane also has comparatively good solubility in water and in alcohols such as methanol, it is also possible to use corresponding trioxane solutions as the formaldehyde source suitable in accordance with the invention for the process according to the invention. Presence of 0.25 to 0.50% by weight of sulfuric acid in trioxane solutions promotes redissociation to formaldehyde. Alternatively, the trioxane can also be dissolved in a liquid stream Y consisting principally of acetic acid, and the resulting solution can be evaporated for the purposes of producing reaction gas input mixture B, and the trioxane present therein can be redissociated to formaldehyde at the elevated temperature.

In addition, the formaldehyde source used for the process according to the invention may be paraformaldehyde. Paraformaldehyde is the short-chain polymer of formaldehyde, the degree of polymerization of which is typically 8 to 100. This is a white powder which is dissociated back to formaldehyde at low pH values or when heated.

It decomposes when paraformaldehyde is heated in water to obtain an aqueous formaldehyde solution which is likewise a source suitable in accordance with the invention. It is sometimes referred to as aqueous "paraformaldehyde solution" in order to delimit it for terminology purposes from aqueous formaldehyde solutions which are obtained by diluting formalin. In fact, paraformaldehyde as such is, however, essentially insoluble in water.

A further formaldehyde source suitable for the process according to the invention is methylal (dimethoxymethane). This is a reaction product of formaldehyde with methanol, which forms a colorless liquid at standard pressure to 25° C. It is hydrolyzed in aqueous acids to again form formaldehyde and methanol. Converted to the vapor phase, it is suitable for production of reaction gas input mixture B.

It is also possible to employ the processes disclosed in Chemie Ingenieur Technik-CIT, Volume 66, Issue 4, pages 498 to 502, Published Online 2004 for continuous metered addition of formaldehyde.

On the industrial scale, formaldehyde is prepared by heterogeneously catalyzed partial gas phase oxidation of methanol. A formaldehyde source particularly preferred in accordance with the invention for formation of reaction gas input mixture B is therefore the product gas mixture of a heterogeneously catalyzed partial gas phase oxidation of methanol to formaldehyde, optionally after a portion or the entirety of any unconverted methanol present therein has been removed.

Reaction gas input mixture B can be produced from the stream of product gas mixture A leaving reaction zone A and the formaldehyde source which has been converted to the vapor phase as at least one further stream, and stream Y and optionally further streams, for example additional steam or additional inert gas other than steam (=inert diluent gas).

The temperature of reaction gas mixture B in the process according to the invention within reaction zone B will normally be within the range from 260 to 400° C., preferably within the range from 270 to 390° C., more preferably within the range of 280 to 380° C., advantageously within the range of 300 to 370° C. and particularly advantageously within the range of 300 to 340° C.

The term "temperature of reaction gas mixture B" (also referred to in this document as reaction temperature in reaction zone B) means primarily that temperature that reaction gas mixture B has from attainment of a conversion of the formaldehyde present in reaction gas input mixture B of at least 5 mol % until attainment of the appropriate final conversion of the formaldehyde within reaction zone B. Advantageously in accordance with the invention, the temperature of reaction gas mixture B over the entire reaction zone B is within the aforementioned temperature ranges. Advantageously, reaction gas input mixture B is already supplied to reaction zone B with a temperature within the range from 260 to 400° C. Frequently, however, a charge of reaction zone B with solid inert material or of catalytically active catalyst charge highly diluted with such inert material is present at the inlet into reaction zone B in flow direction upstream of the actual catalytically active catalyst charge of reaction zone B. As it flows through such a primary charge of reaction zone B, the temperature of the reaction gas input mixture B supplied to reaction zone B can be adjusted in a comparatively simple manner to the value with which reaction gas mixture B is to enter the actual catalytically active catalyst charge of reaction zone B. In general, the temperature of the product gas mixture A leaving reaction zone A is different than this temperature. Against this background, the stream of product gas mixture A, on its way from reaction zone A into reaction zone B, can flow through an indirect heat exchanger in order to approximate its temperature to the inlet temperature envisaged for reaction gas input mixture B into reaction zone B, or to bring it to this temperature.

In principle, the charge of reaction zone B with at least one aldol condensation catalyst B can be configured as a fluidized bed. Advantageously in application terms, the charge of reaction zone B with aldol condensation catalyst B is, however, configured as a fixed bed.

With regard to the working pressure which exists in reaction zone B, the same applies correspondingly as has already been stated for the working pressure which exists in reaction zone A. In general, the working pressure in reaction zone B, due to the pressure drop which occurs as reaction gas mixture A flows through reaction zone A, is lower than the working pressure in reaction zone B. It is also possible to configure reaction zone B in corresponding heat exchanger reactors to reaction zone A, in which case the same rules of preference apply.

The formaldehyde content in reaction gas input mixture B will, in the process according to the invention, generally be 0.5 to 10% by volume, preferably 0.5 to 7% by volume and more preferably 1 to 5% by volume.

The ratio $n_{HAc}:n_{Fd}$ of molar amount of acetic acid present in reaction gas input mixture B ($n_{HAc}$) to molar amount of formaldehyde present therein ($n_{Fd}$) in the process according to the invention is greater than 1 and may be up to 10 ($n_{Fd}$ is understood to mean the sum of formaldehyde units present in monomeric form (preferred) and in oligomeric and polymeric form in reaction gas input mixture B, since further redissociation to monomeric formaldehyde can also be established only in the course of flow of reaction gas mixture B through the catalyst charge of reaction zone B). Advantageously in accordance with the invention, the ratio $n_{HAc}:n_{Fd}$ in reaction gas input mixture B is 1.1 to 5 and more preferably 1.5 to 3.5.

Frequently, the acetic acid content of reaction gas input mixture B will vary within the range from 1 or from 1.5 to 20% by volume, advantageously within the range from 2 to 15% by volume and particularly advantageously within the range from 3 to 10% by volume. The molecular oxygen content of reaction gas input mixture B varies, in the process according to the invention, appropriately in application terms, within the range from 0.5 to 5% by volume, preferably within the range from 1 to 5% by volume and more preferably within the range from 2 or from 3 to 5% by volume. Presence of molecular oxygen in reaction gas input mixture B has an advantageous effect on the service life of the catalyst charge of reaction zone B. When the oxygen content of reaction gas mixture B is too high, however, there is unwanted carbon oxide formation in reaction zone B.

The steam content of reaction gas input mixture B in the process according to the invention should not exceed 30% by volume since presence of steam in reaction gas mixture B has an unfavorable effect on the equilibrium position of the aldol condensation. Appropriately in application terms, the steam content of reaction gas input mixture B will therefore generally not exceed 25% by volume and preferably 20% by volume. In general, the steam content of reaction gas input mixture B will be at least 1.5% or at least 2% by volume. Advantageously, the steam content of reaction gas input mixture B is 5 to 15% by volume and, taking account of the effect thereof and formation thereof in reaction zone A, in particular 10 to 15% by volume. The proportion by volume of inert diluent gases other than steam in reaction gas input mixture B will normally be at least 30% by volume. Preferably, the aforementioned inert gas content is at least 40% by volume or at least 50% by volume. In general, the proportion of inert diluent gas other than steam in reaction gas input mixture B will not exceed 95% by volume or usually 90% by volume. Particularly advantageously in application terms, reaction gas input mixture B comprises 60 to 90% by volume, particularly advantageously 70 to 80% by volume, of inert diluent gas other than steam. An inert diluent gas other than steam which is preferred in accordance with the invention is, in reaction gas input mixture B2, molecular nitrogen ($N_2$).

Thus, the molecular nitrogen content of reaction gas input mixture B may be at least 30% by volume, preferably at least 40% by volume or at least 50% by volume. In general, reaction gas input mixture B comprises not more than 95% by volume and usually not more than 90% by volume of molecular nitrogen. Advantageously, reaction gas input mixture B comprises 60 to 90% by volume, particularly advantageously 70 to 80% by volume, of molecular nitrogen.

Useful catalysts for charging of reaction zone B include, for example, those disclosed in I & EC PRODUCT RESEARCH AND DEVELOPMENT, vol. 5, No. 1, March 1966, pages 50 to 53. This group of basic catalysts comprises firstly zeolites (aluminosilicates) with anionic structural charge, on the inner and outer surfaces of which at least one cation type from the group of the alkali metal ions and alkaline earth metal ions is present (preferably $Na^+$, $K^+$, $Ca^{2+}$ and/or $Mg^{2+}$), in order to balance out (to neutralize) the negative structural charge. However, it also comprises hydroxide applied to inert supports (e.g. amorphous silicon dioxide (silica gel)), from the group consisting of alkali metal hydroxides, alkaline earth metal hydroxides and aluminum hydroxide (preferably KOH, NaOH, $Ca(OH)_2$ and $Mg(OH)_2$).

However, also suitable for charging reaction zone B are the acidic catalysts disclosed in EP-A 164614.

These are catalysts which comprise as constituent a), at least one oxide of at least one of the elements Si, Al, Ti, Zr, Cd, Sn, Ga, Y and La and/or zeolite, and as constituent b), at least one oxide selected from boron oxide and phosphorus oxide, and optionally as constituent c) one or more than one oxide of at least one of the elements V, Cr, Co, Ni, Mo and Pb and/or one or more than one heteropolyacid with at least one poly atom selected from V, Mo and W.

Preferred boron oxide is $B_2O_3$, and preferred phosphorus oxide is $P_2O_5$.

Preference is given to catalysts whose boron oxide content (calculated as $B_2O_3$ (based on the amount of B present)) is 1 to 50% by weight. However, catalysts favorable in accordance with the invention are also those whose phosphorus oxide content (calculated as $P_2O_5$ (based on the amount of P present)) is 1 to 50% by weight. However, useful aldol condensation catalysts B for the process according to the invention also include those among the aforementioned catalysts whose total content of phosphorus oxide (calculated as $P_2O_5$) and of boron oxide (calculated as $B_2O_3$) is 1 to 50% by weight. The aforementioned contents of phosphorus oxide and/or boron oxide are preferably 5 to 30% by weight.

In addition, constituent a) is preferably at least one oxide of at least one of the elements Si, Al, Ti and Zr.

Particularly favorable in accordance with the invention are the combinations of titanium oxide as constituent a) and boron oxide or phosphorus oxide as constituent b), or silicon dioxide-aluminum oxide as constituent a) and boron oxide as constituent b), or aluminum oxide as constituent a) and boron oxide or phosphorus oxide as constituent b). When the catalysts detailed above additionally comprise a heteropolyacid, it preferably comprises at least one of the elements P, B and Si as heteroatom. When the aforementioned catalysts comprise a constituent c), the amount thereof is normally 0.01 to 10 mmol per gram of catalyst and in many cases 0.03 to 5 mmol per gram of catalyst. It is favorable when the catalysts have, as constituent c), both at least one of the oxides and at least one of the heteropolyacids.

More preferably in accordance with the invention, reaction zone B is, however, charged with aldol condensation catalysts B whose active material is a vanadium-phosphorus oxide and/or a vanadium-phosphorus oxide doped with elements other than vanadium and phosphorus (also referred to collectively in the literature as V-P-O catalysts).

Such catalysts have been described before in the literature and are recommended there especially as catalysts for the heterogeneously catalyzed partial gas phase oxidation of hydrocarbons having at least four carbon atoms (especially n-butane, n-butene and/or benzene) to maleic anhydride.

Surprisingly, these catalysts known from the prior art for aforementioned partial oxidations are suitable in principle as aldol condensation catalysts B for charging reaction zone B. They are notable for particularly high selectivities of target product formation (of acrylic acid formation) (with simultaneously high formaldehyde conversions).

Accordingly, the aldol condensation catalysts B used in the process according to the invention may, for example, be all of those disclosed in documents U.S. Pat. No. 5,275,996, U.S. Pat. No. 5,641,722, U.S. Pat. No. 5,137,860, U.S. Pat. No. 5,095,125, DE-69702728 T2, WO 2007/012620, WO 2010/072721, WO 2001/68245, U.S. Pat. No. 4,933,312, WO 2003/078310, Journal of Catalysis 107, pages 201-208 (1987), DE-A 102008040094, WO 97/12674, "Neuartige Vanadium (IV)-phosphate für die Partialoxidation von kurzkettigen Kohlenwasserstoffen-Synthesen, Kristallstrukturen, Redox-Verhalten and katalytische Eigenschaften [Novel vanadium(IV) phosphates for the partial oxidation of short-chain hydrocarbon syntheses, crystal structures, Redox behavior and catalytic properties], thesis by Ernst Benser, 2007, Rheinische Friedrichs-Wilhelms-Universität Bonn", WO 2010/072723, "Untersuchung von V-P-O-Katalysatoren für die partielle Oxidation von Propan zu Acrylsäure [Study of V-P-O catalysts for the partial oxidation of propane to acrylic acid], thesis by Thomas Quandt, 1999, Ruhr-Universität Bochum", WO 2010/000720, WO 2008/152079, WO 2008/087116, DE-A 102008040093, DE-A 102005035978 and DE-A 102007005602, and the prior art acknowledged in these documents. In particular, this applies to all exemplary embodiments of the above prior art, especially those of WO 2007/012620.

The phosphorus/vanadium atomic ratio in the undoped or doped vanadium-phosphorus oxides is, advantageously in accordance with the invention, 0.9 to 2.0, preferably 0.9 to 1.5, more preferably 0.9 to 1.2 and most preferably 1.0 to 1.1. The arithmetic mean oxidation state of the vanadium therein is preferably +3.9 to +4.4 and more preferably 4.0 to 4.3. These active materials also advantageously have a specific BET surface area of $\geq 15$ m²/g, preferably of $\geq 15$ to 50 m²/g and most preferably of $\geq 15$ to 40 m²/g. They advantageously have a total pore volume of $\geq 0.1$ ml/g, preferably of 0.15 to 0.5 ml/g and most preferably of 0.15 to 0.4 ml/g. Total pore volume data in this document relate to determinations by the method of mercury porosimetry using the Auto Pore 9220 test instrument from Micromeritics GmbH, DE-4040 Neuss (range from 30 Å to 0.3 mm). As already stated, the vanadium-phosphorus oxide active materials may be doped with promoter elements other than vanadium and phosphorus. Useful such promoter elements include the elements of groups 1 to 15 of the Periodic Table other than P and V. Doped vanadium-phosphorus oxides are disclosed, for example, by WO 97/12674, WO 95/26817, U.S. Pat. No. 5,137,860, U.S. Pat. No. 5,296,436, U.S. Pat. No. 5,158,923, U.S. Pat. No. 4,795,818 and WO 2007/012620.

Promoters preferred in accordance with the invention are the elements lithium, potassium, sodium, rubidium, cesium, thallium, molybdenum, zinc, hafnium, zirconium, titanium, chromium, manganese, nickel, copper, iron, boron, silicon, tin, niobium, cobalt and bismuth, among which preference is given not only to iron but especially to niobium, molybdenum, zinc and bismuth. The vanadium-phosphorus oxide active materials may comprise one or more promoter elements. The total content of promoters in the catalytic active material is, based on the weight thereof, generally not more than 5% by weight (the individual promoter element calculated in each case as the electrically uncharged oxide in which the promoter element has the same charge number (oxidation number) as in the active material).

Useful active materials for aldol condensation catalysts B for charging reaction zone B are thus especially multielement oxide active materials of the general formula II

(II)

in which the variables are each defined as follows:

$X^1$=Mo, Bi, Co, Ni, Si, Zn, Hf, Zr, Ti, Cr, Mn, Cu, B, Sn and/or Nb, preferably Nb, Mo, Zn and/or Hf, $X^2$=Li, K, Na, Rb, Cs and/or Tl, b=0.9 to 2.0, preferably 0.9 to 1.5, more preferably 0.9 to 1.2 and most preferably 1.0 to 1.1, c=≧0 to 0.1,
d=≧0 to 0.1,
e=≧0 to 0.1, and
n=the stoichiometric coefficient of the element oxygen, which is determined by the stoichiometric coefficients of the non-oxygen elements and the charge numbers thereof in II.

Irrespective of the stoichiometric coefficients d, e and b, the stoichiometric coefficient C is, advantageously in accordance with the invention, in active materials of the general formula II, 0.005 to 0.1, preferably 0.005 to 0.05 and particularly advantageously, 0.005 to 0.02.

The aldol condensation catalysts B may comprise the multimetal oxide active materials of the general formula II, for example, in pure, undiluted form, or diluted with an oxidic, essentially inert dilution material in the form of unsupported catalysts. Inert dilution materials suitable in accordance with the invention include, for example, finely divided aluminum oxide, silicon dioxide, aluminosilicates, zirconium dioxide, titanium dioxide or mixtures thereof. Undiluted unsupported catalysts are preferred in accordance with the invention. The unsupported catalysts may in principle be of any shape. Preferred shaped unsupported catalyst bodies are spheres, solid cylinders, hollow cylinders and trilobes, the longest dimension of which in all cases is advantageously 1 to 10 mm.

In the case of shaped unsupported catalyst bodies, the shaping is advantageously effected with precursor powder which is calcined only after the shaping. The shaping is effected typically with addition of shaping assistants, for example graphite (lubricant) or mineral fibers (reinforcing aids). Suitable shaping processes are tableting and extrusion.

The external diameter of cylindrical unsupported catalysts is, appropriately in application terms, 3 to 10 mm, preferably 4 to 8 mm and in particular 5 to 7 mm. The height thereof is advantageously 1 to 10 mm, preferably 2 to 6 mm and in particular 3 to 5 mm. The same applies in the case of hollow cylinders. In addition, the internal diameter of the orifice running through from the top downward is advantageously 1 to 8 mm, preferably 2 to 6 mm and most preferably 2 to 4 mm. A wall thickness of 1 to 3 mm is appropriate in application terms in the case of hollow cylinders. It will be appreciated that the doped or undoped vanadium-phosphorus oxide active material can also be used in powder form, or as eggshell catalysts with an active material eggshell applied to the surface of inert shaped support bodies, as aldol condensation catalysts B in reaction zone B. The preparation of the eggshell catalysts, the eggshell thickness and the geometry of the inert shaped support bodies may be selected as described in the case of the eggshell catalysts for reaction zone A.

Otherwise, doped or undoped vanadium-phosphorus oxide active materials and unsupported catalysts manufactured therefrom can be produced as described in the documents of the prior art, to which reference is made in this patent application.

These are especially the documents WO 2007/012620, WO 2010/07273, WO 2010/000720 and WO 2010/000764.

For example, the procedure may be as follows:
a) reaction of a pentavalent vanadium compound (e.g. $V_2O_5$) with an organic reducing solvent (e.g. isobutanol) in the presence of a pentavalent phosphorus compound (e.g. ortho- and/or pyrophosphoric acid) with heating to 75 to 205° C., preferably to 100 to 120° C.;
b) cooling of the reaction mixture to advantageously 4 to 90° C.;
c) optional addition of compounds comprising doping elements, for example iron(III) phosphate;
d) reheating to 75 to 205° C., preferably 100 to 120° C.;
e) isolation of the solid precursor material formed, comprising V, P, O and, for example, Fe (for example by filtering);
f) drying and/or thermal pretreatment of the precursor material (optionally until commencement of performing by elimination of water from the precursor material);
g) addition of shaping assistants, for example finely divided graphite or mineral fibers, and subsequent shaping to give the shaped unsupported catalyst precursor body by, for example, tableting;
h) subsequent thermal treatment of the shaped catalyst precursor bodies formed by heating in an atmosphere which comprises oxygen, nitrogen, noble gases, carbon dioxide, carbon monoxide and/or steam (for example as described in WO 2003/078310 at page 20, line 16 to page 21, line 35). The temperature of the thermal treatment generally exceeds 250° C., in many cases 300° C. or 350° C., but normally not 600° C., preferably not 550° C. and most preferably not 500° C.

The space velocity on the catalyst charge of reaction zone B of formaldehyde present in reaction gas input mixture B may, in accordance with the invention, be for example 1 to 100, preferably 2 to 50 and more preferably 3 to 30 or 4 to 10 l (STP)/l·h. The term "space velocity" is used as defined in DE-A 19927624. Both in reaction zone A and in reaction zone B, the particular fixed catalyst bed (including the case of a section 1/section 2 division in reaction zone A) may consist only of catalysts comprising active material, or else of a mixture of catalysts comprising active material and inert shaped bodies.

Especially in the case of use of V-P-O catalysts as aldol condensation catalysts in reaction zone B, in the process according to the invention, based on a single pass of reaction gas mixture B through reaction zone B, at least 95 mol %, usually at least 98 mol %, of the formaldehyde present in reaction gas input mixture B is converted. The selectivity of acrylic acid formation, based on formaldehyde converted, is generally ≧95 mol %, frequently ≧98 mol %.

Suitable in accordance with the invention for configuration of reaction zone B are those heat exchanger reactors which have already been recommended for implementation of reaction zone A.

As already mentioned, formaldehyde is prepared on the industrial scale by heterogeneously catalyzed partial gas phase oxidation of methanol. A formaldehyde source which is particularly preferred in accordance with the invention for formation of reaction gas input mixture B is therefore the product gas mixture of a heterogeneously catalyzed partial gas phase oxidation of methanol to formaldehyde.

Appropriately in application terms, the process according to the invention therefore comprises a further, third reaction zone C which is charged with at least one oxidation catalyst C and advantageously comprises the following additional measures:
  a stream of a reaction gas input mixture C comprising the methanol and molecular oxygen reactants and at least one inert diluent gas other than steam is passed through a third reaction zone C charged with at least one oxidation catalyst C and methanol present in reaction gas input mixture C, as it passes through reaction zone C, is oxidized under heterogeneous catalysis to formaldehyde and steam, so as to form a product gas mixture C comprising formaldehyde, steam, and at least one inert diluent gas other than steam, and a stream of product gas mixture C leaves reaction zone C, it optionally being possible to add further molecular oxygen and/or further inert diluent gas to reaction gas mixture C flowing through reaction zone C on its way through reaction zone C.

The formaldehyde-comprising stream of product gas mixture C leaving reaction zone C can then be used as such (i.e. without performing a removal process thereon beforehand) in order to obtain reaction gas input mixture B. In general, for this purpose, product gas mixture C will first be cooled (quenched) on leaving reaction zone C, in order to reduce undesired further reactions in product gas mixture C before introducing it into reaction gas input mixture B. Typically, it will be cooled very rapidly to temperatures of 150 to 350° C., or 200 to 250° C.

Optionally, however, it is also possible first to remove, in a separation zone T*, a portion or the entirety of any methanol which is still present in product gas mixture C and has not been converted in reaction zone C therefrom, and then to use the remaining formaldehyde-comprising product gas mixture C* (which can pass through the liquid state in the course of removal) to obtain reaction gas input mixture B. Advantageously in application terms, the removal will be undertaken by rectificative means. For this purpose, product gas mixture C, optionally after preceding direct or indirect cooling, can be supplied in gaseous form to the appropriate rectification column provided with cooling circuit. It is of course, however, possible first to convert, from product gas mixture C, those constituents whose boiling point at standard pressure ($10^5$ Pa) is less than or equal to the boiling point of formaldehyde to the liquid phase (for example by condensation) and to undertake the rectification from the liquid phase. In general, such a methanol removal is also accompanied by a removal of steam present in product gas mixture C. For the purpose of the aforementioned direct cooling, it is possible, for example, to use liquid phase which has been withdrawn from the bottom region of the rectification column and optionally additionally cooled by indirect heat exchange, which is sprayed by means of appropriate nozzles into fine droplets which provide the large heat exchange area required for the hot product gas mixture C. The methanol removed will, appropriately in accordance with the invention, be recycled into reaction zone C and used to obtain reaction gas input mixture C (cf. DE-A 1618413). A removal of methanol from product gas mixture C prior to the use thereof to obtain reaction gas input mixture B is generally undertaken when reaction zone C is configured such that the resulting conversion of methanol in reaction zone C, based on a single pass of product gas mixture C through reaction zone C, is not more than 90 mol %. It will be appreciated that such a methanol removal can, however, also be employed in the case of corresponding methanol conversions of not more than 95 mol %. For example, such a methanol removal can be undertaken as described in Ullmann's Encyclopedia of Industrial Chemistry, vol. A11, 5th Ed., VCH Weinheim on pages 626 ff.

The oxidation catalysts C which are particularly suitable for charging reaction zone C can be divided essentially into two groups.

The first of the two groups comprises what are called the silver catalysts, which have, as the active material, elemental silver whose purity is preferably 99.7% by weight, advantageously $\geq$99.8% by weight, preferably $\geq$99.9% by weight and most preferably $\geq$99.99% by weight. The corresponding processes for heterogeneously catalyzed partial gas phase oxidation of methanol to formaldehyde over these "silver catalysts" are described in the prior art as silver processes (cf., for example, "A. Nagy, G. Mestl: High temperature partial oxidation reactions over silver catalysts, Appl. Catal. 188 (1999), p. 337 to 353", "H. Schubert, U. Tegtmayr, R. Schlögl: On the mechanism of the selective oxidation of methanol over elemental silver, Catalyst Letters, 28 (1994), p. 383 to 395", "L. Lefferts, Factors controlling the selectivity of silver catalysts for methanol oxidation, thesis, University of Twente (1987)" and DE-A 2334981).

Silver oxidation catalysts C advantageous in accordance with the invention for charging of reaction zone C are disclosed, for example, in Ullmann's Encyclopedia of Industrial Chemistry, vol. A11, 5th ed., VCH, Weinheim, p. 619 to 652, or in Encyclopedia of Chemical Technology, vol. 11, 4th ed., Wiley & Sons, New York, p. 929 to 949, in DE-B 1231229, in DE-B 1294360, in DE-A 1903197 and in BE patent 683130. Typically, these comprise crystals (the shape of which may also be round) of elemental silver (preferably of the abovementioned purity) which have been deposited by electrolysis of aqueous silver salt solutions and which can be poured as a fixed catalyst bed onto a perforated base (for example a perforated plate, a sieve or a mesh network (preferably likewise manufactured from silver)) (typical bed heights are 10 to 50 mm, frequently 15 to 30 mm). The total content of metals present in elemental form other than silver in the catalytically active silver (e.g. Cu, Pd, Pb, Bi, Fe, Pt and Au) is advantageously $\leq$2000 ppm by weight, better $\leq$1000 ppm by weight, preferably $\leq$100 ppm by weight and more preferably $\leq$50 ppm by weight or $\leq$30 ppm by weight. The longest dimension of the silver crystals is typically in the range from 0.1 to 5 mm and preferably increases in flow direction of reaction gas mixture C. The fixed silver bed is preferably configured as a two-layer bed, in which case the lower layer has a thickness, for example, of 15 to 40 mm, preferably 20 to 30 mm, and consists to an extent of at least 50% by weight of silver crystals of particle size 1 to 4 mm, preferably 1 to 2.5 mm. The upper layer may have, for example, a thickness (layer thickness) of 0.75 to 3 mm, preferably 1 to 2 mm, and consist of crystals having particle sizes (longest dimensions) of 0.1 to 1 mm, preferably 0.2 to 0.75 mm. In this case, reaction gas input mixture C flows in from the top downward.

In order to counteract sintering of the silver crystals with increasing operating time (at comparatively high reaction temperatures), which reduces the performance of the fixed catalyst bed, WO 2010/022923 recommends coating the silver crystals with a thin porous layer of oxidic material of at least one of the elements Al, Si, Zr and Ti (the layer thickness may be 0.3 to 10 µm, preferably 1.0 to 5.0 µm, more preferably 2.0 to 4.0 µm and at best about 3 µm), and in this way achieving prolonging of the service life of the fixed catalyst bed.

The methanol content in reaction gas input mixture C is, in the silver process, normally at least 5% by volume, usually at least 10% by volume, and may extend up to 60% by volume. The aforementioned methanol content in the silver process is preferably 15 to 50% by volume and more preferably 20 to 40 or to 30% by volume.

In addition, the ratio of the molar amount of molecular oxygen present in reaction gas input mixture C ($n_O$) to the molar amount of methanol present in reaction gas input mixture C ($n_{Me}$), $n_O$:$n_{Me}$, in the silver process is normally less than 1 (<1), preferably $\leq$0.8. It will more preferably be 0.2 to 0.6 and most preferably 0.3 to 0.5 or 0.4 to 0.5. In general, $n_O$:$n_{Me}$ in the silver process will not be less than 0.1.

The statements made for the inert diluent gases for reaction zone A essentially also apply to reaction zone C in the case of the silver process. Examples of inert diluent gases usable in reaction gas input mixture C in the case of the silver process are $H_2O$, $CO_2$, $N_2$ and noble gases such as Ar, and mixtures of the aforementioned gases.

A preferred inert diluent gas other than steam in the case of the silver process is molecular nitrogen for reaction gas input mixture C too. The advantage thereof is based not least on the fact that molecular nitrogen occurs in air as a natural companion of molecular oxygen, which makes air a preferred source of the molecular oxygen required in reaction zone C. It will be appreciated that, in the case of the silver process, it is, however, also possible in accordance with the invention to use pure molecular oxygen, or air enriched with molecular oxygen, or another mixture of molecular oxygen and inert diluent gas, as the oxygen source.

Typically, reaction gas input mixture C comprises, in the case of the silver process, 20 to 80% by volume, or 30 to 70% by volume, or 40 to 60% by volume, of inert diluent gas. The latter may be entirely free of steam. In other words, reaction gas input mixture C in the case of the silver process may comprise 20 to 80% by volume, or 30 to 70% by volume, or 40 to 60% by volume, of molecular nitrogen. For similar reasons to those for reaction gas input mixture A, however, in the case of the silver process, steam is generally also used as an inert diluent gas in reaction gas input mixture C.

In principle, reaction gas input mixture C in the case of the silver process may comprise >0 to 50% by volume of $H_2O$. For comparable reasons to those in the case of reaction gas input mixture A, it is, however, advantageous in accordance with the invention to comparatively restrict the $H_2O$ content of reaction gas input mixture C in the case of the silver process.

In other words, reaction gas input mixture C preferably comprises, in the case of the silver process, $\geq 5$ to 45% by volume of $H_2O$, advantageously $\geq 10$ to 40% by volume and particularly advantageously 15 to 35% by volume or 20 to 30% by volume of $H_2O$. The inert gas source used in the case of the silver process, for reaction gas input mixture C too, may be the stream Z obtained in separation zone T. Appropriately in application terms, in the case of the silver process, a substream of stream Z will therefore be recycled into reaction zone C to obtain reaction gas input mixture C.

In other words, reaction gas input mixtures C suitable in accordance with the invention may, in the case of the silver process, comprise, for example, 10 to 50% by volume of $H_2O$ and 20 to 60% by volume of inert diluent gas other than steam (e.g. $N_2$, or $N_2+CO_2$, or $N_2$+noble gas (e.g. Ar), or $N_2+CO_2$+ noble gas (e.g. Ar).

It will be appreciated that reaction gas input mixtures C, in the case of the silver process, may also comprise 10 to 40% by volume of $H_2O$ and 30 to 60% by volume of inert diluent gases other than steam (for example those mentioned above).

Of course, reaction gas input mixture C, in the case of the silver process, may also comprise 20 to 40% by volume of $H_2O$ and 30 to 50% by volume of inert diluent gases other than steam (for example those mentioned above).

In principle, in the case of the silver process, reaction gas mixture C can be even forced or sucked through reaction zone C. Accordingly, the working pressure in the case of the silver process within reaction zone C may be either $\geq 10^5$ Pa or $<10^5$ Pa. Appropriately in application terms, the working pressure in the case of the silver process in reaction zone C will be $10^3$ to $10^6$ Pa, preferably $10^4$ to $5\cdot 10^5$ Pa, more preferably $10^4$ to $2\cdot 10^5$ Pa and most preferably $0.5\cdot 10^5$ Pa to $1.8\cdot 10^5$ Pa.

The temperature of reaction gas mixture C (the term "reaction gas mixture C" comprises, in the present application, all gas mixtures which occur in reaction zone C and are between reaction gas input mixture C and product gas mixture C) will, in the case of the silver process, within reaction zone C, normally be within the range from 400 to 800° C., preferably within the range from 450 to 800° C. and more preferably within the range from 500 to 800° C. The term "temperature of reaction gas mixture C" (also referred to in this document as reaction temperature in reaction zone C) means primarily that temperature which reaction gas mixture C has from attainment of a conversion of the methanol present in reaction gas input mixture C of at least 5 mol % until attainment of the corresponding final conversion of the methanol within reaction zone C.

Advantageously in accordance with the invention, the temperature of reaction gas input mixture C in the case of the silver process is within the aforementioned temperature ranges over the entire reaction zone C.

Advantageously, in the case of the silver process, reaction gas input mixture C is also supplied to reaction zone C already with a temperature within the aforementioned range. Frequently, in the case of the silver process, a charge of reaction zone C with solid inert material or of catalytically active catalyst charge highly diluted with such inert material is present at the inlet into reaction zone C upstream in flow direction of the actual catalytically active catalyst charge (which may also be diluted with inert shaped bodies). As it flows through such an upstream charge of reaction zone C, the temperature of the reaction gas input mixture C supplied to reaction zone C in the case of the silver process can be adjusted comparatively easily to the value with which reaction gas mixture C in the case of the silver process is to enter the actual catalytically active catalyst charge of reaction zone C.

When the temperature of reaction gas mixture C in the case of the silver process within reaction zone C is limited to values of 450 to 650° C., preferably 500 to 600° C., the conversion of methanol will generally be $\leq 90$ mol %, frequently $\leq 85$ mol % or $\leq 80$ mol %, while the selectivity of formaldehyde formation will be at values of $\geq 90$ mol %, in many cases $\geq 93$ mol % or $\geq 95$ mol %. In this case (in which the steam content of the reaction gas input mixture is preferably <10% by volume), it is appropriate in accordance with the invention, from product gas mixture C, to remove at least a portion of unconverted methanol prior to the use thereof for obtaining reaction gas input mixture B, and to recycle it into the production of reaction gas input mixture C.

Advantageously in accordance with the invention, the temperature of reaction gas mixture C in the case of the silver process within reaction zone C will therefore be 550 to 800° C., preferably 600 to 750° C. and more preferably 650 to 750° C.

At the same time, the steam content of reaction gas input mixture C in the case of the silver process is advantageously adjusted to values of $\geq 10\%$ by volume, preferably $\geq 15\%$ by volume and particularly advantageously $\geq 20\%$ by volume. Both the elevated temperature and the elevated steam content of reaction gas input mixture C, in the case of the silver process, have an advantageous effect on the methanol conversion (based on a single pass of reaction gas mixture C through reaction zone C). In general, this conversion will be >90 mol %, in many cases $\geq 92$ mol %, or $\geq 95$ mol % and frequently even $\geq 97$ mol % (cf., for example, Ullmann's Encyclopedia of Industrial Chemistry, vol. A 11, 5th ed., VCH Weinheim on pages 625 ff.) (the high methanol conversions which are to be achieved in the case of the silver process in spite of the comparatively low $n_O:n_{Me}$ ratios in reaction gas input mixture C are attributable in particular to the fact that, with increasing temperature of reaction gas mixture C in reaction zone C, the exothermic partial oxidation $CH_3OH + 0.5 \rightarrow O_2 \rightarrow HCHO+H_2O$ is increasingly accompanied by the endothermic dehydrogenation $CH_3OH \leftrightarrows HCHO+H_2$). In this way, in the case of the silver process, it is regularly possible to achieve yields of formaldehyde of ≧85 mol %, usually ≧87 mol % and in many cases ≧89 mol % based on a single pass of reaction gas mixture C through reaction zone C and the molar amount of methanol converted. Otherwise, the silver process can be performed as described in the prior art documents already mentioned in this regard, or as described in documents U.S. Pat. No. 4,080,383, U.S. Pat. No. 3,994,977, U.S. Pat. No. 3,987,107, U.S. Pat. No. 4,584,412 and U.S. Pat. No. 4,343,954. It will be appreciated that, in the case of the silver process described, it is possible not only to use comparatively pure methanol as the raw material (source). Methanol raw materials suitable in accordance with the invention in this regard are also aqueous methanol solutions and technical-grade methanol, which can be used after appropriate evaporation to obtain reaction gas input mixture C.

Suitable reactors for execution of the silver process in reaction zone C include not only those recommended in the aforementioned prior art but also those heat exchanger reactors which have already been recommended for implementation of reaction zone A. The space velocity of methanol present in reaction gas input mixture C on the reactor charged with silver crystals will generally be $(0.5$ to $6) \cdot 10^3$ kg of methanol per $m^2$ of reactor cross section or cross section of the fixed catalyst bed.

Preferably in accordance with the invention, the heterogeneously catalyzed partial gas phase oxidation of methanol to formaldehyde will, however, be performed by the FORMOX process.

In contrast to the silver process, the FORMOX process is performed over oxidation catalysts C whose active material is a mixed oxide which has at least one transition metal in the oxidized state (cf., for example, WO 03/053556 and EP-A 2213370). The term "transition metals" means the chemical elements of the Periodic Table with atomic numbers 21 to 30, 39 to 48 and 57 to 80.

Preferably in accordance with the invention, aforementioned mixed oxide active materials comprise at least one of the transition metals Mo and V in the oxidized state. Most preferably in accordance with the invention, the aforementioned active materials are mixed oxides having at least one of the elements Fe and Mo in the oxidized state (cf., for example, U.S. Pat. No. 3,983,073, U.S. Pat. No. 3,978,136, U.S. Pat. No. 3,975,302, U.S. Pat. No. 3,846,341, U.S. Pat. No. 3,716,497, U.S. Pat. No. 4,829,042, EP-A 2213370 and WO 2005/063375, U.S. Pat. No. 3,408,309, U.S. Pat. No. 3,198,753, U.S. Pat. No. 3,152,997, WO 2009/1489809, DE-A 2145851, WO 2010/034480, WO 2007/059974 and "Methanol Selective Oxidation to Formaldehyde over Iron-Molybdate Catalysts, Ana Paula Vieira Soares and Manuel Farinha Portela and Alain Kiennemann in Catalysis Review 47, pages 125 to 174 (2004)" and the prior art cited in these documents).

A further difference between the silver process and the FORMOX process is that the ratio of the molar amount of molecular oxygen present in reaction gas input mixture C ($n_O$) to the molar amount of methanol present in reaction gas input mixture C ($n_{Me}$), $n_O:n_{Me}$, is normally at least 1 or greater than 1 (≧1), preferably 1.1. In general, the $n_O:n_{Me}$ ratio in reaction gas input mixture C in the FORMOX process will, however, be not more than 5, frequently not more than 4. $n_O:n_{Me}$ ratios which are advantageous in accordance with the invention in reaction gas input mixture C are 1.5 to 3.5, preferably 2 to 3. In addition, the methanol content of reaction gas input mixture C in the FORMOX process will typically be not more than 15% by volume, usually not more than 11% by volume. This is because gas mixtures of molecular nitrogen, molecular oxygen and methanol with a molecular oxygen content of not more than approx. 11% by volume of molecular oxygen are outside the explosion range. Normally, the methanol content in reaction gas input mixture C in the case of the FORMOX process will be ≧2% by volume, preferably 4 to 10% by volume and more preferably 6 to 9% by volume or 5 to 7% by volume. Gas mixtures of molecular nitrogen, molecular oxygen and methanol whose methanol content is ≦6.7% by volume are, irrespective of the molecular oxygen content therein, outside the explosion range, which is why particularly high $n_O:n_{Me}$ ratios in reaction gas input mixture C can be employed within this concentration range.

However, the FORMOX process also differs from the silver process in that the methanol conversions achieved by this process, based on a single pass of reaction gas mixture C through reaction zone C, essentially irrespective of the inert diluent gas used in reaction gas input mixture C, are regularly >90 mol %, typically ≧92 mol %, usually ≧95 mol % and in many cases even ≧97 mol % or ≧98 mol %, or ≧99 mol %. The accompanying selectivities of formaldehyde formation are regularly ≧90 mol %, usually ≧92 mol % and in many cases ≧94 mol %, and frequently even ≧96 mol %.

According to the invention, useful inert diluent gases in reaction gas input mixture C for the FORMOX process in reaction zone C are likewise gases such as $H_2O$, $N_2$, $CO_2$ and noble gases such as Ar, and mixtures of aforementioned gases. A preferred inert diluent gas other than steam in the case of the FORMOX process too in reaction gas input mixture C is molecular nitrogen.

The inert diluent gas content (the definition of an inert diluent gas for reaction zone C is analogous to that for reaction zones A and B) in reaction gas input mixture C may, in the case of the FORMOX process, be 70 to 95% by volume, frequently 70 to 90% by volume and advantageously 70 to 85% by volume. In other words, the molecular nitrogen content of reaction gas input mixture C may, in the case of employment of the FORMOX process, in reaction gas input mixture C, be 70 to 95% by volume, or 70 to 90% by volume, or 70 to 85% by volume. Advantageously in accordance with the invention, reaction gas input mixture C in the case of the FORMOX process may be free of steam. Appropriately in application terms, reaction gas input mixture C, in the case of employment of a FORMOX process in reaction zone C, may have a low steam content for the same reasons as in the case of reaction gas input mixture A. In general, the steam content of reaction gas input mixture C in the FORMOX process in reaction zone C is ≧0.1% by volume and ≦20% by volume or ≦10% by volume, advantageously ≧0.2% by volume and ≦7% by volume, preferably ≧0.5% by volume and ≦5% by volume.

A further advantage of the employment of a FORMOX process in reaction zone C, in accordance with the invention, results from the fact that the high methanol conversions described are established as significantly lower reaction temperatures compared to the use of a silver process.

The temperature of reaction gas mixture C in the case of the FORMOX process in reaction zone C will normally be in the range from 250 to 500° C., preferably in the range from 300 to 450° C. and frequently within the range from 270 to 400° C. The meaning of the term "temperature of reaction gas mixture C" corresponds in the case of the FORMOX process to that which has already been given in this document for the silver process.

Advantageously in accordance with the invention, the temperature of reaction gas mixture C (also referred to in this document as the reaction temperature in reaction zone C) in the case of the FORMOX process, over the entire reaction zone C, is within the aforementioned temperature ranges.

Advantageously, in the case of the FORMOX process too, reaction gas input mixture C is supplied to reaction zone C already with a temperature within the aforementioned range. Frequently, in the case of the FORMOX process, a charge of reaction zone C with solid inert material or of catalytically active catalyst charge highly diluted with such inert material is present at the inlet into reaction zone C upstream in flow direction of the actual catalytically active catalyst charge (which may also be diluted with inert shaped bodies). As it flows through such an upstream charge of reaction zone C, the temperature of reaction gas input mixture C supplied to reaction zone C in the FORMOX process can be adjusted in a comparatively simple manner to the value with which reaction gas mixture C in the FORMOX process is to enter the actual catalytically active catalyst charge.

With regard to the working pressure in reaction zone C, the statements made for the silver process apply correspondingly to the FORMOX process.

Mixed oxide active materials particularly suitable for the FORMOX process are those of the general formula III $$[Fe_2(MoO_4)_3]_1[M^1{}_mO_n]_q \qquad (III),$$

in which the variables are each defined as follows:
$M_1$=Mo and/or Fe, or
  Mo and/or Fe and, based on the total molar amount of Mo and Fe, a total molar amount of up to 10 mol % (e.g. 0.01 to 10 mol %, or 0.1 to 10 mol %), preferably not more than 5 mol %, of one or more elements from the group consisting of Ti, Sb, Sn, Ni, Cr, Ce, Al, Ca, Mg, V, Nb, Ag, Mn, Cu, Co, Si, Na, K, Tl, Zr, W, Ir, Ta, As, P and B,
q=0 to 5, or 0.5 to 3, or 1 to 2,
m=1 to 3, and
n=1 to 6,
with the proviso that the contents of both sets of square brackets are electrically uncharged, i.e. do not have any electrical charge.

Advantageously in accordance with the invention, mixed oxide active materials III comprise less than 50 mol %, more preferably less than 20 mol % and more preferably less than 10 mol % of the Fe present in the mixed oxide active material III in the +2 oxidation state, and the remaining amount of the Fe present therein in each case in the +3 oxidation state. Most preferably, the mixed oxide active material III comprises all of the Fe present therein in the +3 oxidation state.

The $n_{Mo}:n_{Fe}$ ratio of molar amount of Mo present in a mixed oxide active material III ($n_{Mo}$) to molar amount of Fe present in the same mixed oxide active material ($n_{Fe}$) is preferably 1:1 to 5:1.

In addition, it is advantageous in accordance with the invention when $M^1$=Mo and m=1 and n=3. Mixed oxide active materials advantageous in accordance with the invention also exist when $M^1$=Fe and m=2 and n=3.

Mixed oxide active materials III favorable in accordance with the invention are also those with such a stoichiometry that they can be considered (represented) in a formal sense as a mixture of $MoO_3$ and $Fe_2O_3$, and the $MoO_3$ content of the mixture is 65 to 95% by weight and the $Fe_2O_3$ content of the mixture 5 to 35% by weight.

Mixed oxide active materials III can be prepared as described in the prior art documents cited.

In general, the procedure will be to obtain, from sources of the catalytically active oxide material III, a very intimate, preferably finely divided, dry mixture of composition corresponding to the stoichiometry of the desired oxide material III (a precursor material), and calcining (thermally treating) it at temperatures of 300 to 600° C., preferably 400 to 550° C. The calcination can be performed either under inert gas or under an oxidative atmosphere, for example air (or another mixture of inert gas and oxygen), or else under a reducing atmosphere (for example a mixture of inert gas and reducing gases such as $NH_3$ and CO). The calcination time will generally be a few hours and typically decreases with the magnitude of the calcination temperature.

Useful sources for the elemental constituents of the mixed oxide active materials III are especially those compounds which are already oxides and/or those compounds which can be converted to oxides by heating, at least in the presence of oxygen. The intimate mixing of the starting compounds (sources) can be effected in dry or in wet form. Where it is effected in dry form, the starting compounds are appropriately used in the form of fine powders and, after mixing and optional compaction, subjected to calcination. However, preference is given to effecting the intimate mixing in wet form. In this case, the starting compounds are typically mixed with one another in the form of aqueous suspensions and/or solutions. Particularly intimate dry mixtures are obtained in the mixing process described when the starting materials are exclusively sources of the elemental constituents present in dissolved form.

The solvent used is preferably water. Preference is given to preparing, from the starting compounds, at least two aqueous solutions, at least one of which is an acidic solution and at least one of which an ammoniacal (basic) solution.

Combination of the aqueous solutions generally results in precipitation reactions in which precursor compounds of the multimetal oxide active material III form.

Subsequently, the aqueous material obtained is dry, and the drying operation can be effected, for example, by spray drying.

The catalytically active oxide material obtained after the calcining of the dry material can be used to charge reaction zone C for the FORMOX process in finely divided form as such, or applied with the aid of a liquid binder to an outer surface of a shaped support body in the form of an eggshell catalyst. However, eggshell catalysts can also be produced by applying, with the aid of a liquid binder, fine precursor powder to the outer surface of shaped support bodies, and calcining the precursor substance only after completion of application and drying.

The multimetal oxide active materials III can, however, also be used in reaction zone C in pure, undiluted form, or diluted with an oxidic, essentially inert diluent material, in the form of what are called unsupported catalysts (this is preferred in accordance with the invention). Examples of inert diluent materials suitable in accordance with the invention include finely divided aluminum oxide, silicon dioxide, aluminosilicates, zirconium dioxide, titanium dioxide or mixtures thereof. Undiluted unsupported catalysts are preferred in accordance with the invention.

In the case of shaped unsupported catalyst bodies, the shaping is advantageously effected with precursor powder which is not calcined until after the shaping. The shaping is effected typically with addition of shaping assistants, for example graphite (lubricant) or mineral fibers (reinforcing aid). Suitable shaping processes are tableting and extrusion. It will be appreciated that the shaping may, however, also be performed, for example, with a mixture of active material powder and precursor powder, to which shaping assistants and optionally inert diluent powders are again added prior to the shaping. Shaping is followed by another calcination. In principle, the shaping to unsupported catalysts can also be performed only with already prefabricated active material powder and optionally the aids mentioned. This procedure is less advantageous. The shaping here too is generally followed by another calcination.

A favorable Mo source is, for example, ammonium heptamolybdate tetrahydrate $(NH_4)_6$, $(Mo_7O_{24}) \cdot 4H_2O$. Advantageous iron sources are, for example, iron(III) nitrate [Fe$(NO_3)_3$], iron(III) chloride [$FeCl_3$] or hydrates of iron(III) nitrate, for example $Fe(NO_3)_3 \cdot 9\ H_2O$.

With regard to the geometries and materials suitable in accordance with the invention for the shaped support bodies and the coating processes for producing eggshell catalysts of the mixed oxide active materials III, the statements already made in this document in connection with eggshell oxidation catalysts A apply correspondingly. Preferred geometries of the shaped support bodies here too are spheres and rings, the longest dimension of which is 1 to 10 mm, frequently 2 to 8 mm or 3 to 6 mm. Ring geometries favorable in accordance with the invention have hollow cylindrical shaped support bodies with a length of 2 to 10 mm, an external diameter of 4 to 10 mm and a wall thickness of 1 to 4 mm. The hollow cylindrical shaped support bodies preferably have a length of 3 to 6 mm, an external diameter of 4 to 8 mm and a wall thickness of 1 to 2 mm.

The thickness of the eggshell of catalytically active oxide material applied to the shaped support bodies in the aforementioned eggshell catalysts is, in the case of the mixed oxide active materials III too, appropriately in application terms, generally 10 to 1000 μm. The eggshell thickness is preferably 10 to 500 μm, more preferably 100 to 500 μm and most preferably 200 to 300 μm.

Preferred shaped unsupported catalyst bodies comprising mixed oxide active materials III are solid cylinders, hollow cylinders and trilobes. The external diameter of cylindrical unsupported catalysts is, appropriately in application terms, 3 to 10 mm, preferably 4 to 8 mm and in particular 5 to 7 mm. The height thereof is advantageously 1 to 10 mm, preferably 2 to 6 mm and in particular 3 to 5 mm. The same applies in the case of hollow cylinders. In addition, the internal diameter of the orifice passing through from the top downward is advantageously 1 to 8 mm, preferably 2 to 6 mm and most preferably 2 to 4 mm. Appropriately in application terms, the wall thickness of hollow cylinders is 1 to 3 mm.

However, mixed oxide active material III oxidation catalysts C can also be employed in reaction zone C in the form of supported catalysts. In this case, the starting materials are comparatively porous shaped support bodies which, for example, are impregnated successively with the at least two solutions of the precursor compounds. The precipitation reaction described proceeds in the pores of the shaped support body, and the precursor compounds which form therein can subsequently be converted to the desired mixed oxide active material III by calcination. Alternatively, it is also possible to impregnate with a solution comprising all sources required in dissolved form, to dry and then to calcine (cf., for example, DE-A 2442311). Otherwise, the procedure for preparation of the mixed oxide active material III oxidation catalysts may be as in the prior art documents to which reference is made in this regard in this application.

These are especially documents U.S. Pat. No. 3,716,497, U.S. Pat. No. 3,846,341, EP-A 199359, DE-A 2145851, U.S. Pat. No. 3,983,073, DE-A 2533209, EP-A 2213370 and Catalysis Review, 47, pages 125-174 (2004).

It will be appreciated that, in the FORMOX process too, it is not only possible to use comparatively pure methanol to obtain reaction gas input mixture C. Methanol raw materials suitable in this regard in accordance with the invention are also aqueous methanol solutions and technical-grade methanol, which can be used after appropriate evaporation to obtain reaction gas input mixture C.

It is also possible to charge reaction zone C with a fixed catalyst bed which comprises FORMOX oxidation catalysts C in a form diluted with inert shaped bodies.

The space velocity on the fixed catalyst bed present in reaction zone C of reaction gas input mixture C will, in the case of a FORMOX process employed in accordance with the invention, generally be 3500 l (STP)/l·h to 75 000 l (STP)/l·h, preferably 25 000 l (STP)/l·h to 35 000 l (STP)/l·h. The term "space velocity" is used as defined in DE-A 19927624.

Suitable reactors for execution of the FORMOX process in reaction zone C are especially also the heat exchanger reactors which have already been recommended for implementation of reaction zone A (cf., for example, WO 2005/063375).

According to the invention, especially advantageous processes for preparing acrylic acid are those in which reaction gas input mixture B is obtained using, as the formaldehyde source, the product gas mixture C which leaves reaction zone C and is the product of a FORMOX process performed in reaction zone C. This is also because such a product gas mixture C, in contrast to a product gas mixture C after the silver process, is free of molecular hydrogen.

In other words, the product gas mixture C of a heterogeneously catalyzed partial gas phase oxidation of methanol to formaldehyde after the FORMOX process is (without subjecting it to a removal process beforehand, without performing a removal process thereon beforehand) the ideal formaldehyde source for formaldehyde required in reaction gas input mixture B.

Frequently, product gas mixture C is obtained in the FORMOX process with a temperature with which it can be used without further thermal pretreatment for production of reaction gas input mixture B. In many cases, the temperature of the product gas mixture C leaving reaction zone C, both in the case of the silver process and in the case of the FORMOX process, however, is different from that temperature with which it is to be used to obtain reaction gas input mixture B. Against this background, the stream of product gas mixture C, on its way from reaction zone C into reaction zone B, can flow through an indirect heat exchanger in order to match its temperature to the addition temperature envisaged for production of reaction gas input mixture B.

In principle, the charge of reaction zone C with at least one oxidation catalyst C can be configured as a fluidized bed. Advantageously in application terms, the charge of reaction zone C with oxidation catalyst C is, however, configured as a fixed bed.

For the sake of completeness, it should also be added that, in the case of employment of the FORMOX process in reaction zone C too, the stream Z obtained in separation zone T in the process according to the invention constitutes a suitable inert gas source for the inert gas required in reaction gas input mixture C and, appropriately in application terms, a substream of stream Z is recycled into reaction zone C to obtain reaction gas input mixture C.

The product gas mixture B which leaves reaction zone B and which comprises acrylic acid formed, unconverted acetic acid, at least one inert diluent gas other than steam, molecular oxygen and steam can be separated in a manner known per se into the at least three streams X, Y and Z in a separation zone T.

For example, the separation can be effected by fractional condensation, as recommended in documents DE-A 102007004960, DE-A 10 2007055086, DE-A 10243625, DE-A 10235847 and DE-A 19924532. In this procedure, the temperature of product gas mixture B is optionally first reduced by direct and/or indirect cooling, and product gas mixture B is then passed into a condensation column equipped with separating internals (for example mass transfer trays) and optionally provided with cooling circuits, and fractionally condensed ascending into itself within the condensation column. Appropriate selection of the number of theoretical plates in the condensation column allows streams X, Y and Z to be conducted out of the condensation column as separate fractions with the desired degree of enrichment in each case.

Appropriately in application terms, stream X is generally removed with an acrylic acid content of ≧90% by weight, preferably ≧95% by weight, and conducted out of the condensation column. In the event of an increased purity requirement, stream X can, advantageously in application terms, be purified further by crystallization (preferably suspension crystallization) (cf. the aforementioned prior art documents and WO 01/77056). It will be appreciated that the stream X conducted out of the condensation column can also be purified further by rectification. It is possible in both ways, with a comparatively low level of complexity, to achieve acrylic acid purities of ≧99.9% by weight, which are suitable for production of water-absorbing resins by free-radical polymerization of monomer mixtures comprising acrylic acid and/or the sodium salt thereof.

The water-absorbing resins can be prepared, for example, as described in documents WO 2008/116840, DE-A 102005062929, DE-A 102004057874, DE-A 102004057868, DE-A 102004004496 and DE-A 19854575.

In a corresponding manner, stream Y is normally also conducted out of the condensation column with an acetic acid content of ≧90% by weight, preferably ≧95% by weight. The stream Y thus removed can be recycled as such into reaction zone B to obtain reaction gas input mixture B. It will be appreciated that it is also possible, prior to the recycling of the stream Y removed as described into reaction zone B, to enrich the acetic acid content thereof by rectificative and/or crystallizative means (for example to acetic acid contents of ≧99% by weight), or to remove stream Y in the condensation column directly with such elevated purity by increasing the number of theoretical plates therein. Stream Z normally leaves the condensation column overhead.

Alternatively, it is also possible to proceed as recommended in documents DE-A 102009027401 and DE-A 10336386. After optionally preceding direct and/or indirect cooling, product mixture B in this procedure, in an absorption column advantageously equipped with separating internals, is conducted in countercurrent to an organic solvent having a higher boiling point than acrylic acid at standard pressure ($10^5$ Pa) (useful examples of these are the organic solvents specified in DE-A 102009027401 and in DE-A 10336386), and the acetic acid and acrylic acid present in product gas mixture B are absorbed into the organic solvent, while a stream Z leaves the absorption column at the top thereof. From the absorbate comprising acetic acid and acrylic acid, it is possible to remove streams X and Y with the desired degree of enrichment in each case by rectification (fractional distillation) in a rectification column in a manner known per se through appropriate selection of the number of theoretical plates. In general, this degree of enrichment of acrylic acid or acetic acid will be at least 90% by weight, preferably at least 95% by weight. A subsequent crystallizative further purification of the stream X removed (for example as disclosed in WO 01/77056) leads with a comparatively low level of complexity to acrylic acid purities of ≧99.9% by weight, which are suitable for production of water-absorbing resins by free-radical polymerization of monomer mixtures comprising acrylic acid and/or the sodium salt thereof. The stream Y removed by rectification as described can be recycled as such, or after optional crystallizative and/or rectificative further purification (for example to acetic acid contents of ≧99% by weight) into reaction zone B to obtain reaction gas input mixture B. By appropriately increasing the number of theoretical plates, it is also possible to remove stream Y from the absorbate by rectification directly with such a degree of enrichment.

Instead of using an organic absorbent, following the teaching of EP-A 551111 or EP-A 778255, it is also possible to absorb the acrylic acid and acetic acid present in product gas mixture B therefrom into an aqueous absorbent in an absorption column, while a stream Z leaves the absorption column at the top thereof. Subsequent rectificative separation of the aqueous absorbate, with optional inclusion of an azeotropic entraining agent, gives the desired streams X and Y.

The conversion of the acetic acid and acrylic acid present in reaction gas mixture B to the condensed phase to leave a gaseous stream Z can also be effected, for example, by one-stage condensation of those constituents present in reaction gas mixture B whose boiling points at standard pressure are not above that of acetic acid. Subsequently, the condensate comprising acrylic acid and acetic acid can be separated again, in the degree of enrichment desired in each case, into at least one stream Y and at least one stream X.

Appropriately in application terms, in the process according to the invention, at least 90 mol %, preferably at least 95 mol %, more preferably at least 98 mol % or at least 99 mol % of the acetic acid present in product gas mixture B is recycled into reaction zone B to obtain reaction gas input mixture B.

Instead of the process according to the invention being followed by a process in which acrylic acid present in stream X or a mixture of acrylic acid and one or more at least monoethylenically unsaturated monomers other than acrylic acid present in stream X are polymerized to polymers (for example by free-radical means; the polymerization may, for example, be a solution polymerization or an aqueous emulsion polymerization or a suspension polymerization), the process according to the invention may also be followed by a process in which acrylic acid present in stream X is esterified with at least one alcohol having, for example, 1 to 8 carbon atoms (for example an alcohol such as methanol, ethanol, n-butanol, tert-butanol and 2-ethyl-hexanol) to give the corresponding acrylic esters (acrylate). The process for acrylic ester preparation may then again be followed by a process in which the acrylic ester prepared or a mixture of the acrylic ester prepared and one or more at least monoethylenically unsaturated monomers other than the acrylic ester prepared are polymerized to polymers (for example by free-radical means; the polymerization may, for example, be a solution polymerization or an aqueous emulsion polymerization or a suspension polymerization).

For the sake of good order, it should also be emphasized that a deactivation of the different catalysts in the different reaction zones of the process according to the invention can be counteracted by correspondingly increasing the reaction temperature in the particular reaction zone (in order to keep the reactant conversion based on a single pass of the reaction gas mixture through the catalyst charge stable). It is also possible to regenerate the oxidic active materials of reaction zones A, B and C in a manner corresponding to that described for comparable oxidic catalysts in WO 2005/042459, by passing over an oxidizing oxygen-comprising gas at elevated temperature.

Reliable operation, especially in reaction zones A and C, can be ensured in the process according to the invention by an analogous application of the procedure described in WO 2004/007405.

The process according to the invention is notable firstly for its broad and wide-ranging raw material basis in terms of time. Secondly, it is a process which, in contrast to the prior art processes, enables a smooth transition from "fossil acrylic acid" to "renewable acrylic acid" while maintaining the procedure.

"Fossil acrylic acid" is understood to mean acrylic acid for which the ratio of the molar amount of $^{14}C$ atomic nuclei present in this acrylic acid to the molar amount of $^{12}C$ atomic nuclei present in the same acrylic acid, $n^{14}C:n^{12}C$, is vanishingly small.

"Renewable acrylic acid" is understood to mean acrylic acid for which the $n^{14}C:n^{12}C$ ratio corresponds to the ratio V* of $n^{14}C:n^{12}C$ present in the $CO_2$ in the earth's atmosphere, the $n^{14}C:n^{12}C$ ratio being determined by the procedure developed by Willard Frank Libby (http://de.wikipedia.orgn/wiki/Radikohlenstoffdatierung).

The terms "renewable carbon" and "fossil carbon" are used correspondingly in this document.

The process developed by Libby is based on the fact that, compared to the two carbon atom nuclei $^{12}C$ and $^{13}C$, the third naturally occurring carbon nucleus $^{14}C$ is unstable and is therefore also referred to as radiocarbon (half-life=approx. 5700 years).

In the upper layers of the earth's atmosphere, $^{14}C$ is constantly being newly formed by nuclei reaction. At the same time, $^{14}C$ decomposes with a half-life of 5700 years by β-decomposition. An equilibrium forms in the earth's atmosphere between constant new formation and constant degradation, and so the proportion of the $^{14}C$ nuclei in the carbon in the atmosphere on earth is constant over long periods; a stable ratio V* is present in the earth's atmosphere.

The radiocarbon produced in the atmosphere combines with atmospheric oxygen to give $CO_2$, which then gets into the biosphere as a result of photosynthesis. Since life forms (plants, animals, humans), in the course of their metabolism, constantly exchange carbon with the atmosphere surrounding them in this way, the same distribution ratio of the three carbon isotopes and hence the same $n^{14}C:n^{12}C$ ratio is established in living organisms as is present in the surrounding atmosphere.

When this exchange is stopped at the time of death of the life form, the ratio between $^{14}C$ and $^{12}C$ in the dead organism changes because the decomposing $^{14}C$ atomic nuclei are no longer replaced by new ones (the carbon present in the dead organism becomes fossil).

If the death of the organism (life form) was more than 50 000 years ago, the $^{14}C$ content thereof is below the detection limit. Present and future biological ("renewable") raw materials and chemicals produced therefrom have the particular current $^{14}C$ concentration in the $CO_2$ in the atmosphere on the earth (this $n^{14}C:n^{12}C$ ratio=V*). Fossil carbon sources such as coal, mineral oil or natural gas, however, have already lain "dead" in the earth for several million years, and they therefore, just like chemicals produced therefrom, no longer comprise any $^{14}C$.

When fossil ethanol (ethanol obtained from fossil raw materials) and renewable formaldehyde (formaldehyde obtained from renewable raw materials) are used in the process according to the invention, an acrylic acid is obtained whose $n^{14}C:n^{12}C$ ratio is only $(1/3) \times V^*$.

When, in the process according to the invention, in contrast, ethanol obtained from renewable raw materials and formaldehyde obtained from fossil raw materials are used, an acrylic acid is obtained whose $n^{14}C:n^{12}C$ ratio=$(2/3) \times V$.

When, in the process according to the invention, both fossil (renewable) ethanol and fossil (renewable) formaldehyde are used, an acrylic acid is obtained whose $n^{14}C:n^{12}C$ ratio=0 (=V*).

When the possibility of blending renewable and fossil starting materials (raw materials) is additionally considered in the process according to the invention, the manufacturer of acrylic acid, when employing the inventive procedure, is thus able, without altering the preparation process (i.e. with one and the same production plant), in accordance with customer requirements (for example the manufacturer of superabsorbents (=water-absorbing resins)), to adjust the "renewable level" of the acrylic acid to be supplied to this customer (the $n^{14}C:n^{12}C$ ratio desired by the customer for the acrylic acid to be supplied) as required.

By esterifying an acrylic acid for which V=V* with biomethanol or bioethanol, it is possible to obtain acrylic esters whose $n^{14}C$ to $n^{12}C$ ratio is likewise V*.

A further advantage of the inventive procedure is that neither the target product of reaction zone A nor the target product of reaction zone C require removal from product gas mixture A or C in order to be able to be employed for production of reaction gas input mixture B. This ensures both high economy and an efficient energy balance for the process according to the invention. Furthermore, in the case of condensation of acetic acid with formaldehyde, neither glyoxal nor propionic acid is formed as a by-product, as is necessarily the case for a heterogeneously catalyzed partial oxidation of propylene, propane, acrolein, propionaldehyde and/or glycerol to acrylic acid.

Furthermore, the process according to the invention ensures a high space-time yield coupled with simultaneously high target product selectivity based on the reactants converted.

Thus, the present application especially comprises the following embodiments of the invention:

1. A process for preparing acrylic acid from ethanol and formaldehyde, which comprises the following measures:

a stream of a reaction gas input mixture A comprising the ethanol and molecular oxygen reactants and at least one inert diluent gas other than steam is conducted through a first reaction zone A charged with at least one oxidation catalyst A and, in the course of passage through reaction zone A, ethanol present in the reaction gas input mixture A is oxidized under heterogeneous catalysis to acetic acid and steam so as to form a product gas mixture A comprising acetic acid, steam, molecular oxygen and at least one inert diluent gas other than steam, and a stream of product gas mixture A leaves reaction zone A, it optionally being possible to supply further molecular oxygen and/or further inert diluent gas to the reaction gas mixture A flowing through reaction zone A on its way through reaction zone A, a stream of a reaction gas input mixture B which comprises acetic acid, steam, molecular oxygen, at least one inert diluent gas other than steam and formaldehyde and in which the molar amount $n_{HAc}$ of acetic acid present is greater than the molar amount $n_{Fd}$ of formaldehyde present therein is obtained from the stream of product gas mixture A leaving reaction zone A and at least one further stream comprising at least one formaldehyde source, the stream of reaction gas input mixture B is passed through a second reaction zone B charged with at least one aldol condensation catalyst B and formaldehyde present in reaction gas input mixture B, as it flows through reaction zone B, is condensed with acetic acid present in reaction gas input mixture B under heterogeneous catalysis to give acrylic acid and $H_2O$, so as to form a product gas mixture B comprising acrylic acid, acetic acid, steam, molecular oxygen and at least one inert diluent gas other than steam, and a stream of product gas mixture B leaves reaction zone B, it optionally being possible to supply further molecular oxygen and/or further inert diluent gas to the reaction gas mixture B flowing through reaction zone B on its way through reaction zone B, the stream of product gas mixture B leaving reaction zone B is fed to a separation zone T and separated in separation zone T into at least three streams X, Y and Z, the acrylic acid flow present in stream X being greater than the acrylic acid flow present in streams Y and Z together, the acetic acid flow present in stream Y being greater than the acetic acid flow present in streams X and Z together, the flow of inert diluent gas other than steam present in stream Z being greater than the flow of inert diluent gas other than steam present in streams X and Y together, and stream Y is recycled into reaction zone B and used to obtain reaction gas input mixture B.

2. The process according to embodiment 1, wherein the at least one oxidation catalyst A has a catalytically active material which comprises at least one vanadium oxide.

3. The process according to embodiment 1 or 2, wherein the at least one oxidation catalyst A has a catalytically active material which comprises at least one vanadium oxide and additionally at least one oxide from the group of the oxides of titanium, of aluminum, of zirconium and of zinc.

4. The process according to embodiment 2 or 3, wherein the at least one vanadium oxide comprises the vanadium in the +5 oxidation state.

5. The process according to embodiment 3, wherein the at least one vanadium oxide comprises the vanadium in the +5 oxidation state and the at least one oxide from the group of the oxides of titanium, of zirconium and of tin comprises the element from the group of titanium, zirconium and tin in the +4 oxidation state.

6. The process according to any of embodiments 2 to 5, wherein the catalytically active material comprises $V_2O_5$ as at least one vanadium oxide.

7. The process according to embodiment 6, wherein the catalytically active material comprises 0.1 to 60% by weight of $V_2O_5$.

8. The process according to embodiment 6, wherein the catalytically active material comprises 1 to 50% by weight of $V_2O_5$.

9. The process according to embodiment 6, wherein the catalytically active material comprises 3 to 40% by weight of $V_2O_5$.

10. The process according to embodiment 6, wherein the catalytically active material comprises 5 to 30% by weight of $V_2O_5$.

11. The process according to any of embodiments 2 to 10, wherein the catalytically active material comprises $T_iO_2$.

12. The process according to any of embodiments 2 to 7, wherein the catalytically active material comprises 40 to 99.9% by weight of $T_iO_2$.

13. The process according to embodiment 8, wherein the catalytically active material comprises 50 to 99% by weight of $T_iO_2$.

14. The process according to embodiment 9, wherein the catalytically active material comprises 60 to 97% by weight of $T_iO_2$.

15. The process according to embodiment 10, wherein the catalytically active material comprises 70 to 95% by weight of $T_iO_2$.

16. The process according to any of embodiments 11 to 15, wherein the catalytically active material consists of $V_2O_5$ as at least one vanadium oxide and of $T_iO_2$.

17. The process according to any of embodiments 11 to 16, wherein at least a portion of the $T_iO_2$ is present in the anatase polymorph.

18. The process according to any of embodiments 11 to 16, wherein 50 to 100% by weight of the $T_iO_2$ is present in the anatase polymorph.

19. The process according to any of embodiments 2 to 18, wherein the at least one oxidation catalyst A is an unsupported catalyst.

20. The process according to embodiment 19, wherein the unsupported catalyst is a sphere, a ring or a solid cylinder.

21. The process according to embodiment 20, wherein the longest dimension of the unsupported catalyst is 1 to 10 mm.

22. The process according to any of embodiments 2 to 18, wherein the at least one oxidation catalyst A is an eggshell catalyst which has the catalytically active material as an eggshell on the surface of an inert shaped support body.

23. The process according to embodiment 22, wherein the shaped support body is a sphere or a ring.

24. The process according to embodiment 22 or 23, wherein the longest dimension of the shaped support body is 1 to 10 mm.

25. The process according to any of embodiments 22 to 24, wherein the inert shaped support body consists of steatite.

26. The process according to any of embodiments 22 to 25, wherein the thickness of the eggshell of catalytically active material is 10 to 2000 μm, or 10 to 500 μm, or 100 to 500 μm, or 200 to 300 μm.

27. The process according to embodiment 1, wherein the charge of the reaction zone A with at least one oxidation catalyst A comprises two sections 1 and 2 which are spatially successive in flow direction of reaction gas input mixture A in numerical sequence thereof and are charged with different oxidation catalysts A, said at least one oxidation catalyst A of section 1 having a catalytically active material 1 which comprises at least one vanadium oxide and at least one oxide from the group of the oxides of titanium, of aluminum, of zirconium and of tin, and said at least one oxidation catalyst A of section 2 having a catalytically active material 2 which is a multimetal oxide which, as well as V and Mo, additionally comprises at least one of the elements W, Mo, Ta, Cr and Ce, and at least one of the elements Cu, Ni, Co, Fe, Mn and Zn.

28. The process according to embodiment 27, wherein the catalytically active material 1 comprises or consists of 1 to 50% by weight of $V_2O_5$ as the at least one vanadium oxide and 50 to 99% by weight of $T_iO_2$ as the oxide of titanium (preferably in the anatase polymorph).

29. The process according to embodiment 27, wherein the catalytically active material 1 comprises or consists of 3 to 40% by weight of $V_2O_5$ as the at least one vanadium oxide and 60 to 97% by weight of $T_iO_2$ as the oxide of titanium (preferably in the anatase polymorph).
30. The process according to embodiment 27, wherein the catalytically active material 1 comprises or consists of 5 to 30% by weight of $V_2O_5$ as the at least one vanadium oxide and 70 to 95% by weight of $T_iO_2$ as the oxide of titanium (preferably in the anatase polymorph).
31. The process according to any of embodiments 27 to 30, wherein the at least one oxidation catalyst A of section 1 is an unsupported catalyst.
32. The process according to embodiment 31, wherein the geometry of the unsupported catalyst is selected from the group consisting of sphere, ring and solid cylinder, and has a longest dimension in the range from 1 to 10 mm.
33. The process according to any of embodiments 27 to 30, wherein the at least one oxidation catalyst A of section 1 is an eggshell catalyst which has the catalytically active material 1 applied as an eggshell to the surface of an inert shaped support body.
34. The process according to embodiment 33, wherein the shaped support body is a sphere or a ring.
35. The process according to embodiment 33 or 34, wherein the longest dimension of the shaped support body is 1 to 10 mm.
36. The process according to any of embodiments 33 to 35, wherein the inert support body consists of steatite.
37. The process according to any of embodiments 33 to 36, wherein the thickness of the eggshell of catalytically active material 1 is 10 to 2000 µm, or 10 to 500 µm, or 100 to 500 µm, or 200 to 300 µm.
38. The process according to any of embodiments 27 to 37, wherein the catalytically active material 1 does not comprise any Mo.
39. The process according to any of embodiments 27 to 38, wherein the catalytically active material 2 is at least one multimetal oxide of the general formula I

$$Mo_{12}V_aX^1_bX^2_cX^3_dX^4_eX^6_fX^6_gO_n \qquad (I)$$

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=1 to 6,
b=0.2 to 4,
c=0.5 to 1.8
d=0 to 40,
e=0 to 2,
f=0 to 4,
g=0 to 40, and
n=the stoichiometric coefficient of the element oxygen, which is determined by the stoichiometric coefficients of the non-oxygen elements and the charge numbers thereof in I.
40. The process according to any of embodiments 27 to 38, wherein the catalytically active material 2 is at least one multimetal oxide of the general formula I

$$Mo_{12}V_aX^1_bX^2_cX^3_dX^4_eX^5_fX^6_gO_n \qquad (I)$$

in which the variables are each defined as follows:
$X^1$=W, Nb and/or Cr,
$X^2$=Cu, Ni, Co, Fe, Mn and/or Fe,
$X^3$=Sb,
$X^4$=Na and/or K,
$X^5$=Ca, Sr and/or Ba,
$X^6$=Si, Al and/or Ti,
a=1.5 to 5,
b=0.5 to 2,
c=0.5 to 3,
d=0 to 2,
e=0 to 0.2
f=0 to 1
g=0 to 1, and
n=the stoichiometric coefficient of the element oxygen, which is determined by the stoichiometric coefficients of the non-oxygen elements and the charge numbers thereof in I.
41. The process according to any of embodiments 27 to 40, wherein the at least one oxidation catalyst A of section 2 is an eggshell catalyst which has the catalytically active material 2 applied as an eggshell to the surface of an inert shaped support body.
42. The process according to embodiment 41, wherein the shaped support body is a sphere or a ring.
43. The process according to embodiment 41 or 42, wherein the longest dimension of the shaped support body is 1 to 10 mm.
44. The process according to any of embodiments 41 to 43, wherein the inert shaped support body consists of steatite.
45. The process according to any of embodiments 41 to 44, wherein the thickness of the eggshell of catalytically active material 2 is 10 to 2000 µm, or 10 to 500 µm, or 100 to 500 µm, or 200 to 300 µm.
46. The process according to any of embodiments 1 to 45, wherein reaction zone A charged with at least one oxidation catalyst A has been charged with a fixed catalyst bed.
47. The process according to any of embodiments 1 to 46, wherein the reaction temperature in reaction zone A is in the range from 100 to 450° C.
48. The process according to any of embodiments 1 to 46, wherein the reaction temperature in reaction zone A is in the range from 100 to 350° C.
49. The process according to any of embodiments to 27 to 45, wherein the reaction temperature averaged arithmetically over the length of section 1, $T^1$ is 150 to 250° C., and the reaction temperature averaged arithmetically over the length of section 2, $T^2$ is 180 to 260° C.
50. The process according to embodiment 49, wherein $T^2$ is at least 5° C. greater than $T^2$.
51. The process according to embodiment 49, wherein $T^2$ is at least 10° C. greater than $T^1$.
52. The process according to embodiment 49, wherein $T^2$ is at least 20° C. greater than $T^1$.
53. The process according to any of embodiments 49 to 52, wherein $T^2$ is not more than 80° C. greater than $T^1$.
54. The process according to any of embodiments 27 to 46 and 49 to 53, wherein the ethanol present in reaction gas input mixture A is converted to an extent of at least 90 mol % in the course of passage through section 1.
55. The process according to any of embodiments 27 to 46 and 49 to 53, wherein the ethanol present in reaction gas input mixture A is converted to an extent of at least 95 mol % in the course of passage through section 1.
56. The process according to any of embodiments 27 to 46 and 49 to 55, wherein the ethanol present in reaction gas input mixture A is converted to an extent of at least 97 mol % in the course of passage through sections 1 and 2.
57. The process according to any of embodiments 27 to 46 and 49 to 56, wherein the ethanol present in reaction gas input mixture A is converted to an extent of at least 99 mol % in the course of passage through sections 1 and 2.

58. The process according to any of embodiments 1 to 57, wherein reaction gas input mixture A comprises 0.3 to 20% by volume of ethanol.
59. The process according to any of embodiments 1 to 57, wherein reaction gas input mixture A comprises 0.5 to 15% by volume of ethanol.
60. The process according to any of embodiments 1 to 57, wherein reaction gas input mixture A comprises 0.75 to 10% by volume or 1 to 5% by volume of ethanol.
61. The process according to any of embodiments 1 to 60, wherein reaction gas input mixture A comprises the molecular oxygen in a molar amount $n_O$ and the ethanol in a molar amount $n_{Et}$, and the $n_O$:$n_{Et}$ ratio is at least 1.3.
62. The process according to embodiment 61, wherein $n_O$:$n_{Et}$ is at least 1.5.
63. The process according to embodiment 61, wherein $n_O$:$n_{Et}$ is at least 1.75.
64. The process according to any of embodiments 61 to 63, wherein $n_O$:$n_{Et}$ is not more than 10.
65. The process according to any of embodiments 61 to 63, wherein $n_O$:$n_{Et}$ is not more than 5.
66. The process according to any of embodiments 1 to 65, wherein reaction gas input mixture A comprises 1 to 40% by volume of $H_2O$.
67. The process according to any of embodiments 1 to 65, wherein reaction gas input mixture A comprises 1 to 20% by volume of $H_2O$.
68. The process according to any of embodiments 1 to 65, wherein reaction gas input mixture A comprises 5 to 15% by volume of $H_2O$.
69. The process according to any of embodiments 1 to 65, wherein reaction gas input mixture A comprises 7.5 to 12.5% by volume of $H_2O$.
70. The process according to any of embodiments 1 to 69, wherein at least 80% by volume of the inert diluent gas other than steam present in reaction gas input mixture A is molecular nitrogen.
71. The process according to any of embodiments 1 to 69, wherein at least 90% by volume of the inert diluent gas other than steam present in reaction gas input mixture A is molecular nitrogen.
72. The process according to any of embodiments 1 to 69, wherein at least 95% by volume of the inert diluent gas other than steam present in reaction gas input mixture A is molecular nitrogen.
73. The process according to any of embodiments 1 to 72, wherein reaction gas input mixture A comprises, as at least one inert diluent gas other than steam, at least 10% by volume of molecular nitrogen.
74. The process according to any of embodiments 1 to 72, wherein reaction gas input mixture A comprises, as at least one inert diluent gas other than steam, at least 30% by volume of molecular nitrogen.
75. The process according to any of embodiments 1 to 72, wherein reaction gas input mixture A comprises, as at least one inert diluent gas other than steam, at least 40% by volume of molecular nitrogen.
76. The process according to any of embodiments 1 to 72, wherein reaction gas input mixture A comprises, as at least one inert diluent gas other than steam, not more than 90% by volume of molecular nitrogen.
77. The process according to any of embodiments 1 to 76, wherein the working pressure in reaction zone A is $1.2 \cdot 10^5$ Pa to $50 \cdot 10^5$ Pa.
78. The process according to any of embodiments 1 to 77, wherein the source used for ethanol present in reaction gas input mixture A is bioethanol.
79. The process according to embodiment 78, wherein reaction gas input mixture A, based on the weight of the ethanol present therein, has at least one 1 ppm by weight of a chemical compound comprising the element sulfur, calculated as the amount of sulfur present.
80. The process according to embodiment 78, wherein reaction gas input mixture A, based on the weight of the ethanol present therein, has 2 to 200 ppm by weight of a chemical compound comprising the element sulfur, calculated as the amount of sulfur present.
81. The process according to any of embodiments 1 to 78, wherein reaction gas input mixture A, based on the weight of the ethanol present, has 0 to <1 ppm by weight of a chemical compound comprising the element sulfur, calculated as the amount of sulfur present.
82. The process according to any of embodiments 78 to 81, wherein the source for the ethanol present in reaction gas input mixture A is an aqueous solution of bioethanol.
83. The process according to embodiment 82, wherein the source used for the ethanol present in reaction gas input mixture A is the filtrate of an aqueous slurry which comprises dissolved bioethanol and is obtained in bioethanol production.
84. The process according to any of embodiments 1 to 83, wherein the formaldehyde source used for the formaldehyde present in reaction gas input mixture B is at least one of the sources trioxane, paraformaldehyde, formalin, methylal, aqueous paraformaldehyde solution, aqueous formaldehyde solution, and the product gas mixture of a heterogeneously catalyzed partial gas phase oxidation of methanol to formaldehyde from which any unconverted methanol present therein has optionally been removed.
85. The process according to any of embodiments 1 to 84, wherein the reaction temperature in reaction zone B is 260 to 400° C.
86. The process according to any of embodiments 1 to 84, wherein the reaction temperature in reaction zone B is 280 to 380° C.
87. The process according to any of embodiments 1 to 84, wherein the reaction temperature in reaction zone B is 300 to 370° C.
88. The process according to any of embodiments 1 to 87, wherein the working pressure in reaction zone B is $1.2 \cdot 10^5$ Pa to $50 \cdot 10^5$ Pa.
89. The process according to any of embodiments 1 to 88, wherein the formaldehyde content in reaction gas input mixture B is 0.5 to 10% by volume.
90. The process according to any of embodiments 1 to 88, wherein the formaldehyde content in reaction gas input mixture B is 0.5 to 7% by volume.
91. The process according to any of embodiments 1 to 88, wherein the formaldehyde content in reaction gas input mixture B is 1 to 5% by volume.
92. The process according to any of embodiments 1 to 91, wherein reaction gas input mixture B comprises acetic acid in a molar amount $n_{HAc}$ and formaldehyde in a molar amount $n_{Fd}$, and the $n_{HAc}$:$n_{Fd}$ ratio is greater than 1 and 10.
93. The process according to embodiment 92, wherein the $n_{HAc}$:$n_{Fd}$ ratio is 1.1 to 5.
94. The process according to embodiment 92, wherein the $n_{HAc}$:$n_{Fd}$ ratio is 1.5 to 3.5.
95. The process according to any of embodiments 1 to 94, wherein the acetic acid content of reaction gas input mixture B is 1.5 to 20% by volume.
96. The process according to any of embodiments 1 to 94, wherein the acetic acid content of reaction gas input mixture B is 2 to 15% by volume.

97. The process according to any of embodiments 1 to 94, wherein the acetic acid content of reaction gas input mixture B is 3 to 10% by volume.
98. The process according to any of embodiments 1 to 97, wherein the molecular oxygen content of reaction gas input mixture B is 0.5 to 5% by volume.
99. The process according to any of embodiments 1 to 97, wherein the molecular oxygen content of reaction gas input mixture B is 2 to 5% by volume.
100. The process according to any of embodiments 1 to 99, wherein the steam content of reaction gas input mixture B does not exceed 30% by volume and is not less than 1.5% by volume.
101. The process according to any of embodiments 1 to 99, wherein the steam content of reaction gas input mixture B does not exceed 20% by volume and is not less than 2% by volume.
102. The process according to any of embodiments 1 to 99, wherein the steam content of reaction gas input mixture B is 5 to 15% by volume or 10 to 15% by volume.
103. The process according to any of embodiments 1 to 102, wherein the content of inert diluent gas other than steam in reaction gas input mixture B is at least 30% by volume or at least 40% by volume.
104. The process according to any of embodiments 1 to 102, wherein the content of inert diluent gas other than steam in reaction gas input mixture B is at least 50% by volume.
105. The process according to any of embodiments 1 to 104, wherein reaction gas input mixture B comprises, as at least one inert diluent gas other than steam, at least 30% by volume or at least 40% by volume of $N_2$.
106. The process according to any of embodiments 1 to 104, wherein reaction gas input mixture B comprises, as at least one inert diluent gas other than steam, at least 50% by volume of $N_2$.
107. The process according to any of embodiments 1 to 106, wherein the at least one aldol condensation catalyst B is a zeolite with anionic structural charge, on whose inner and outer surfaces at least one cation type from the group of the alkali metal ions and alkaline earth metal ions is present, in order to neutralize the negative structural charge.
108. The process according to any of embodiments 1 to 106, wherein the at least one aldol condensation catalyst B is hydroxide from the group consisting of alkali metal hydroxides, alkaline earth metal hydroxides and aluminum hydroxide applied to amorphous silicon dioxide.
109. The process according to embodiment 108, wherein the hydroxide applied to the amorphous silicon dioxide is KOH, NaOH, $Ca(OH)_2$ or $Mg(OH)_2$.
110. The process according to any of embodiments 1 to 106, wherein the at least one aldol condensation catalyst B is a catalyst which comprises
as constituent a), at least one oxide of at least one of the elements Si, Al, Ti, Zr, Cd, Sn, Ga, Y and La and/or zeolite, and
as constituent b), at least one oxide selected from boron oxide and phosphorus oxide, and optionally
as constituent c) one or more than one oxide of at least one of the elements V, Cr, Co, Ni, Mo and Pb and/or more than one heteropolyacid with at least one poly atom selected from V, Mo and W.
111. The process according to embodiment 110, wherein the at least one aldol condensation catalyst B comprises 1 to 50% by weight of boron oxide, or 1 to 50% by weight of phosphorus oxide, or 1 to 50% by weight of boron oxide and phosphorus oxide, where the boron oxide, based on the amount of B present, is always calculated as $B_2O_3$ and the phosphorus oxide, based on the amount of P present, is always calculated as $P_2O_5$.
112. The process according to any of claims 1 to 106, wherein the at least one aldol condensation catalyst B has a catalytically active material which is a vanadium-phosphorus oxide or a vanadium-phosphorus oxide doped with elements other than vanadium and phosphorus.
113. The process according to embodiment 112, wherein the catalytically active material is a multielement oxide active material of the general formula II $$V_1P_bFe_cX^1_dX^2_eO_n \qquad (II)$$

in which the variables are each defined as follows:
$X^1$=Mo, Bi, Co, Ni, Si, Zn, Hf, Zr, Ti, Cr, Mn, Cu, B, Sn and/or Nb,
$X^2$=Li, K, Na, Rb, Cs and/or Tl,
b=0.9 to 2.0
c=$\geq$0 to 0.1,
d=$\geq$0 to 0.1,
e=0 to 0.1, and
n=the stoichiometric coefficient of the element oxygen, which is determined by the stoichiometric coefficients of the non-oxygen elements and the charge numbers thereof in II.
114. The process according to embodiment 113, wherein $X^1$=Nb, Mo, Zn and/or Hf.
115. The process according to embodiment 113 or 114, wherein
b is 0.9 to 1.5.
116. The process according to embodiment 113 or 114, wherein b is 0.9 to 1.2.
117. The process according to any of embodiments 113 to 116, wherein $X^1$=Mo.
118. The process according to any of embodiments 113 to 117, wherein c is 0.005 to 0.1.
119. The process according to any of embodiments 113 to 117, wherein c is 0.005 to 0.05 or 0.005 to 0.02.
120. The process according to embodiment 112, wherein the ratio $n_p$:$n_v$ of the molar amount $n_p$ of phosphorus present in the catalytically active material to the molar amount $n_v$ of V present in the catalytically active material is 0.09 to 2.0, preferably 0.9 to 1.5 and more preferably 0.9 to 1.2.
121. The process according to either of embodiments 112 or 120, wherein the elements other than vanadium or phosphorus present in the catalytically active material are one or more than one element from the group consisting of lithium, potassium, sodium, rubidium, cesium, thallium, molybdenum, zinc, hafnium, zirconium, titanium, chromium, manganese, nickel, copper, iron, boron, silicon, tin, niobium, cobalt and bismuth.
122. The process according to embodiment 121, wherein the total content of elements other than vanadium and phosphorus in the catalytically active material, based on the weight thereof, is not more than 5% by weight, calculating the particular element other than vanadium and phosphorus as the electrically neutral oxide in which the element has the same charge number as in the active material.
123. The process according to any of embodiments 112 to 122, wherein the arithmetic mean oxidation state of vanadium in the catalytically active material is +3.9 to +4.4 or +4.0 to +4.3.
124. The process according to any of embodiments 112 to 123, wherein the specific BET surface area of the catalytically active material is $\geq$15 to 50 m$^2$/g.

125. The process according to any of embodiments 112 to 124, wherein the total pore volume of the catalytically active material is 0.1 to 0.5 ml/g.
126. The process according to any of embodiments 112 to 125, wherein the total pore volume of the catalytically active material is 0.15 to 0.4 ml/g.
127. The process according to any of embodiments 112 to 126, wherein the at least one oxidation catalyst B is an unsupported catalyst or a supported catalyst.
128. The process according to embodiment 127, wherein the geometry of the unsupported catalyst is selected from the group consisting of sphere, ring and solid cylinder, and has a longest dimension in the range from 1 to 10 mm.
129. The process according to embodiment 127, wherein the geometry of the unsupported catalyst is a ring (a hollow cylinder) with an external diameter in the range from 3 to 10 mm, a height of 1 to 10 mm, an internal diameter of 1 to 8 mm and a wall thickness of 1 to 3 mm.
130. The process according to any of embodiments 112 to 126, wherein the at least one aldol condensation catalyst B is an eggshell catalyst which has the catalytically active material as an eggshell applied to the surface of an inert shaped support body.
131. The process according to embodiment 130, wherein the shaped support body is a sphere or a ring.
132. The process according to embodiment 130 or 131, wherein the longest dimension of the shaped support body is 1 to 10 mm.
133. The process according to any of embodiments 130 to 132, wherein the inert shaped support body is composed of steatite.
134. The process according to any of embodiments 130 to 133, wherein the thickness of the eggshell of active material is 10 to 2000 µm, or 10 to 500 µm, or 100 to 500 µm, or 200 to 300 µm.
135. The process according to any of embodiments 1 to 134, which comprises a further, third reaction zone C which has been charged with at least one oxidation catalyst C and comprises the following additional measures:
   a stream of a reaction gas input mixture C comprising the methanol and molecular oxygen reactants and at least one inert diluent gas other than steam is passed through a third reaction zone C charged with at least one oxidation catalyst C and methanol present in reaction gas input mixture C, as it passes through reaction zone C, is oxidized under heterogeneous catalysis to formaldehyde and steam, so as to form a product gas mixture C comprising formaldehyde, steam and at least one inert diluent gas other than steam, and a stream of product gas mixture C leaves reaction zone C, it optionally being possible to add further molecular oxygen and/or further inert diluent gas to reaction gas mixture C flowing through reaction zone C on its way through reaction zone C,
   optionally, from product gas mixture C, any unconverted methanol still present in product gas mixture C is removed from product gas mixture C in a separation zone T* to leave a formaldehyde-comprising product gas mixture C*, and
   product gas mixture C or product gas mixture C* is conducted into reaction zone B to obtain reaction gas input mixture B.
136. The process according to embodiment 135, wherein methanol removed in separation zone T* is recycled into reaction zone C to obtain reaction gas input mixture C.
137. The process according to embodiment 135 or 136, wherein the methanol is removed by rectification in the separation zone T*.
138. The process according to any of embodiments 135 to 137, wherein the at least one oxidation catalyst C has a catalytically active material which comprises at least elemental silver.
139. The process according to embodiment 138, wherein the purity of the elemental silver is $\geq 99.7\%$ by weight.
140. The process according to embodiment 138, wherein the purity of the elemental silver is $\geq 99.9$ or $\geq 99.99\%$ by weight.
141. The process according to any of embodiments 138 to 140, wherein the at least one oxidation catalyst C comprises silver crystals whose longest dimension is in the range from 0.1 to 5 mm.
142. The process according to embodiment 141, wherein the silver crystals have been coated with a porous layer of oxidic material of at least one of the elements Al, Si, Zr and Ti, the thickness of which is in the range of 0.3 to 10 µm.
143. The process according to any of embodiments 138 to 142, wherein the methanol content of reaction gas input mixture C is at least 5% by volume.
144. The process according to embodiment 143, wherein the methanol content of reaction gas input mixture C is not more than 60% by volume.
145. The process according to any of embodiments 138 to 142, wherein the methanol content of reaction gas input mixture C is 15 to 50% by volume.
146. The process according to any of embodiments 138 to 142, wherein the methanol content of reaction gas input mixture C is 20 to 40% by volume or 20 to 30% by volume.
147. The process according to any of embodiments 138 to 146, wherein the reaction gas input mixture C comprises the molecular oxygen in a molar amount $n_O$ and the methanol in a molar amount $n_{Me}$, and the $n_O:n_{Me}$ ratio is less than 1.
148. The process according to embodiment 147, wherein $n_O:n_{Me}$ is 0.1 to 0.8 or 0.2 to 0.6.
149. The process according to any of embodiments 138 to 148, wherein $n_O:n_{Me}$ is 0.3 to 0.5.
150. The process according to any of embodiments 138 to 149, wherein reaction gas input mixture C comprises 0 to 50% by volume of $H_2O$.
151. The process according to embodiment 150, wherein reaction gas input mixture C comprises 15 to 35% by volume or 20 to 30% by volume of $H_2O$.
152. The process according to any of embodiments 138 to 151, wherein reaction gas input mixture C comprises, as at least one inert diluent gas other than steam, $N_2$.
153. The process according to embodiment 152, wherein reaction gas input mixture C comprises 20 to 80% by volume of $N_2$.
154. The process according to embodiment 152 or 153, wherein reaction gas input mixture C comprises 30 to 70% by volume of $N_2$.
155. The process according to any of embodiments 152 to 154, wherein reaction gas input mixture C comprises 40 to 60% by volume of $N_2$.
156. The process according to any of embodiments 138 to 155, wherein the methanol is oxidized in the reaction zone C at a reaction temperature in the range from 400 to 800° C. to formaldehyde and water.
157. The process according to any of embodiments 138 to 156, wherein the methanol is oxidized in the reaction zone C at a reaction temperature in the range from 500 to 800° C. to formaldehyde and water.

158. The process according to any of embodiments 138 to 156, wherein the methanol is oxidized in the reaction zone C at a reaction temperature in the range from 450 to 650° C., or from 500 bis 600° C. to formaldehyde and water.
159. The process according to any of embodiments 138 to 156, wherein the methanol is oxidized in the reaction zone C at a reaction temperature in the range from 600 to 750° C. to formaldehyde and water.
160. The process according to any of embodiments 138 to 159, wherein the methanol is oxidized in reaction zone C at a working pressure in the range from $10^3$ to $10^6$ Pa or from $10^4$ to $2 \cdot 10^5$ Pa to formaldehyde and water.
161. The process according to any embodiments 135 to 137, wherein the at least one oxidation catalyst C has a catalytically active material which is a mixed oxide which has at least one transition metal in the oxidized state.
162. The process according to embodiment 161, wherein the at least one transition metal comprises Mo and/or V.
163. The process according to embodiment 161, wherein the at least one transition metal comprises Mo and Fe.
164. The process according to embodiment 161, wherein the catalytically active material is a mixed oxide of the general formula III

   (III)

in which the variables are each defined as follows:
$M^1$=Mo and/or Fe, or
  Mo and/or Fe and, based on the total molar amount of Mo and Fe, a total molar amount of up to 10 mol % (eg. 0.01 to 10 mol % or 0.1 to 10 mol %), preferably not more than 5 mol %, of one or more elements from the group consisting of Ti, Sb, Sn, Ni, Cr, Ce, Al, Ca, Mg, V, Nb, Ag, Mn, Cu, Co, Si, Na, K, Tl, Zr, W, Ir, Ta, As, P and B,
q=0 to 5,
m=1 to 3,
n=1 to 6.
165. The process according to embodiment 164, wherein q=0.5 to 3.
166. The process according to embodiment 164 or 165, wherein q=1 to 2.
167. The process according to any of embodiments 164 to 166, wherein $M^1$=Mo, m=1 and n=3.
168. The process according to any of embodiments 164 to 166, wherein $M^1$=Fe, m=2 and n=3.
169. The process according to any of embodiments 164 to 168, wherein less than 50 mol % of the Fe present in the mixed oxide III is present in the +2 oxidation state.
170. The process according to any of embodiments 164 to 168, wherein less than 20 mol % of the Fe present in the mixed oxide III is present in the +2 oxidation state.
171. The process according to any of embodiments 164 to 168, wherein less than 10 mol % of the Fe present in the mixed oxide III is present in the +2 oxidation state.
172. The process according to any of embodiments 164 to 168, wherein the entirety of the Fe present in the mixed oxide III is present in the +3 oxidation state.
173. The process according to any of embodiments 164 to 172, wherein the $n_{Mo}:n_{Fe}$ ratio, formed from the molar amount of Mo present in the mixed oxide III and the molar amount of Fe present in the same mixed oxide III, is 1:1 to 5:1.
174. The process according to any of embodiments 164 to 172, wherein the catalytically active material can be represented in a formal sense as a mixture of $MoO_3$ and $Fe_2O_3$, the content in the mixture of $MoO_3$ being 65 to 95% by weight and the content in the mixture of $Fe_2O_3$ being 5 to 35% by weight.
175. The process according to any of embodiments 161 to 174, wherein the at least one oxidation catalyst C is an unsupported catalyst.
176. The process according to embodiment 175, wherein the geometry of the unsupported catalyst is selected from the group consisting of sphere, ring and solid cylinder.
177. The process according to embodiment 176, wherein the longest dimension of the unsupported catalyst is 1 to 10 mm.
178. The process according to embodiment 175, wherein the unsupported catalyst has the geometry of a ring with an external diameter of 3 to 10 mm, a height of 1 to 10 mm and an internal diameter of 1 to 8 mm.
179. The process according to embodiment 178, wherein the ring has a wall thickness of 1 to 3 mm.
180. The process according to any of embodiments 161 to 174, wherein the at least one oxidation catalyst C is an eggshell catalyst which has the catalytically active mixed oxide as an eggshell applied to the surface of an inert shaped support body.
181. The process according to embodiment 180, wherein the shaped support body is a sphere or a ring.
182. The process according to embodiment 181, wherein the longest dimension of the shaped support body is 1 to 10 mm.
183. The process according to embodiment 180, wherein the inert shaped support body is a ring with a length of 2 to 10 mm, an external diameter of 4 to 10 mm and a wall thickness of 1 to 4 mm.
184. The process according to any of embodiments 180 to 183, wherein the inert shaped support body is composed of steatite.
185. The process according to any of embodiments 180 to 184, wherein the eggshell of catalytically active mixed oxide has a thickness of 10 to 2000 μm or 10 to 500 μm, or 100 to 500 μm, or 200 to 300 μm.
186. The process according to any of embodiments 161 to 185, wherein reaction gas input mixture C comprises not more than 15% by volume of methanol.
187. The process according to any of embodiments 161 to 185, wherein reaction gas input mixture C comprises not more than 11% by volume of methanol.
188. The process according to any of embodiments 161 to 187, wherein reaction gas input mixture C comprises 2 to 10% by volume of methanol.
189. The process according to any of embodiments 161 to 188, wherein reaction gas input mixture C comprises 6 to 9% by volume of methanol.
190. The process according to any of embodiments 161 to 189, wherein reaction gas input mixture C comprises the molecular oxygen in a molar amount no and the methanol in a molar amount $n_{Me}$, and the $n_O:n_{Me}$ ratio is at least 1 or greater than 1.
191. The process according to embodiment 190, wherein the $n_O:n_{Me}$ ratio is 1.1 to 5.
192. The process according to embodiment 190 or 191, wherein the $n_O:n_{Me}$ ratio is 1.5 to 3.5.
193. The process according to any of embodiments 161 to 192, wherein reaction gas input mixture C comprises, as at least one inert diluent gas other than steam, $N_2$.
194. The process according to embodiment 193, wherein reaction gas input mixture C comprises 70 to 95% by volume of $N_2$.

195. The process according to any of embodiments 161 to 194, wherein reaction gas input mixture C comprises 0 to 20% by volume of $H_2O$.
196. The process according to embodiment 195, wherein reaction gas input mixture C comprises 0.1 to 10% by volume of $H_2O$.
197. The process according to embodiment 195 or 196, wherein reaction gas input mixture C comprises 0.2 to 7% by volume of $H_2O$.
198. The process according to any of embodiments 194 to 196, wherein reaction gas input mixture C comprises 0.5 to 5% by volume of $H_2O$.
199. The process according to any of embodiments 161 to 198, wherein the methanol is oxidized in reaction zone C at a reaction temperature in the range from 250 to 500° C. to formaldehyde and water.
200. The process according to embodiment 199, wherein the methanol is oxidized in reaction zone C at a reaction temperature in the range from 250 to 400° C. to formaldehyde and water.
201. The process according to any of embodiments 161 to 200, wherein the methanol is oxidized in reaction zone C at a working pressure in the range from $10^3$ to $10^6$ Pa or from $10^4$ to $2 \cdot 10^5$ Pa to formaldehyde and water.
202. The process according to any of embodiments 1 to 201, wherein a portion of stream Y is recycled into reaction zone A to obtain reaction gas input mixture A.
203. The process according to any of embodiments 135 to 202, wherein a portion of stream Y is recycled into reaction zone C to obtain reaction gas input mixture C.
204. The process according to any of embodiments 1 to 203, wherein product gas mixture B is separated in separation zone T by passing product gas mixture B, optionally after direct and/or indirect cooling thereof, into a condensation column equipped with separating internals and fractionally condensing it within the condensation column and conducting streams X, Y and Z out of the condensation column as separate fractions.
205. The process according to any of embodiments 1 to 203, wherein product gas mixture B is separated in separating zone T by passing product gas mixture B, optionally after direct and/or indirect cooling thereof, into an absorption column equipped with separating internals in countercurrent to an organic solvent with a higher boiling point than acrylic acid at standard pressure, and absorbing the acetic acid and acrylic acid present in product gas mixture B into the solvent to obtain an absorbate, while a stream Z leaves the absorption column at the top thereof, and then removing streams X and Y from the absorbate as separate fractions by fractional distillation thereof in a rectification column.
206. The process according to any of embodiments 1 to 203, wherein product gas mixture B is separated in separating zone T by passing product gas mixture B, optionally after direct and/or indirect cooling thereof, into an absorption column equipped with separating internals in countercurrent to an aqueous solution as an absorbent, and absorbing the acetic acid and acrylic acid present in product gas mixture B into the solvent to obtain an absorbate, while a stream Z leaves the absorption column at the top thereof, and then removing streams X and Y as separate fractions from the absorbate by fractional distillation thereof in a rectification column.
207. Acrylic acid for which the ratio V of the molar amount $n^{14}C$ of $^{14}C$ atomic nuclei present in this acrylic acid to the molar amount $n^{12}C$ of $^{12}C$ atomic nuclei present in the same acrylic acid, $V = n^{14}C : n^{12}C$, is greater than 0 and less than the corresponding molar ratio $V^*$ of $^{14}C$ atomic nuclei to $^{12}C$ atomic nuclei present in the carbon dioxide in the earth's atmosphere.
208. Acrylic acid according to embodiment 207, wherein $V = (\frac{1}{3}) \cdot V^*$.
209. Acrylic acid according to embodiment 207, wherein $V = (\frac{2}{3}) \cdot V^*$.
210. A liquid phase P comprising at least 1 kg of acrylic acid, wherein the acrylic acid present is an acrylic acid according to any of embodiments 207 to 209.

EXAMPLES

I) Preparation of Different Catalysts

A) Preparation of a mixed oxide catalyst for the heterogeneously catalyzed partial gas phase oxidation of methanol to formaldehyde by the FORMOX process.

530 g of ammonium heptamolybdate tetrahydrate ($(NH_4)_6Mo_7O_{24} \cdot 4H_2O$) were dissolved in a mixture, at a temperature of 60° C., of 800 ml of water and 250 g of a 25% by weight aqueous ammonia solution while maintaining the 60° C. This gave a solution 1 at 60° C.

808 g of iron(III) nitrate nonahydrate ($Fe(NO_3)_3 \cdot 9H_2O$) were dissolved in 1000 ml of water at 60° C. while maintaining the 60° C. This gave a solution 2 at 60° C.

Within 20 min, solution 2 was stirred continuously into solution 1 while maintaining the 60° C. Subsequently, the mixture was stirred at 60° C. for another 5 min. The aqueous suspension obtained was subsequently spray-dried at an inlet temperature of 340° C. and an outlet temperature of 120° C. in an air stream within 1.5 h (spray tower of the Mobile Minor 2000 (MM-I) type from Niro NS, Gladsaxevej 305, 2860 Soborg, Denmark, with a centrifugal atomizer of the FO1A type and an atomizer wheel of the SL24-50 type). During the spray drying, stirring of the proportion of the suspension which was yet to be sprayed in each case was continued while maintaining the 60° C.

The spray powder thus obtained was, based on its weight, mixed homogeneously with 1% by weight of TIM-REX® T44 graphite from Timcal AG (cf. WO 2008/087116) (in a drum hoop mixer; wheel diameter: 650 mm, drum volume: 5 l, speed: approx. 30 rpm, mixing time: 30 min). The resulting mixture was then compacted in a roll compactor of the RCC 100×20 type from Powtec with 2 contrarotary steel rolls with a pressure of 12 bar, and then forced through a screen with square meshes of mesh size 0.8 mm. The resulting compactate (which had a bulk density of 1050 g/l and an essentially homogeneous particle size of $\geq 0.4$ mm and $\leq 0.8$ mm) was subsequently mixed in the aforementioned drum hoop mixer at a speed of approx. 30 rpm within 30 min with, based on its weight, 3% by weight of the same graphite, and then compacted as described in DE-A 10 2008040093 to annular shaped unsupported catalyst precursor bodies of geometry 5 mm×3 mm×3 mm (external diameter×height×internal diameter) with a side crushing strength of 22±5 N and a mass of 130 mg (fill height: 7.5-9 mm; pressing force: 3.0-3.5 kN; Kilian rotary tableting press (9-die tableting machine) of the S100 type (from Kilian, D-50735 Cologne). The tableting was effected under a nitrogen atmosphere.

For the final thermal treatment, the shaped catalyst precursor bodies were divided homogeneously between 4 grids arranged alongside one another with a square base area of in each case 150 mm×150 mm (bed height: approx. 40 mm) and treated in a forced-air oven with air flow (from Heraeus Instruments GmbH, D-63450 Hanau, model: K 750/2) as follows: the air flow was 100 l (STP)/h and initially had a temperature of 120° C. The 120° C. was first maintained for 10 h. Then the temperature was increased to 460° C. in an essentially linear manner within 10 h, and the 460° C. was then maintained for a further 4 h. This was followed by cooling to 25° C. within 5 h.

An annular unsupported oxidation catalyst C was thus obtained, the mixed oxide active material of which had the stoichiometry $Fe_2(MoO_4)_3$. Subsequently, the unsupported catalyst rings were forced through a screen with square meshes of mesh size 0.8 mm. The material passing through the screen (spall of oxidation catalyst C) had an essentially homogeneous particle size (longest dimension) of $\geq 0.4$ mm and $\leq 0.8$ mm.

B) Production of a mixed oxide catalyst for charging of section 1 of a reaction zone A for the heterogeneously catalyzed partial gas phase oxidation of ethanol to acetic acid.

380 g of water were initially charged in a 2 l beaker and heated to 55° C. Then 220 g of oxalic acid dihydrate were added and dissolved while stirring and maintaining the 55° C. After complete dissolution of the oxalic acid dihydrate, 116 g of finely divided $V_2O_5$ were added, which formed a deep blue vanadium complex. After the addition of the $V_2O_5$ had ended, the mixture was heated while stirring to 80° C. in an essentially linear manner within 20 min. This temperature was maintained while stirring for a further 10 min. Thereafter, the aqueous solution formed was cooled in an essentially linear manner to 25° C. within 60 min.

To 135 ml of the aqueous solution prepared as described were added 97.5 g of finely divided titanium dioxide (manufacturer: Fuji; type: TA 100C; anatase polymorph; specific surface area (BET); 20 m²/g; 2200 ppm of sulfur; 1600 ppm of niobium; particle size distribution (stir 1 g of $TiO_2$ in 100 ml of water with a magnetic stirrer for 10 min, then determine the particle diameter distribution by means of dynamic light scattering in a mastersizer S from Malvern Instruments with an MS1 small volume wet dispersing unit): $d_{10}=0.6$ µm, $d_{50}=1.1$ µm, $d_{90}=2.1$ µm; $d_x$ means that X % of the total particle volume consists of particles with this or a smaller diameter). Subsequently, the mixture was homogenized at 8000 rpm for 3 minutes with an Ultra Turax stirrer from Janke & Kunkel GmbH and Co. KG-IKA Labortechnik (shaft type: S 50KR-G45 F, shaft tube diameter: 25 mm, stator diameter: 45 mm, rotor diameter: 40 mm). The resulting aqueous dispersion was used to coat 150 g of spall of C220 steatite from CeramTec with a longest dimension in the range from 1 mm to 1.5 mm.

For this purpose, the 150 g of steatite spall were introduced into a rotating coating drum (with an internal radius of 15 cm and an internal volume of 1800 cm³) as a coating system. The speed of the coating drum was 200 rpm. The aqueous dispersion was applied to the surface of the steatite spall by spraying the aqueous dispersion with the aid of a two-substance atomization nozzle.

The atomization medium used was 250 l (STP)/h of compressed air (10 bar gauge) at a temperature of 25° C. The dispersion flow rate was 100 ml/h at a temperature of the aqueous dispersion of 25° C. The atomization was in the form of a circular solid cone (10°-40°. The atomization type was mist, with a droplet size of <50 to 150 µm. The diameter of the flow cross section for the dispersion was 1 mm. The internal temperature of the coating drum was kept at 120° C. in the course of the coating operation.

After the spraying operation had ended, drying was effected for another 30 min in the coating drum under otherwise unchanged conditions. Subsequently, the coated support particles were introduced into a porcelain dish and calcined therein in a muffle furnace (capacity 1.5 l) under air (stationary). To this end, the temperature in the calcination material was increased with a heating rate of 3° C./min from 100° C. to 500° C., and then kept at this temperature for 3 h. Finally, the calcination material was cooled within the muffle furnace essentially in a linear manner to 25° C. within 12 h.

The oxidation catalyst A(1) thus obtained was an eggshell catalyst whose catalytically active mixed oxide eggshell had an average stoichiometry of $(V_2O_5)_x (TiO_2)_y$ where x=18.3% by weight and y=81.7% by weight.

C) Production of a mixed oxide catalyst for charging of section 2 of a reaction zone A for the heterogeneously catalyzed partial gas phase oxidation of ethanol to acetic acid 127 g of copper(II) acetate monohydrate were dissolved in 2700 g of water at a temperature of 25° C., while maintaining this temperature, to give a solution 1.

860 g of ammonium heptamolybdate tetrahydrate were dissolved in 5500 g of water at a temperature of 95° C., while maintaining this temperature, within 5 min. Subsequently, while maintaining 95° C., 143 g of ammonium metavanadate were added and the resulting solution was stirred at 95° C. for a further 30 min. Thereafter, 126 g of ammonium paratungstate heptahydrate were added and the resulting solution was stirred at 95° C. for a further 40 min. Subsequently, the solution 2 thus obtained was cooled to 80° C. within 10 min.

Solution 1 at 25° C. was then stirred into solution 2 at 80° C., while maintaining the 80° C., within 5 min. The resulting solution was subsequently spray-dried in an air stream at an inlet temperature of 350° C. and an outlet temperature of 110° C. within 3 h (spray tower of the Mobile Minor 200 (MM-I) type from Niro NS, Gladsaxevej 305, 2860 Soborg, Denmark, with a centrifugal atomizer of the FO Al type and an atomizer wheel of the SL24-50 type). During the spray drying, the stirring of the proportion of the suspension which was yet to be sprayed in each case was continued while maintaining the 80° C. In each case 1 kg of the resulting spray powder was kneaded with 0.15 kg of water at a temperature of 25° C. (kneader from Werner & Pfleiderer of the ZS1-80 type; kneading time: approx. 2 hours; kneading temperature: 30 to 35° C.). Subsequently, the kneading material was calcined with a layer thickness of approx. 2 cm in a forced-air oven charged with an oxygen/nitrogen mixture. The molecular oxygen content of the oxygen/nitrogen mixture was adjusted such that the $O_2$ content at the outlet of the forced-air oven was 1.5% by volume. In the course of the calcination, the kneading material was first heated at a heating rate of 10° C./min from 30° C. to 300° C. (in each case, temperature of the calcination material) and then kept at this temperature for 6 h. Then the calcination material was heated with a heating rate of 10° C./min to 400° C. and this temperature was subsequently maintained for 1 h. Subsequently, the temperature of the calcination material was cooled in an essentially linear manner to 25° C. within 12 h. The oven loading for the calcination was 250 g/l (g of kneading material per l of capacity of the forced-air oven). The input volume flow of the oxygen/nitrogen mixture was 80 l (STP)/h and the residence time of the oxygen/nitrogen charge (calculated as the ratio of the capacity of the forced-air oven and the volume flow of the nitrogen/oxygen mixture supplied at a temperature of 25° C.) was 135 sec. The internal volume of the forced-air oven was 3 l.

The resulting catalytically active mixed oxide had the stoichiometry $Mo_{12}V_3W_{1.2}Cu_{1.6}O_n$.

The catalytically active oxide material was subsequently ground in a ZM 200 mill from Retsch to a fine powder whose particle diameter (longest dimension) was essentially in the range from 0.1 to 50 μm (a diameter distribution favorable in accordance with the invention for the fine powder is shown by FIG. 2 of DE-A 102010023312). This active material powder was used, in a rotary drum, in analogy to the coating process described in EP-A 714 700, to coat rough-surface spheres of C220 steatite from CeramTec with a sphere diameter of 2 to 3 mm with addition of water as a binder. Finally, the coated spheres were dried with air at 110° C. The active material content of the spherical eggshell catalysts A(2) thus obtained was adjusted to a homogeneous 20% by weight. The residual water content of the active material after drying was 0.2% by weight.

D) Production of an aldol condensation catalyst B whose active material is a vanadium-phosphorus oxide doped with Fe(III)

A stirred tank which was heatable externally with molecular nitrogen ($N_2$ content ≧99.99% by volume) and by means of pressurized water, had an internal volume of 8 m³, was enameled on the inner surface thereof and was equipped with baffles and an impeller stirrer was initially charged with 4602 kg of isobutanol. After the three-level impeller stirrer had been started, the isobutanol was heated to 90° C. under reflux. While maintaining this temperature, continuous supply of 690 kg of finely divided vanadium pentoxide via a conveying screw was then commenced. Once 460 kg of vanadium pentoxide ($V_2O_5$) had been added within 20 min, while continuing the supply of vanadium pentoxide, the continuous pumped addition of 805 kg of 105% by weight phosphoric acid (cf. DE-A 3520053) was commenced, in the course of which the temperature of 90° C. was maintained (pumping rate=160 kg/h).

After the addition of the phosphoric acid had ended, the mixture was heated while stirring and under reflux to temperatures in the range from 100 to 108° C. and kept within this temperature range for 14 hours. Subsequently, the hot suspension obtained was cooled to 60° C. in an essentially linear manner within 75 minutes, and 22.7 kg of iron(III) phosphate hydrate were added (Fe content: 29.9% by weight; supplier: Dr. Paul Lohmann; free of Fe(II) impurities). Then the mixture was heated, again under reflux, to temperatures of 100 to 108° C., and the suspension was kept at this temperature while continuing to stir for 1 hour. Subsequently, the suspension at approx. 105° C. was discharged into a pressure suction filter which had been inertized beforehand with nitrogen and heated to 100° C., and filtered at a pressure above the suction filter of approx. 0.35 MPa abs. The filtercake obtained was blown dry by constantly introducing nitrogen while stirring and at 100° C. within one hour. After blowing dry, the filtercake was heated to 155° C. and evacuated to a pressure of 15 kPa abs. (150 mbar abs.).

Under these conditions, the drying was performed down to a residual isobutanol content of 2% by weight in the dried precursor material. This comprised Fe and V in a molar Fe/V ratio of 0.016.

Subsequently, the dry powder was treated further in an inclined stainless steel rotating tube through which 100 m³/h of air (the inlet temperature of which was 150° C.) flowed and which had internal spiral winding. The tube length was 6.5 m, the internal diameter 0.9 m and the rotating tube wall thickness 2.5 cm. The speed of rotation of the rotating tube was 0.4 rpm. The dry powder was supplied to the rotating tube interior in an amount of 60 kg/h at the upper end thereof. The spiral winding ensured homogeneous flowing motion (downward) of the dry powder within the rotating tube. The rotating tube length was divided into five heating zones of the same length, the temperature of which was controlled from the outside. The temperatures of the five heating zones measured on the outer wall of the rotating tube were, from the top downward, 250° C., 300° C., 345° C., 345° C. and 345° C.

400 g of the powder leaving the rotating tube were, based on the weight thereof, mixed homogeneously with 1% by weight of graphite (Asbury 3160, from Timcal Ltd., cf. WO 2008/087116) (in a drum hoop mixer of wheel diameter 650 mm, drum volume 5 l, speed: 30 rpm, mixing time: 30 min). The resulting mixture was then compacted with the aid of a Powtec roll compactor with 2 contrarotary steel rolls at an applied pressure of 9 bar, and then forced through a screen with square screen meshes of size 1 mm. The resulting compactate had a bulk density of 1100 g/l and an essentially homogeneous particle size of ≧0.7 mm ands ≦0.8 mm. 30 ml of bed volume of the granules were charged into a vertical tube furnace (internal tube diameter: 26 mm; in the center of the tube, thermowell running from the top downward with an external diameter of 4 mm to accommodate a thermocouple). 25 l (STP)/h of air with an inlet temperature of 160° C. were conducted through the tube furnace. At a heating rate of 5° C./min, the temperature of the calcination material present in the tube furnace was increased from 25° C. to 250° C. On attainment of the temperature of 250° C., the temperature of the calcination material was raised at a heating rate of 2° C./min to 330° C. This temperature was maintained over a period of 40 min.

Then, while maintaining a volume flow rate of 25 l (STP)/h, air flow was switched to a flow with a mixture of 50% by volume of $N_2$ and 50% by volume of steam (the inlet temperature of which was 160° C.) through the tube furnace, and the temperature of the calcination material was raised at a heating rate of 3° C./min to 425° C. This temperature was maintained over a period of 180 min. Then, while maintaining the volume flow rate of 25 l (STP)/h, the flow was switched again to an air flow (the inlet temperature of the air stream was 25° C.). Then the temperature of the calcination material was cooled to 25° C. within 120 min.

The stoichiometry of the unsupported Fe(III)-doped vanadium-phosphorus oxide aldol condensation catalyst B prepared as described was $V_1P_{1.05}Fe_{0.016}O_n$.

II) Performance of processes A) to D) according to the invention for preparing acrylic acid from ethanol and formaldehyde using the catalysts prepared in I) (the contents of all reaction gas input mixtures and reactants were determined by gas chromatography)

A) 1. Configuration of Reaction Zone A

Reaction zone A was implemented in a tubular reactor A (internal diameter: 12 mm; wall thickness: 1.5 mm; length: 2000 mm; material: stainless steel, DIN material 1.4541), which was electrically heatable externally in sections. The catalyst charge in tubular reactor A was configured as follows:

Section 1: 300 mm of a preliminary bed of steatite spall (longest dimension 1 to 1.5 mm; C220 steatite from CeramTec) at the reactor inlet;

59 mm of a homogeneous mixture of 3.3 ml of oxidation catalyst A(1) and 3.3 ml of the steatite spall used for the preliminary bed;

Section 2: 15 mm with 1.7 ml of eggshell catalyst A(2); and 300 mm of a downstream bed of the steatite spall used for the preliminary bed.

Sections 1 and 2 directly adjoin one another.

The temperature of tubular reactor A was set to 185° C. in the region of section 1 and to 220° C. in the region of section 2 (in each case the outer wall temperature of tubular reactor A). 41.8 l (STP)/h of reaction gas input mixture A were supplied to the preliminary bed of steatite spall with an inlet temperature of 150° C. The pressure at the inlet into tubular reactor A was 2.0 bar abs.

Reaction gas input mixture A had the following contents:
1.6% by vol. of ethanol,
9.97% by vol. of steam,
5.96% by vol. of $O_2$, and
82.47% by vol. of $N_2$.

The last 1326 mm of tubular reactor A were unheated. The space velocity of reaction gas input mixture A on the catalyst charge was approx. 5000 $h^{-1}$. The space velocity of ethanol was 80 $h^{-1}$ (l(STP)/l·h).

The product gas mixture A leaving the tubular reactor A (41.9 l (STP)/h) had the following contents (online GC analysis):
11.65% by vol. of water,
81.54% by vol. of $N_2$,
4.12% by vol. of $O_2$,
1.42% by vol. of acetic acid,
0.05% by vol. of acetaldehyde,
0.22% by vol. of $CO_2$, and
<0.01% by vol. of ethanol.

2. Configuration of Reaction Zone B

Reaction zone B was implemented in a tubular reactor B (internal diameter: 15 mm; wall thickness: 1.2 mm; length: 2000 mm; material: stainless steel, DIN material 1.4541), which was electrically heatable externally. The catalyst charge in tubular reactor B was configured as follows:

1000 mm of a preliminary bed of steatite spall (as in reaction zone A) at the reactor inlet; and 753 mm with 133 ml of the unsupported aldol condensation catalyst B.

The 41.9 l (STP)/h of product gas mixture A, 2.0 l (STP)/h of an aqueous solution of formaldehyde in water which has been converted to the vapor phase and 1.3 l (STP)/h of acetic acid converted to the vapor phase (which formed stream Y) were used to obtain 45.1 l (STP)/h of reaction gas input mixture B.

The contents of the vaporized formaldehyde solution were:
0.70% by vol. of methanol,
37.23% by vol. of formaldehyde and
62.06% by vol. of water.

The contents of the vaporized acetic acid were:
99% by vol. of acetic acid.

The contents of reaction gas input mixture B were:
0.03% by vol. of methanol,
1.64% by vol. of formaldehyde,
13.54% by vol. of water,
75.65% by vol. of $N_2$,
3.82% by vol. of $O_2$,
4.07% by vol. of acetic acid,
0.04% by vol. of acetaldehyde, and
0.20% by vol. of $CO_2$.

Reaction gas input mixture B was supplied to the preliminary bed of steatite spall with an inlet temperature of 350° C. The pressure at the inlet into tubular reactor B was 1.5 bar abs. The temperature of tubular reactor B was set to 375° C. over the length of the fixed bed charge thereof (outer wall temperature of tubular reactor B). The remaining length of tubular reactor B was unheated. The space velocity of reaction gas input mixture B on the catalyst charge was 340 $h^{-1}$.

The product gas mixture B leaving tubular reactor B (45.1 l (STP)/h) had the following contents (online GC analysis):
0.02% by vol. of methanol,
0.02% by vol. of formaldehyde,
15.22% by vol. of water,
75.64% by vol. of $N_2$,
3.41% by vol. of $O_2$,
1.29% by vol. of acrylic acid,
2.78% by vol. of acetic acid,
0.59% by vol. of $CO_2$, and
0.01% by vol. of methyl acetate.

Based on the molar amount of ethanol supplied to reaction zone A, the yield of acrylic acid achieved was 87.0 mol %.

B) The reaction zone A and reaction zone B were configured as in II)A) and charged with the same catalyst beds. However, the bed length of the catalytically active portion in section 1 was 62 mm (homogeneous mixture of 3.5 ml of oxidation catalyst A(1) and 3.5 ml of steatite spall). The performance of the heterogeneously catalyzed partial oxidation of ethanol to acetic acid was performed as in II)A), but the feed flow rate of reaction gas input mixture A was 43.3 l (STP)/h. 43.4 l (STP)/h of product gas mixture A were obtained. The composition of product gas mixture A corresponded to that in II)A). The space velocity of reaction gas input mixture A on the catalyst charge in tubular reactor A was approx. 5000 $h^{-1}$.

The 43.4 l (STP)/h of product gas mixture A, a formaldehyde stream obtained by vaporizing and redissociating trioxane of 0.7 l (STP)/h, and 1.0 l (STP)/h of acetic acid converted to the vapor phase (which formed stream Y) were used to obtain 45.1 l (STP)/h of reaction gas input mixture B.

The contents of the formaldehyde stream were:
100% by vol. of formaldehyde.

The contents of the vaporized acetic acid were:
99% by vol. of acetic acid.

The contents of reaction gas input mixture B were:
1.48% by vol. of formaldehyde,
11.20% by vol. of water,
78.38% by vol. of $N_2$,
3.96% by vol. of $O_2$,
3.72% by vol. of acetic acid,
0.05% by vol. of acetaldehyde, and
0.21% by vol. of $CO_2$.

Reaction gas input mixture B was supplied to the preliminary bed of steatite spall with an inlet temperature of 320° C. The pressure at the inlet into tubular reactor B was 1.5 bar abs. The temperature of tubular reactor B was set to 340° C. over the length of its fixed bed (outer wall temperature of tubular reactor B). The remaining length of tubular reactor B was unheated. The space velocity of reaction gas input mixture B on the catalyst charge was 340 $h^{-1}$ (l(STP)/l·h).

The product gas mixture B leaving the tubular reactor B (45.1 l (STP)/h) had the following contents (online GC analysis):

0.02% by vol. of formaldehyde,
12.72% by vol. of water,
78.37% by vol. of $N_2$,
3.76% by vol. of $O_2$,
1.35% by vol. of acrylic acid,
2.38% by vol. of acetic acid, and
0.39% by vol. of $CO_2$.

Based on the amount of ethanol supplied to reaction zone A, the yield of acrylic acid achieved was 88 mol %.

C) Reaction zone A and reaction zone B were configured as in II)A) and charged with the same catalyst beds. The heterogeneously catalyzed partial oxidation of ethanol to acetic acid was performed as in II)A), but reaction gas input mixture A had the following contents:
3.00% by vol. of ethanol,
10.01% by vol. of water,
7.41% by vol. of $O_2$, and
79.57% by vol. of $N_2$.

The product gas mixture A leaving the tubular reactor A (41.9 l (STP)/h) had the following contents (online GC analysis):
0.01% by vol. of ethanol,
13.26% by vol. of water,
78.58% by vol. of $N_2$,
3.99% by vol. of $O_2$,
2.66% by vol. of acetic acid,
0.09% by vol. of acetaldehyde, ad
0.41% by vol. of $CO_2$.

The 41.9 l (STP)/h of product gas mixture A, a formaldehyde stream obtained by vaporizing and redissociating trioxane of 1.2 l (STP)/l·h, and 2.0 l (STP)/h of acetic acid converted to the vapor phase (which formed stream Y) were used to obtain 45.1 l (STP)/h of reaction gas input mixture B.

The contents of the formaldehyde stream were:
100% by vol. of formaldehyde.

The contents of the vaporized acetic acid were:
99% by vol. of acetic acid.

The contents of reaction gas input mixture B were:
0.01% by vol. of ethanol,
2.69% by vol. of formaldehyde,
12.32% by vol. of water,
73.01% by vol. of $N_2$,
3.70% by vol. of $O_2$,
6.80% by vol. of acetic acid,
0.08% by vol. of acetaldehyde, and
0.39% by vol. of $CO_2$.

Reaction gas input mixture B was supplied to the preliminary bed of steatite spall with an inlet temperature of 320° C. The pressure at the inlet into tubular reactor B was 1.5 bar abs. The temperature of tubular reactor B was set to 340° C. over the length of its fixed bed (outer wall temperature of tubular reactor B). The remaining length of tubular reactor B was unheated. The space velocity of reaction gas input mixture B on the catalyst charge was 340 $h^{-1}$.

The product gas mixture B leaving the tubular reactor B (45.1 l (STP)/h) had the following contents:
0.03% by vol. of formaldehyde,
15.1% by vol. of water,
73.0% by vol. of $N_2$,
3.34% by vol. of $O_2$,
2.45% by vol. of acrylic acid,
4.36% by vol. of acetic acid, and
0.71% by vol. of $CO_2$.

Based on the amount of ethanol supplied to reaction zone A, the yield of acrylic acid achieved was 88 mol %.

D) Reaction zone A and reaction zone B were configured as in II)A) and were charged with the same catalyst beds. However, the bed length of the catalytically active part in section 1 was 43 mm (homogeneous mixture of 2.4 ml of oxidation catalyst A(1) and 2.4 ml of steatite spall) and the bed length of the catalytically active part in section 2 was only 11 mm (1.2 ml of eggshell catalyst A(2)). The heterogeneously catalyzed partial oxidation of ethanol to acetic acid was performed as in II)A), except that reaction gas input mixture A had the following contents:
3.00% by vol. of ethanol,
10.01% by vol. of water,
7.41% by vol. of $O_2$, and
79.57% by vol. of $N_2$.

In addition, the feed flow rate of reaction gas input mixture A was only 30.6 l (STP)/h. The product gas mixture A leaving the tubular reactor A (30.6 l (STP)/h) had the following contents (online GC analysis):
0.01% by vol. of ethanol,
13.26% by vol. of water,
78.58% by vol. of $N_2$,
3.99% by vol. of $O_2$,
2.66% by vol. of acetic acid,
0.09% by vol. of acetaldehyde, and
0.41% by vol. of $CO_2$.

The 30.6 l (STP)/h of product gas mixture A, 1.8 l (STP)/h of acetic acid converted to the vapor phase (which formed stream Y) and 12.7 l (STP)/h of a formaldehyde-comprising product gas mixture C which had been obtained by heterogeneously catalyzed partial gas phase oxidation of methanol by the FORMOX process in a reaction zone C were used to obtain 45.1 l (STP)/h of reaction gas input mixture B.

The contents of the vaporized acetic acid were:
99% by vol. of acetic acid.

The contents of product gas mixture C were:
0.07% by vol. of methanol,
8.03% by vol. of formaldehyde,
11.84% by vol. of water,
73.71% by vol. of $N_2$,
4.83% by vol. of $O_2$,
0.40% by vol. of $CO_2$,
0.09% by vol. of formic acid, and
0.04% by vol. of dimethyl ether.

The contents of reaction gas input mixture B were:
0.02% by vol. of methanol,
2.26% by vol. of formaldehyde,
12.34% by vol. of water,
74.10% by vol. of $N_2$,
4.07% by vol. of $O_2$,
5.73% by vol. of acetic acid,
0.06% by vol. of acetaldehyde,
0.39% by vol. of $CO_2$,
0.02% by vol. of formic acid, and
0.01% by vol. of dimethyl ether.

Reaction gas input mixture B was supplied to the preliminary bed of steatite spall with an inlet temperature of 320° C. The pressure at the inlet into tubular reactor B was 1.5 bar abs. The temperature of tubular reactor B was set to 340° C. over the length of its fixed bed (outer wall temperature of tubular reactor B). The remaining length of tubular reactor B was unheated. The space velocity of reaction gas input mixture B on the catalyst charge was 340 $h^{-1}$.

The product gas mixture B leaving the tubular reactor B (45.1 l (STP)/h) had the following contents:
0.01% by vol. of methanol,
0.02% by vol. of formaldehyde,
14.66% by vol. of water,
74.09% by vol. of $N_2$,
3.50% by vol. of $O_2$,
1.78% by vol. of acrylic acid,
3.96% by vol. of acetic acid,
0.93% by vol. of $CO_2$,
0.01% by vol. of methyl acetate,
0.02% by vol. of formic acid, and
0.01% by vol. of dimethyl ether.

Based on the amount of ethanol supplied to reaction zone A, the yield of acrylic acid achieved was 88 mol %.

Reaction zone C was implemented in a tubular reactor C (internal diameter: 8 mm; wall thickness: 1 mm; length: 100 mm; material: stainless steel DIN material 1.4541), which was electrically heatable externally. The catalyst charge in tubular reactor C was configured as follows:

50 mm of a preliminary bed of steatite spall (as in reaction zone A) at the reactor inlet; and 37 mm with 1.87 ml of the oxidation catalyst C in spall form.

The contents of reaction gas input mixture C were:
9.15% by vol. of methanol,
3.04% by vol. of water,
77.76% by vol. of $N^2$, and
10.05% by vol. of $O_2$.

Reaction gas input mixture C (12.2 l (STP)/h) was supplied to the preliminary bed of steatite spall with an inlet temperature of 265° C. The pressure at the inlet into tubular reactor C was 2 bar abs. The temperature of tubular reactor C was set to 265° C. over the length of the fixed bed charge thereof (outer wall temperature of tubular reactor C). The remaining length of tubular reactor C was unheated. The space velocity of reaction gas input mixture C on the catalyst charge was 6500 $h^{-1}$.

U.S. Provisional Patent Application No. 61/383,358, filed Sep. 16, 2010, is incorporated into the present patent application by literature reference. With regard to the abovementioned teachings, numerous changes and deviations from the present invention are possible. It can therefore be assumed that the invention, within the scope of the appended claims, can be performed differently than the way described specifically herein.

The invention claimed is:

1. A process for preparing acrylic acid from ethanol and formaldehyde, which comprises the following measures:

a stream of a reaction gas input mixture A comprising the ethanol and molecular oxygen reactants and at least one inert diluent gas other than steam is conducted through a first reaction zone A charged with at least one oxidation catalyst A, wherein the charge of the reaction zone A with at least one oxidation catalyst A comprises two sections 1 and 2 which are spatially successive in flow direction of reaction gas input mixture A in numerical sequence thereof and are charged with different oxidation catalysts A, said at least one oxidation catalyst A of section 1 having a catalytically active material 1 which comprises at least one vanadium oxide and at least one oxide from the group of the oxides of titanium, of aluminum, of zirconium and of tin, and said at least one oxidation catalyst A of section 2 having a catalytically active material 2 which is a multimetal oxide which, as well as V and Mo, additionally comprises at least one of the elements W, Mo, Ta, Cr and Ce, and at least one of the elements Cu, Ni, Co, Fe, Mn and Zn; and, in the course of passage through reaction zone A, ethanol present in the reaction gas input mixture A is oxidized under heterogeneous catalysis to acetic acid and steam so as to form a product gas mixture A comprising acetic acid, steam, molecular oxygen and at least one inert diluent gas other than steam, and a stream of product gas mixture A leaves reaction zone A, it optionally being possible to supply further molecular oxygen and/or further inert diluent gas to the reaction gas mixture A flowing through reaction zone A on its way through reaction zone A a stream of a reaction gas input mixture B which comprises acetic acid, steam, molecular oxygen, at least one inert diluent gas other than steam and formaldehyde and in which the molar amount $n_{HAc}$ of acetic acid present is greater than the molar amount $n_{Fd}$ of formaldehyde present therein is obtained from the stream of product gas mixture A leaving reaction zone A and at least one further stream comprising at least one formaldehyde source, the stream of reaction gas input mixture B is passed through a second reaction zone B charged with at least one aldol condensation catalyst B and formaldehyde present in reaction gas input mixture B, as it flows through reaction zone B, is condensed with acetic acid present in reaction gas input mixture B under heterogeneous catalysis to give acrylic acid and $H_2O$, so as to form a product gas mixture B comprising acrylic acid, acetic acid, steam, molecular oxygen and at least one inert diluent gas other than steam, and a stream of product gas mixture B leaves reaction zone B, it optionally being possible to supply further molecular oxygen and/or further inert diluent gas to the reaction gas mixture B flowing through reaction zone B on its way through reaction zone B, the stream of product gas mixture B leaving reaction zone B is fed to a separation zone T and separated in separation zone T into at least three streams X, Y and Z, the amount of acrylic acid present in stream X is greater than the amount of acrylic acid present in streams Y and Z together, the amount of acetic acid present in stream Y is greater than the amount of acetic acid present in streams X and Z together, the amount of inert diluent gas other than steam present in stream Z is greater than the amount of inert diluent gas other than steam present in streams X and Y together, and stream Y is recycled into reaction zone B and used to obtain reaction gas input mixture B.

2. The process according to claim 1, wherein the catalytically active material 2 is at least one multimetal oxide of the general formula I

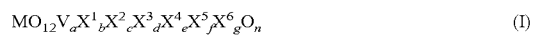

$$Mo_{12}V_aX^1_bX^2_cX^3_dX^4_eX^5_fX^6_gO_n \qquad (I)$$

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=1 to 6,
b=0.2 to 4,
c=0.5 to 1.8 d=0 to 40,
e=0 to 2,
f=0 to 4,
g=0 to 40, and
n=the stoichiometric coefficient of the element oxygen, which is determined by the stoichiometric coefficients of the non-oxygen elements and the charge numbers thereof in I.

3. The process according to claim 1, wherein reaction gas input mixture A comprises 0.75 to 10% by volume of ethanol.

4. The process according to claim 1, wherein reaction gas input mixture A comprises 1 to 40% by volume of $H_2O$.

5. The process according to claim 1, wherein reaction gas input mixture A, based on the weight of the ethanol present therein, has at least one 1 ppm by weight of a chemical compound comprising the element sulfur, calculated as the amount of sulfur present.

6. The process according to claim 1, wherein the formaldehyde source used for the formaldehyde present in reaction gas input mixture B is at least one of the sources trioxane, paraformaldehyde, formalin, methylal, aqueous paraformaldehyde solution, aqueous formaldehyde solution, and the product gas mixture of a heterogeneously catalyzed partial gas phase oxidation of methanol to formaldehyde from which any unconverted methanol present therein has optionally been removed.

7. The process according to claim 1, wherein the formaldehyde content in reaction gas input mixture B is 0.5 to 10% by volume.

8. The process according to claim 1, wherein reaction gas input mixture B comprises acetic acid in a molar amount $n_{HAc}$ and formaldehyde in a molar amount $n_{Fd}$, and the $n_{HAc}$:$n_{Fd}$ ratio is greater than 1 and $\leq 10$.

9. The process according to claim 1, wherein the acetic acid content of reaction gas input mixture B is 1.5 to 20% by volume.

10. The process according to claim 1, wherein the steam content of reaction gas input mixture B does not exceed 30% by volume and is not less than 1.5% by volume.

11. The process according to claim 1, wherein the at least one aldol condensation catalyst B has a catalytically active material which is a multielement oxide active material of the general formula II

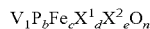 (II)

in which the variables are each defined as follows:
$X^1$=Mo, Bi, Co, Ni, Si, Zn, Hf, Zr, Ti, Cr, Mn, Cu, B, Sn and/or Nb,
$X^2$=Li, K, Na, Rb, Cs and/or Tl,
b=0.9 to 2.0
c=$\geq$0 to 0.1,
d=$\geq$0 to 0.1,
e=$\geq$0 to 0.1, and
n=the stoichiometric coefficient of the element oxygen, which is determined by the stoichiometric coefficients of the non-oxygen elements and the charge numbers thereof in II.

12. The process according to claim 1, which comprises a further, third reaction zone C which has been charged with at least one oxidation catalyst C and comprises the following additional measures:
a stream of a reaction gas input mixture C comprising the methanol and molecular oxygen reactants and at least one inert diluent gas other than steam is passed through a third reaction zone C charged with at least one oxidation catalyst C and methanol present in reaction gas input mixture C, as it passes through reaction zone C, is oxidized under heterogeneous catalysis to formaldehyde and steam, so as to form a product gas mixture C comprising formaldehyde, steam and at least one inert diluent gas other than steam, and a stream of product gas mixture C leaves reaction zone C, it optionally being possible to add further molecular oxygen and/or further inert diluent gas to reaction gas mixture C flowing through reaction zone C on its way through reaction zone C,
optionally, from product gas mixture C, any unconverted methanol still present in product gas mixture C is removed from product gas mixture C in a separation zone T* to leave a formaldehyde-comprising product gas mixture C*, and
product gas mixture C or product gas mixture C* is conducted into reaction zone B to obtain reaction gas input mixture B.

13. The process according to claim 12, wherein the at least one oxidation catalyst C has a catalytically active material which is a mixed oxide of the general formula III

 (III)

in which the variables are each defined as follows:
$M^1$=Mo and/or Fe, or
Mo and/or Fe and, based on the total molar amount of Mo and Fe, a total molar amount of up to 10 mol % of one or more elements from the group consisting of Ti, Sb, Sn, Ni, Cr, Ce, Al, Ca, Mg, V, Nb, Ag, Mn, Cu, Co, Si, Na, K, Tl, Zr, W, Ir, Ta, As, P and B,
q=0 to 5,
m=1 to 3,
n=1 to 6.

14. The process according to claim 12, wherein reaction gas input mixture C comprises 2 to 15% by volume of methanol.

15. The process according to claim 12, wherein reaction gas input mixture C comprises 0 to 20% by volume of $H_2O$.

16. The process according to claim 12, wherein a portion of stream Y is recycled into reaction zone C to obtain reaction gas input mixture C.

17. The process according to claim 1, wherein product gas mixture B is separated in separation zone T by passing product gas mixture B, optionally after direct and/or indirect cooling thereof, into a condensation column equipped with separating internals and fractionally condensing it within the condensation column and conducting streams X, Y and Z out of the condensation column as separate fractions.

18. The process according to claim 1, wherein product gas mixture B is separated in separation zone T by passing product gas mixture B, optionally after direct and/or indirect cooling thereof, into an absorption column equipped with separating internals in countercurrent to an organic solvent with a higher boiling point than acrylic acid at standard pressure, and absorbing the acetic acid and acrylic acid present in product gas mixture B into the solvent to obtain an absorbate, while a stream Z leaves the absorption column at the top thereof, and then removing streams X and Y from the absorbate as separate fractions by fractional distillation thereof in a rectification column.

19. The process according to claim 1, wherein product gas mixture B is separated in separation zone T by passing product gas mixture B, optionally after direct and/or indirect cooling thereof, into an absorption column equipped with separating internals in countercurrent to an aqueous solution as an absorbent, and absorbing the acetic acid and acrylic acid present in product gas mixture B into the solvent to obtain an absorbate, while a stream Z leaves the absorption column at the top thereof, and then removing streams X and Y as separate fractions from the absorbate by fractional distillation thereof in a rectification column.

* * * * *